US007572950B2

(12) United States Patent
Herbers et al.

(10) Patent No.: US 7,572,950 B2
(45) Date of Patent: Aug. 11, 2009

(54) METHODS FOR OBTAINING PATHOGEN RESISTANCE IN PLANTS

(75) Inventors: Karin Herbers, Quedlinburg (DE); Bettina Tschiersch, Quedlinburg (DE); Uwe Sonnewald, Quedlinburg (DE); Frederik Börnke, Quedlinburg (DE); Horst-Ekkehard Neuhaus, Kaiserslautern (DE)

(73) Assignee: SunGene GmbH & Co. KGaA (DE)

( * ) Notice: Subject to any disclaimer, the term of this patent is extended or adjusted under 35 U.S.C. 154(b) by 409 days.

(21) Appl. No.: 10/516,075

(22) PCT Filed: Jul. 2, 2003

(86) PCT No.: PCT/EP03/07027

§ 371 (c)(1),
(2), (4) Date: Nov. 29, 2004

(87) PCT Pub. No.: WO2004/005504

PCT Pub. Date: Jan. 15, 2004

(65) Prior Publication Data
US 2007/0256192 A1  Nov. 1, 2007

(30) Foreign Application Priority Data
Jul. 4, 2002 (DE) ................ 102 30 220

(51) Int. Cl.
*A01H 1/00* (2006.01)
*A01H 5/00* (2006.01)
*C12N 15/82* (2006.01)
*C12N 15/87* (2006.01)

(52) U.S. Cl. .............. 800/279; 800/287; 800/278; 435/320.1

(58) Field of Classification Search ............ None
See application file for complete search history.

(56) References Cited

U.S. PATENT DOCUMENTS

| | | | |
|---|---|---|---|
| 5,786,140 A | 7/1998 | Mattes et al. | |
| 5,985,622 A | 11/1999 | Mattes et al. | |
| 6,395,963 B1 | 5/2002 | Ohl et al. | |
| 2003/0087416 A1 | 5/2003 | Mattes et al. | |
| 2003/0159181 A1 | 8/2003 | Bornke et al. | |
| 2004/0064851 A1* | 4/2004 | Kunz et al. | 800/284 |

FOREIGN PATENT DOCUMENTS

| | | |
|---|---|---|
| DE | 44 14 185 | 1/1994 |
| JP | 2001/508661 | 1/1997 |
| WO | WO 94/10320 | 5/1994 |
| WO | WO 97/46692 | 12/1997 |
| WO | WO 98/04586 | 2/1998 |
| WO | WO 99/47552 | 9/1999 |
| WO | WO 00/01722 | 1/2000 |
| WO | WO 00/01832 | 1/2000 |
| WO | WO 01/59136 A | 2/2000 |
| WO | WO/02/27003 * | 4/2002 |
| WO | WO 03/033651 A2 | 4/2003 |

OTHER PUBLICATIONS

Falcon-Perez JM et al. 1999, J Biol Chem. 274:23584-90.*
Lazar et al. 1988, Mol. Cell. Biol. 8:1247-1252.*
Guo et al. 2004, Proc. Natl. Acad. Sci. USA 101: 9205-9210.*
Hill et al 1998, Biochem. Biophys. Res. Comm. 244:573-577.*
Veronese et al. 2003, Plant Physiology 131:1580-1590).*
Sequence alignment of SEQ ID No. 1 vs SEQ ID No. 14.*
Börnke, Frederik, et al., "Potato Tubers as Bioreactors for Palatinose Production," *Journal of Biotechnology*, 96:119-124 (2002).
Börnke, Frederik, et al., "Cloning and Characterization of the Gene Cluster for Palatinose Metabolism for the Phytopathogenic Bacterium *Erwinia rhapontici,*" *Journal of Bacteriology*, 183(8):2425-2430 (2001).
Börnke, Frederik, et al., "High-Level Production of the Non-Cariogenic Sucrose Isomer Palatinose in Transgenic Tobacco Plants Strongly Impairs Development," *Planta*, 214:356-364 (2002).
Broglie, Karen, et al., "Transgenic Plants with Enhanced Resistance to the Fungal Pathogen *Rhizoctonia solani,*" *Science*, 254:1194-1197 (1991).
Büscheges, Rainer, et al., "The Barley *Mlo* Gene: A Novel Content Element of Plant Pathogen Resistance," *Cell*, 88:695-705 (1997).
Custers, Jerome H.H.V., et al., "T-DNA Tagging of a Pathogen Inducible Promoter in *Arabidopsis thaliana,*" *Molecular Plant Pathology*, 3(4):239-249 (2002).
Escobar, Carolina, et al., "Isolation of the *LEMMI9* Gene and Promoter Analysis During a Compatible Plant-Nematode Interaction," *Molecular Plant-Microbe Interactions*, 12(5):440-449 (1999).
Fenoll, Carmen, et al., "The Molecules Basis of Nematode Endoparasitism in Plants," *Physiol. Mol. Biol. Plants*, 4:9-18 (1998).
Friedrich, Leslie, et al., "A Benzothiadiazole Derivative Induces Systemic Acquired Resistance in Tobacco," *The Plant Journal*, 10(1):61-70 (1996).
Jorgensen, J. Helms, "Spectrum of Resistance Conferred by *ML-O* Powdery Mildew Resistance Genes in Barley," *Euphytica*, 26:55-62 (1977).
Karimi, M., et al., "Activation of a Pollenin Promoter Upon Nematode Infection," *Journal of Nematology*, 34(2):75-79 (2002).
Keil, Michael, et al., "Primary Structure of a Proteinase Inhibitor II Gene from Potato (*Solanum tuberosum*," *Nucleic Acids Research*, 14(14):5641-5650 (1986).
Lawton, Kay A., et al., "Benzothiadiazole Induces Disease Resistance in *Arabidopsis* by Activation of the Systemic Acquired Resistance Signal Transduction Pathway," *The Plant Journal*, 10(1):71-82 (1996).
Lyngkjaer, M.F., et al., "A Japanese Powdery Mildew Isolate with Exceptionally Large Infection Effeciency on Mlo-Resistant Barley," *Plant Pathology*, 44:786-790 (1995).

(Continued)

*Primary Examiner*—Elizabeth F McElwain
*Assistant Examiner*—Li Zheng
(74) *Attorney, Agent, or Firm*—Connolly Bove Lodge & Hutz LLP

(57) ABSTRACT

The invention relates to methods for generating or increasing a pathogen resistance in plants by expression, preferably pathogen-inducible expression, of a sucrose isomerase.

10 Claims, 8 Drawing Sheets

OTHER PUBLICATIONS

Opperman, Charles H., et al., "Root-Knot Nematode-Directed Expression of a Plant Root-Specific Gene," *Science*, 263:221-223 (1994).

Rocha-Sosa, Mario, et al., "Both Developmental and Metabolic Signals Activate the Promoter of a Class I Patatin Gene," *The EMBO Journal*, 8(1):23-29 (1989).

Sonnewald, Uwe, et al., "Transgenic Tobacco Plants Expressing Yeast-Derived Invertase in Either the Cytosol, Vacuole or Apoplast: A Powerful Tool for Studying Sucrose Metabolism and Sink-Source Interactions," *The Plant Journal*, 1(1):95-106 (1991).

Sijmons, P.C., et al., "Parasitic Strategies of Root Nematodes and Associated Host Cell Responses," *Ann. Rev. Phytopathol.*, 32:235-259 (1994).

Schulze-Lefert, Paul, et al., "Closing the Ranks to Attack by Powdery Mildew," *Trends in Plant Science*, 5(8):343-348 (2000).

Uknes, Scott, et al., "Acquired Resistance in *Arabidopsis*," *The Plant Cell*, 4:645-656 (1992).

Vaeck, Mark, et al., "Transgenic Plants Protected from Insect Attack," *Nature*, 328:33-37 (1987).

Ward, Eric R., et al., "Coordinate Gene Activity in Response to Agents that Induce Systemic Acquired Resistance," *The Plant Cell*, 3:1085-1094 (1991).

Zhang, Daohai, et al., "Isomaltulose Synthesis from *Klebsiella* sp. Strain LX3: Gene Cloning and Characterization and Engineering the Thermostability," *Applied and Environmental Microbiology*, 68(6):2676-2682 (2002).

GeneBank Accession No. A79355.
GeneBank Accession No. A91914.
GeneBank Accession No. AF279281.
GeneBank Accession No. AY040843.
GeneBank Accession No. BD056958.
GeneBank Accession No. X04118.

* cited by examiner

SEQUENCE LISTING

```
<160> NUMBER OF SEQ ID NOS: 36

<210> SEQ ID NO 1
<211> LENGTH: 1890
<212> TYPE: DNA
<213> ORGANISM: Protaminobacter rubrum
<220> FEATURE:
<221> NAME/KEY: CDS
<222> LOCATION: (1)..(1887)
<223> OTHER INFORMATION: coding for sucrose isomerase

<400> SEQUENCE: 1 atg ccc cgt caa gga ttg aaa act gca cta gcg att ttt cta acc aca      48
Met Pro Arg Gln Gly Leu Lys Thr Ala Leu Ala Ile Phe Leu Thr Thr
 1               5                  10                  15 tca tta tgc atc tca tgc cag caa gcc ttc ggt acg caa caa ccc ttg      96
Ser Leu Cys Ile Ser Cys Gln Gln Ala Phe Gly Thr Gln Gln Pro Leu
             20                  25                  30 ctt aac gaa aag agt atc gaa cag tcg aaa acc ata cct aaa tgg tgg     144
Leu Asn Glu Lys Ser Ile Glu Gln Ser Lys Thr Ile Pro Lys Trp Trp
         35                  40                  45 aag gag gct gtt ttt tat cag gtg tat ccg cgc tcc ttt aaa gac acc     192
Lys Glu Ala Val Phe Tyr Gln Val Tyr Pro Arg Ser Phe Lys Asp Thr
     50                  55                  60 aac gga gat ggc atc ggg gat att aac ggc atc ata gaa aaa tta gac     240
```

```
                Asn Gly Asp Gly Ile Gly Asp Ile Asn Gly Ile Ile Glu Lys Leu Asp
                 65                  70                  75                  80 tat cta aaa gcc ttg ggg att gat gcc att tgg atc aac cca cat tat         288
Tyr Leu Lys Ala Leu Gly Ile Asp Ala Ile Trp Ile Asn Pro His Tyr
                    85                  90                  95 gat tct ccg aac acg gat aat ggt tac gat ata cgt gat tat cga aaa         336
Asp Ser Pro Asn Thr Asp Asn Gly Tyr Asp Ile Arg Asp Tyr Arg Lys
                100                 105                 110 atc atg aaa gaa tat ggc acg atg gag gat ttt gac cgc ctg att tct         384
Ile Met Lys Glu Tyr Gly Thr Met Glu Asp Phe Asp Arg Leu Ile Ser
                115                 120                 125 gaa atg aaa aaa cgg aat atg cgg ttg atg att gat gtg gtc atc aac         432
Glu Met Lys Lys Arg Asn Met Arg Leu Met Ile Asp Val Val Ile Asn
    130                 135                 140 cac acc agc gat caa aac gaa tgg ttt gtt aaa agt aaa agc agt aag         480
His Thr Ser Asp Gln Asn Glu Trp Phe Val Lys Ser Lys Ser Ser Lys
145                 150                 155                 160 gat aat cct tat cgc ggc tat tat ttc tgg aaa gat gct aaa gaa ggg         528
Asp Asn Pro Tyr Arg Gly Tyr Tyr Phe Trp Lys Asp Ala Lys Glu Gly
                165                 170                 175 cag gcg cct aat aat tac cct tca ttc ttt ggt ggc tcg gcg tgg caa         576
Gln Ala Pro Asn Asn Tyr Pro Ser Phe Phe Gly Gly Ser Ala Trp Gln
                180                 185                 190 aaa gat gaa aag acc aat caa tac tac ctg cac tat ttt gct aaa caa         624
Lys Asp Glu Lys Thr Asn Gln Tyr Tyr Leu His Tyr Phe Ala Lys Gln
                195                 200                 205 cag cct gac cta aac tgg gat aat ccc aaa gtc cgt caa gat ctt tat         672
Gln Pro Asp Leu Asn Trp Asp Asn Pro Lys Val Arg Gln Asp Leu Tyr
    210                 215                 220 gca atg tta cgt ttc tgg tta gat aaa ggc gtg tct ggt tta cgt ttt         720
Ala Met Leu Arg Phe Trp Leu Asp Lys Gly Val Ser Gly Leu Arg Phe
225                 230                 235                 240 gat acg gta gcg acc tac tca aaa att ccg gat ttc cca aat ctc acc         768
Asp Thr Val Ala Thr Tyr Ser Lys Ile Pro Asp Phe Pro Asn Leu Thr
                245                 250                 255 caa caa cag ctg aag aat ttt gca gcg gag tat acc aag ggc cct aat         816
Gln Gln Gln Leu Lys Asn Phe Ala Ala Glu Tyr Thr Lys Gly Pro Asn
                260                 265                 270 att cat cgt tac gtc aat gaa atg aat aaa gag gtc ttg tct cat tac         864
Ile His Arg Tyr Val Asn Glu Met Asn Lys Glu Val Leu Ser His Tyr
                275                 280                 285 gac att gcg act gcc ggt gaa atc ttt ggc gta ccc ttg gat caa tcg         912
Asp Ile Ala Thr Ala Gly Glu Ile Phe Gly Val Pro Leu Asp Gln Ser
    290                 295                 300 ata aag ttc ttc gat cgc cgc cgt gat gag ctg aac att gca ttt acc         960
Ile Lys Phe Phe Asp Arg Arg Arg Asp Glu Leu Asn Ile Ala Phe Thr
305                 310                 315                 320 ttt gac tta atc aga ctc gat cga gac tct gat caa aga tgg cgt cga        1008
Phe Asp Leu Ile Arg Leu Asp Arg Asp Ser Asp Gln Arg Trp Arg Arg
                325                 330                 335 aaa gat tgg aaa ttg tcg caa ttc cgg cag atc atc gat aac gtt gac        1056
Lys Asp Trp Lys Leu Ser Gln Phe Arg Gln Ile Ile Asp Asn Val Asp
                340                 345                 350 cgt act gca gga gaa tat ggt tgg aat gcc ttc ttc ttg gat aac cac        1104
Arg Thr Ala Gly Glu Tyr Gly Trp Asn Ala Phe Phe Leu Asp Asn His
                355                 360                 365 gac aat ccg cgc gct gtc tcg cac ttt ggc gat gat gat cgc cca caa        1152
Asp Asn Pro Arg Ala Val Ser His Phe Gly Asp Asp Asp Arg Pro Gln
    370                 375                 380
```

| | | |
|---|---|---|
| tgg cgt gag cca tcg gct aaa gcg ctt gca acc ttg acg ctg act caa<br>Trp Arg Glu Pro Ser Ala Lys Ala Leu Ala Thr Leu Thr Leu Thr Gln<br>385                      390                  395                  400 | 1200 |
| cga gca aca cct ttt att tat caa ggt tca gaa ttg ggc atg acc aat<br>Arg Ala Thr Pro Phe Ile Tyr Gln Gly Ser Glu Leu Gly Met Thr Asn<br>                  405                  410                  415 | 1248 |
| tac ccg ttt aaa gct att gat gaa ttc gat gat att gag gtg aaa ggt<br>Tyr Pro Phe Lys Ala Ile Asp Glu Phe Asp Asp Ile Glu Val Lys Gly<br>            420                  425                  430 | 1296 |
| ttt tgg cat gac tac gtt gag aca gga aag gtc aaa gcc gac gag ttc<br>Phe Trp His Asp Tyr Val Glu Thr Gly Lys Val Lys Ala Asp Glu Phe<br>                435                  440                  445 | 1344 |
| ttg caa aat gta cgc ctg acg agc agg gat aac agc cgg acg ccg ttc<br>Leu Gln Asn Val Arg Leu Thr Ser Arg Asp Asn Ser Arg Thr Pro Phe<br>450                      455                  460 | 1392 |
| caa tgg gat ggg agc aaa aat gca gga ttc acg agc gga aaa cct tgg<br>Gln Trp Asp Gly Ser Lys Asn Ala Gly Phe Thr Ser Gly Lys Pro Trp<br>465                      470                  475                  480 | 1440 |
| ttc aag gtc aac cca aac tac cag gaa atc aat gca gta agt caa gtc<br>Phe Lys Val Asn Pro Asn Tyr Gln Glu Ile Asn Ala Val Ser Gln Val<br>                485                  490                  495 | 1488 |
| aca caa ccc gac tca gta ttt aac tat tat cgt cag ttg atc aag ata<br>Thr Gln Pro Asp Ser Val Phe Asn Tyr Tyr Arg Gln Leu Ile Lys Ile<br>            500                  505                  510 | 1536 |
| agg cat gac atc ccg gca ctg acc tat ggt aca tac acc gat ttg gat<br>Arg His Asp Ile Pro Ala Leu Thr Tyr Gly Thr Tyr Thr Asp Leu Asp<br>                515                  520                  525 | 1584 |
| cct gca aat gat tcg gtc tac gcc tat aca cgc agc ctt ggg gcg gaa<br>Pro Ala Asn Asp Ser Val Tyr Ala Tyr Thr Arg Ser Leu Gly Ala Glu<br>530                      535                  540 | 1632 |
| aaa tat ctt gtt gtt gtt aac ttc aag gag caa atg atg aga tat aaa<br>Lys Tyr Leu Val Val Val Asn Phe Lys Glu Gln Met Met Arg Tyr Lys<br>545                      550                  555                  560 | 1680 |
| tta ccg gat aat tta tcc att gag aaa gtg att ata gac agc aac agc<br>Leu Pro Asp Asn Leu Ser Ile Glu Lys Val Ile Ile Asp Ser Asn Ser<br>                565                  570                  575 | 1728 |
| aaa aac gtg gtg aaa aag aat gat tca tta ctc gag cta aaa cca tgg<br>Lys Asn Val Val Lys Lys Asn Asp Ser Leu Leu Glu Leu Lys Pro Trp<br>            580                  585                  590 | 1776 |
| cag tca ggg gtt tat aaa act aaa tca ata aat ctc ata gtc acg cca<br>Gln Ser Gly Val Tyr Lys Thr Lys Ser Ile Asn Leu Ile Val Thr Pro<br>                595                  600                  605 | 1824 |
| aat aat gta aat ata ttg aaa cta tta aaa ccg gca ttt tat gcc ggt<br>Asn Asn Val Asn Ile Leu Lys Leu Leu Lys Pro Ala Phe Tyr Ala Gly<br>610                      615                  620 | 1872 |
| ttt ttt agc gca aaa tag<br>Phe Phe Ser Ala Lys<br>625 | 1890 |

```
<210> SEQ ID NO 2
<211> LENGTH: 629
<212> TYPE: PRT
<213> ORGANISM: Protaminobacter rubrum

<400> SEQUENCE: 2
```

Met Pro Arg Gln Gly Leu Lys Thr Ala Leu Ala Ile Phe Leu Thr Thr
 1               5                  10                  15

Ser Leu Cys Ile Ser Cys Gln Gln Ala Phe Gly Thr Gln Gln Pro Leu
            20                  25                  30

Leu Asn Glu Lys Ser Ile Glu Gln Ser Lys Thr Ile Pro Lys Trp Trp

```
                 35                  40                  45
Lys Glu Ala Val Phe Gln Val Tyr Pro Arg Ser Phe Lys Asp Thr
             50                  55                  60

Asn Gly Asp Gly Ile Gly Asp Ile Asn Gly Ile Ile Glu Lys Leu Asp
 65                  70                  75                  80

Tyr Leu Lys Ala Leu Gly Ile Asp Ala Ile Trp Ile Asn Pro His Tyr
                 85                  90                  95

Asp Ser Pro Asn Thr Asp Asn Gly Tyr Asp Ile Arg Asp Tyr Arg Lys
                100                 105                 110

Ile Met Lys Glu Tyr Gly Thr Met Glu Asp Phe Asp Arg Leu Ile Ser
                115                 120                 125

Glu Met Lys Lys Arg Asn Met Arg Leu Met Ile Asp Val Val Ile Asn
130                 135                 140

His Thr Ser Asp Gln Asn Glu Trp Phe Val Lys Ser Lys Ser Ser Lys
145                 150                 155                 160

Asp Asn Pro Tyr Arg Gly Tyr Tyr Phe Trp Lys Asp Ala Lys Glu Gly
                165                 170                 175

Gln Ala Pro Asn Asn Tyr Pro Ser Phe Phe Gly Gly Ser Ala Trp Gln
                180                 185                 190

Lys Asp Glu Lys Thr Asn Gln Tyr Tyr Leu His Tyr Phe Ala Lys Gln
                195                 200                 205

Gln Pro Asp Leu Asn Trp Asp Asn Pro Lys Val Arg Gln Asp Leu Tyr
210                 215                 220

Ala Met Leu Arg Phe Trp Leu Asp Lys Gly Val Ser Gly Leu Arg Phe
225                 230                 235                 240

Asp Thr Val Ala Thr Tyr Ser Lys Ile Pro Asp Phe Pro Asn Leu Thr
                245                 250                 255

Gln Gln Gln Leu Lys Asn Phe Ala Ala Glu Tyr Thr Lys Gly Pro Asn
                260                 265                 270

Ile His Arg Tyr Val Asn Glu Met Asn Lys Glu Val Leu Ser His Tyr
                275                 280                 285

Asp Ile Ala Thr Ala Gly Glu Ile Phe Gly Val Pro Leu Asp Gln Ser
290                 295                 300

Ile Lys Phe Phe Asp Arg Arg Arg Asp Glu Leu Asn Ile Ala Phe Thr
305                 310                 315                 320

Phe Asp Leu Ile Arg Leu Asp Arg Asp Ser Asp Gln Arg Trp Arg Arg
                325                 330                 335

Lys Asp Trp Lys Leu Ser Gln Phe Arg Gln Ile Ile Asp Asn Val Asp
                340                 345                 350

Arg Thr Ala Gly Glu Tyr Gly Trp Asn Ala Phe Phe Leu Asp Asn His
                355                 360                 365

Asp Asn Pro Arg Ala Val Ser His Phe Gly Asp Asp Arg Pro Gln
370                 375                 380

Trp Arg Glu Pro Ser Ala Lys Ala Leu Ala Thr Leu Thr Leu Thr Gln
385                 390                 395                 400

Arg Ala Thr Pro Phe Ile Tyr Gln Gly Ser Glu Leu Gly Met Thr Asn
                405                 410                 415

Tyr Pro Phe Lys Ala Ile Asp Glu Phe Asp Asp Ile Glu Val Lys Gly
                420                 425                 430

Phe Trp His Asp Tyr Val Glu Thr Gly Lys Val Lys Ala Asp Glu Phe
                435                 440                 445

Leu Gln Asn Val Arg Leu Thr Ser Arg Asp Asn Ser Arg Thr Pro Phe
450                 455                 460
```

```
Gln Trp Asp Gly Ser Lys Asn Ala Gly Phe Thr Ser Gly Lys Pro Trp
465                 470                 475                 480

Phe Lys Val Asn Pro Asn Tyr Gln Glu Ile Asn Ala Val Ser Gln Val
            485                 490                 495

Thr Gln Pro Asp Ser Val Phe Asn Tyr Tyr Arg Gln Leu Ile Lys Ile
            500                 505                 510

Arg His Asp Ile Pro Ala Leu Thr Tyr Gly Thr Tyr Thr Asp Leu Asp
            515                 520                 525

Pro Ala Asn Asp Ser Val Tyr Ala Tyr Thr Arg Ser Leu Gly Ala Glu
            530                 535                 540

Lys Tyr Leu Val Val Asn Phe Lys Glu Gln Met Met Arg Tyr Lys
545                 550                 555                 560

Leu Pro Asp Asn Leu Ser Ile Glu Lys Val Ile Asp Ser Asn Ser
                565                 570                 575

Lys Asn Val Val Lys Lys Asn Asp Ser Leu Leu Glu Leu Lys Pro Trp
                580                 585                 590

Gln Ser Gly Val Tyr Lys Thr Lys Ser Ile Asn Leu Ile Val Thr Pro
                595                 600                 605

Asn Asn Val Asn Ile Leu Lys Leu Leu Lys Pro Ala Phe Tyr Ala Gly
610                 615                 620

Phe Phe Ser Ala Lys
625

<210> SEQ ID NO 3
<211> LENGTH: 1305
<212> TYPE: DNA
<213> ORGANISM: Erwinia rhapontici
<220> FEATURE:
<221> NAME/KEY: CDS
<222> LOCATION: (1)..(1305)
<223> OTHER INFORMATION: coding for N-terminal fragment of sucrose
      isomerase
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (85)..(87)
<223> OTHER INFORMATION: n is a, c, g, or t

<400> SEQUENCE: 3 atg tcc tct caa gga ttg aaa acg gct ntc gct att ttt ctt gca acc      48
Met Ser Ser Gln Gly Leu Lys Thr Ala Xaa Ala Ile Phe Leu Ala Thr
1               5                   10                  15 act ttt tct gcc aca tcc tat cag gcc tgc agt gcc nnn cca gat acc      96
Thr Phe Ser Ala Thr Ser Tyr Gln Ala Cys Ser Ala Xaa Pro Asp Thr
            20                  25                  30 gcc ccc tca ctc acc gtt cag caa tca aat gcc ctg ccc aca tgg tgg     144
Ala Pro Ser Leu Thr Val Gln Gln Ser Asn Ala Leu Pro Thr Trp Trp
        35                  40                  45 aag cag gct gtt ttt tat cag gta tat cca cgc tca ttt aaa gat acg     192
Lys Gln Ala Val Phe Tyr Gln Val Tyr Pro Arg Ser Phe Lys Asp Thr
    50                  55                  60 aat ggg gat ggc att ggg gat tta aac ggt att att gag aat tta gac     240
Asn Gly Asp Gly Ile Gly Asp Leu Asn Gly Ile Ile Glu Asn Leu Asp
65                  70                  75                  80 tat ctg aag aaa ctg ggt att gat gcg att tgg atc aat cca cat tac     288
Tyr Leu Lys Lys Leu Gly Ile Asp Ala Ile Trp Ile Asn Pro His Tyr
                85                  90                  95
```

```
                                                   -continued gat tcg ccg aat acg gat aat ggt tat gac atc cgg gat tac cgt aag      336
Asp Ser Pro Asn Thr Asp Asn Gly Tyr Asp Ile Arg Asp Tyr Arg Lys
            100                 105                 110 ata atg aaa gaa tac ggt acg atg gaa gac ttt gac cgt ctt att tca      384
Ile Met Lys Glu Tyr Gly Thr Met Glu Asp Phe Asp Arg Leu Ile Ser
        115                 120                 125 gaa atg aag aaa cgc aat atg cgt ttg atg att gat att gtt atc aac      432
Glu Met Lys Lys Arg Asn Met Arg Leu Met Ile Asp Ile Val Ile Asn
    130                 135                 140 cac acc agc gat cag cat gcc tgg ttt gtt cag agc aaa tcg ggt aag      480
His Thr Ser Asp Gln His Ala Trp Phe Val Gln Ser Lys Ser Gly Lys
145                 150                 155                 160 aac aac ccc tac agg gac tat tac ttc tgg cgt gac ggt aag gat ggc      528
Asn Asn Pro Tyr Arg Asp Tyr Tyr Phe Trp Arg Asp Gly Lys Asp Gly
                165                 170                 175 cat gcc ccc aat aac tat ccc tcc ttc ttc ggt ggc tca gcc tgg gaa      576
His Ala Pro Asn Asn Tyr Pro Ser Phe Phe Gly Gly Ser Ala Trp Glu
            180                 185                 190 aaa gac gat aaa tca ggc cag tat tac ctc cat tac ttt gcc aaa cag      624
Lys Asp Asp Lys Ser Gly Gln Tyr Tyr Leu His Tyr Phe Ala Lys Gln
        195                 200                 205 caa ccc gac ctc aac tgg gac aat ccc aaa gtc cgt caa gac ctg tat      672
Gln Pro Asp Leu Asn Trp Asp Asn Pro Lys Val Arg Gln Asp Leu Tyr
    210                 215                 220 gac atg ctc cgc ttc tgg tta gat aaa ggc gtt tct ggt tta cgc ttt      720
Asp Met Leu Arg Phe Trp Leu Asp Lys Gly Val Ser Gly Leu Arg Phe
225                 230                 235                 240 gat acc gtt gcc acc tac tcg aaa atc ccg aac ttc cct gac ctt agc      768
Asp Thr Val Ala Thr Tyr Ser Lys Ile Pro Asn Phe Pro Asp Leu Ser
                245                 250                 255 caa cag cag tta aaa aat ttc gcc gag gaa tat act aaa ggt cct aaa      816
Gln Gln Gln Leu Lys Asn Phe Ala Glu Glu Tyr Thr Lys Gly Pro Lys
            260                 265                 270 att cac gac tac gtg aat gaa atg aac aga gaa gta tta tcc cac tat      864
Ile His Asp Tyr Val Asn Glu Met Asn Arg Glu Val Leu Ser His Tyr
        275                 280                 285 gat atc gcc act gcg ggg gaa ata ttt ggg gtt cct ctg gat aaa tcg      912
Asp Ile Ala Thr Ala Gly Glu Ile Phe Gly Val Pro Leu Asp Lys Ser
    290                 295                 300 att aag ttt ttc gat cgc cgt aga aat gaa tta aat ata gcg ttt acg      960
Ile Lys Phe Phe Asp Arg Arg Arg Asn Glu Leu Asn Ile Ala Phe Thr
305                 310                 315                 320 ttt gat ctg atc agg ctc gat cgt gat gct gat gaa aga tgg cgg cga     1008
Phe Asp Leu Ile Arg Leu Asp Arg Asp Ala Asp Glu Arg Trp Arg Arg
                325                 330                 335 aaa gac tgg acc ctt tcg cag ttc cga aaa att gtc gat aag gtt gac     1056
Lys Asp Trp Thr Leu Ser Gln Phe Arg Lys Ile Val Asp Lys Val Asp
            340                 345                 350 caa acg gca gga gag tat ggg tgg aat gcc ttt ttc tta gac aat cac     1104
Gln Thr Ala Gly Glu Tyr Gly Trp Asn Ala Phe Phe Leu Asp Asn His
        355                 360                 365 gac aat ccc cgc gcg gtt tct cac ttt ggt gat gat cga cca caa tgg     1152
Asp Asn Pro Arg Ala Val Ser His Phe Gly Asp Asp Arg Pro Gln Trp
    370                 375                 380 cgc gag cat gcg gcg aaa gca ctg gca aca ttg acg ctg acc cag cgt     1200
Arg Glu His Ala Ala Lys Ala Leu Ala Thr Leu Thr Leu Thr Gln Arg
385                 390                 395                 400 gca acg ccg ttt atc tat cag ggt tca gaa ctc ggt atg acc aat tat     1248
Ala Thr Pro Phe Ile Tyr Gln Gly Ser Glu Leu Gly Met Thr Asn Tyr
                405                 410                 415
```

```
ccc ttt aaa aaa atc gat gat ttc gat gat gta gag gtg aaa ggt ttt    1296
Pro Phe Lys Lys Ile Asp Asp Phe Asp Asp Val Glu Val Lys Gly Phe
        420                 425                 430 tgg caa gac                                                         1305
Trp Gln Asp
    435

<210> SEQ ID NO 4
<211> LENGTH: 435
<212> TYPE: PRT
<213> ORGANISM: Erwinia rhapontici
<220> FEATURE:
<221> NAME/KEY: misc_feature
<222> LOCATION: (10)..(10)
<223> OTHER INFORMATION: The 'Xaa' at location 10 stands for Ile, Val,
      Leu, or Phe.
<220> FEATURE:
<221> NAME/KEY: misc_feature
<222> LOCATION: (29)..(29)
<223> OTHER INFORMATION: The 'Xaa' at location 29 stands for Lys, Asn,
      Arg, Ser, Thr, Ile, Met, Glu, Asp, Gly, Ala, Val, Gln, His, Pro,
      Leu, Tyr, Trp, Cys, or Phe.

<400> SEQUENCE: 4

Met Ser Ser Gln Gly Leu Lys Thr Ala Xaa Ala Ile Phe Leu Ala Thr
 1               5                  10                  15

Thr Phe Ser Ala Thr Ser Tyr Gln Ala Cys Ser Ala Xaa Pro Asp Thr
            20                  25                  30

Ala Pro Ser Leu Thr Val Gln Gln Ser Asn Ala Leu Pro Thr Trp Trp
        35                  40                  45

Lys Gln Ala Val Phe Tyr Gln Val Tyr Pro Arg Ser Phe Lys Asp Thr
    50                  55                  60

Asn Gly Asp Gly Ile Gly Asp Leu Asn Gly Ile Ile Glu Asn Leu Asp
 65                  70                  75                  80

Tyr Leu Lys Lys Leu Gly Ile Asp Ala Ile Trp Ile Asn Pro His Tyr
                85                  90                  95

Asp Ser Pro Asn Thr Asp Asn Gly Tyr Asp Ile Arg Asp Tyr Arg Lys
            100                 105                 110

Ile Met Lys Glu Tyr Gly Thr Met Glu Asp Phe Asp Arg Leu Ile Ser
        115                 120                 125

Glu Met Lys Lys Arg Asn Met Arg Leu Met Ile Asp Ile Val Ile Asn
    130                 135                 140

His Thr Ser Asp Gln His Ala Trp Phe Val Gln Ser Lys Ser Gly Lys
145                 150                 155                 160

Asn Asn Pro Tyr Arg Asp Tyr Tyr Phe Trp Arg Asp Gly Lys Asp Gly
                165                 170                 175

His Ala Pro Asn Asn Tyr Pro Ser Phe Phe Gly Gly Ser Ala Trp Glu
            180                 185                 190

Lys Asp Asp Lys Ser Gly Gln Tyr Tyr Leu His Tyr Phe Ala Lys Gln
        195                 200                 205

Gln Pro Asp Leu Asn Trp Asp Asn Pro Lys Val Arg Gln Asp Leu Tyr
    210                 215                 220

Asp Met Leu Arg Phe Trp Leu Asp Lys Gly Val Ser Gly Leu Arg Phe
225                 230                 235                 240

Asp Thr Val Ala Thr Tyr Ser Lys Ile Pro Asn Phe Pro Asp Leu Ser
                245                 250                 255

Gln Gln Gln Leu Lys Asn Phe Ala Glu Glu Tyr Thr Lys Gly Pro Lys
            260                 265                 270
```

```
Ile His Asp Tyr Val Asn Glu Met Asn Arg Glu Val Leu Ser His Tyr
        275                 280                 285

Asp Ile Ala Thr Ala Gly Glu Ile Phe Gly Val Pro Leu Asp Lys Ser
        290                 295                 300

Ile Lys Phe Phe Asp Arg Arg Asn Glu Leu Asn Ile Ala Phe Thr
305                 310                 315                 320

Phe Asp Leu Ile Arg Leu Asp Arg Asp Ala Asp Glu Arg Trp Arg Arg
                    325                 330                 335

Lys Asp Trp Thr Leu Ser Gln Phe Arg Lys Ile Val Asp Lys Val Asp
                    340                 345                 350

Gln Thr Ala Gly Glu Tyr Gly Trp Asn Ala Phe Phe Leu Asp Asn His
                    355                 360                 365

Asp Asn Pro Arg Ala Val Ser His Phe Gly Asp Arg Pro Gln Trp
        370                 375                 380

Arg Glu His Ala Ala Lys Ala Leu Ala Thr Leu Thr Leu Thr Gln Arg
385                 390                 395                 400

Ala Thr Pro Phe Ile Tyr Gln Gly Ser Glu Leu Gly Met Thr Asn Tyr
                    405                 410                 415

Pro Phe Lys Lys Ile Asp Asp Phe Asp Asp Val Glu Val Lys Gly Phe
                    420                 425                 430

Trp Gln Asp
        435

<210> SEQ ID NO 5
<211> LENGTH: 1803
<212> TYPE: DNA
<213> ORGANISM: Erwinia rhapontici
<220> FEATURE:
<221> NAME/KEY: CDS
<222> LOCATION: (1)..(1800)
<223> OTHER INFORMATION: coding for sucrose isomerase

<400> SEQUENCE: 5 atg tcc tct caa gga ttg aaa acg gct gtc gct att ttt ctt gca acc        48
Met Ser Ser Gln Gly Leu Lys Thr Ala Val Ala Ile Phe Leu Ala Thr
  1               5                  10                  15 act ttt tct gcc aca tcc tat cag gcc tgc agt gcc ggg cca gat acc        96
Thr Phe Ser Ala Thr Ser Tyr Gln Ala Cys Ser Ala Gly Pro Asp Thr
                 20                  25                  30 gcc ccc tca ctc acc gtt cag caa tca aat gcc ctg ccc aca tgg tgg       144
Ala Pro Ser Leu Thr Val Gln Gln Ser Asn Ala Leu Pro Thr Trp Trp
             35                  40                  45 aag cag gct gtt ttt tat cag gta tat cca cgc tca ttt aaa gat acg       192
Lys Gln Ala Val Phe Tyr Gln Val Tyr Pro Arg Ser Phe Lys Asp Thr
         50                  55                  60 aat ggg gat ggc att ggg gat tta aac ggt att att gag aat tta gac       240
Asn Gly Asp Gly Ile Gly Asp Leu Asn Gly Ile Ile Glu Asn Leu Asp
 65                  70                  75                  80 tat ctg aag aaa ctg ggt att gat gcg att tgg atc aat cca cat tac       288
Tyr Leu Lys Lys Leu Gly Ile Asp Ala Ile Trp Ile Asn Pro His Tyr
                 85                  90                  95 gat tcg ccg aat acg gat aat ggt tat gac atc cgg gat tac cgt aag       336
Asp Ser Pro Asn Thr Asp Asn Gly Tyr Asp Ile Arg Asp Tyr Arg Lys
                100                 105                 110 ata atg aaa gaa tac ggt acg atg gaa gac ttt gac cgt ctt att tca       384
Ile Met Lys Glu Tyr Gly Thr Met Glu Asp Phe Asp Arg Leu Ile Ser
            115                 120                 125 gaa atg aag aaa cgc aat atg cgt ttg atg att gat att gtt atc aac       432
Glu Met Lys Lys Arg Asn Met Arg Leu Met Ile Asp Ile Val Ile Asn
```

-continued

```
              130                 135                 140
cac acc agc gat cag cat gcc tgg ttt gtt cag agc aaa tcg ggt aag      480
His Thr Ser Asp Gln His Ala Trp Phe Val Gln Ser Lys Ser Gly Lys
145                 150                 155                 160 aac aac ccc tac agg gac tat tac ttc tgg cgt gac ggt aag gat ggc      528
Asn Asn Pro Tyr Arg Asp Tyr Tyr Phe Trp Arg Asp Gly Lys Asp Gly
                165                 170                 175 cat gcc ccc aat aac tat ccc tcc ttc ttc ggt ggc tca gcc tgg gaa      576
His Ala Pro Asn Asn Tyr Pro Ser Phe Phe Gly Gly Ser Ala Trp Glu
            180                 185                 190 aaa gac gat aaa tca ggc cag tat tac ctc cat tac ttt gcc aaa cag      624
Lys Asp Asp Lys Ser Gly Gln Tyr Tyr Leu His Tyr Phe Ala Lys Gln
        195                 200                 205 caa ccc gac ctc aac tgg gac aat ccc aaa gtc cgt caa gac ctg tat      672
Gln Pro Asp Leu Asn Trp Asp Asn Pro Lys Val Arg Gln Asp Leu Tyr
    210                 215                 220 gac atg ctc cgc ttc tgg tta gat aaa ggc gtt tct ggt tta cgc ttt      720
Asp Met Leu Arg Phe Trp Leu Asp Lys Gly Val Ser Gly Leu Arg Phe
225                 230                 235                 240 gat acc gtt gcc acc tac tcg aaa atc ccg aac ttc cct gac ctt agc      768
Asp Thr Val Ala Thr Tyr Ser Lys Ile Pro Asn Phe Pro Asp Leu Ser
                245                 250                 255 caa cag cag tta aaa aat ttc gcc gag gaa tat act aaa ggt cct aaa      816
Gln Gln Gln Leu Lys Asn Phe Ala Glu Glu Tyr Thr Lys Gly Pro Lys
            260                 265                 270 att cac gac tac gtg aat gaa atg aac aga gaa gta tta tcc cac tat      864
Ile His Asp Tyr Val Asn Glu Met Asn Arg Glu Val Leu Ser His Tyr
        275                 280                 285 gat atc gcc act gcg ggg gaa ata ttt ggg gtt cct ctg gat aaa tcg      912
Asp Ile Ala Thr Ala Gly Glu Ile Phe Gly Val Pro Leu Asp Lys Ser
    290                 295                 300 att aag ttt ttc gat cgc cgt aga aat gaa tta aat ata gcg ttt acg      960
Ile Lys Phe Phe Asp Arg Arg Arg Asn Glu Leu Asn Ile Ala Phe Thr
305                 310                 315                 320 ttt gat ctg atc agg ctc gat cgt gat gct gat gaa aga tgg cgg cga     1008
Phe Asp Leu Ile Arg Leu Asp Arg Asp Ala Asp Glu Arg Trp Arg Arg
                325                 330                 335 aaa gac tgg acc ctt tcg cag ttc cga aaa att gtc gat aag gtt gac     1056
Lys Asp Trp Thr Leu Ser Gln Phe Arg Lys Ile Val Asp Lys Val Asp
            340                 345                 350 caa acg gca gga gag tat ggg tgg aat gcc ttt ttc tta gac aat cac     1104
Gln Thr Ala Gly Glu Tyr Gly Trp Asn Ala Phe Phe Leu Asp Asn His
        355                 360                 365 gac aat ccc cgc gcg gtt tct cac ttt ggt gat gat cga cca caa tgg     1152
Asp Asn Pro Arg Ala Val Ser His Phe Gly Asp Asp Arg Pro Gln Trp
    370                 375                 380 cgc gag cat gcg gcg aaa gca ctg gca aca ttg acg ctg acc cag cgt     1200
Arg Glu His Ala Ala Lys Ala Leu Ala Thr Leu Thr Leu Thr Gln Arg
385                 390                 395                 400 gca acg ccg ttt atc tat cag ggt tca gaa ctc ggt atg acc aat tat     1248
Ala Thr Pro Phe Ile Tyr Gln Gly Ser Glu Leu Gly Met Thr Asn Tyr
                405                 410                 415 ccc ttt aaa aaa atc gat gat ttc gat gat gta gag gtg aaa ggt ttt     1296
Pro Phe Lys Lys Ile Asp Asp Phe Asp Asp Val Glu Val Lys Gly Phe
            420                 425                 430 tgg caa gac tac gtt gaa aca ggc aaa gtg aaa gct gag gaa ttc ctt     1344
Trp Gln Asp Tyr Val Glu Thr Gly Lys Val Lys Ala Glu Glu Phe Leu
        435                 440                 445 caa aac gta cgc caa acc agc cgt gat aac agc aga acc ccc ttc cag     1392
Gln Asn Val Arg Gln Thr Ser Arg Asp Asn Ser Arg Thr Pro Phe Gln
```

```
                                                    -continued

Gln Asn Val Arg Gln Thr Ser Arg Asp Asn Ser Arg Thr Pro Phe Gln
    450                 455                 460 tgg gat gca agc aaa aac gcg ggc ttt acc agt gga acc ccc tgg tta    1440
Trp Asp Ala Ser Lys Asn Ala Gly Phe Thr Ser Gly Thr Pro Trp Leu
465                 470                 475                 480 aaa atc aat ccc aat tat aaa gaa atc aac agc gca gat cag att aat    1488
Lys Ile Asn Pro Asn Tyr Lys Glu Ile Asn Ser Ala Asp Gln Ile Asn
                485                 490                 495 aat cca aat tcc gta ttt aac tat tat aga aag ctg att aac att cgc    1536
Asn Pro Asn Ser Val Phe Asn Tyr Tyr Arg Lys Leu Ile Asn Ile Arg
            500                 505                 510 cat gac atc cct gcc ttg acc tac ggc agt tat att gat tta gac cct    1584
His Asp Ile Pro Ala Leu Thr Tyr Gly Ser Tyr Ile Asp Leu Asp Pro
        515                 520                 525 gac aac aat tca gtc tat gct tac acc cga acg ctc ggc gct gaa aaa    1632
Asp Asn Asn Ser Val Tyr Ala Tyr Thr Arg Thr Leu Gly Ala Glu Lys
    530                 535                 540 tat ctt gtg gtc att aat ttt aaa gaa gaa gtg atg cac tac acc ctg    1680
Tyr Leu Val Val Ile Asn Phe Lys Glu Glu Val Met His Tyr Thr Leu
545                 550                 555                 560 ccc ggg gat tta tcc atc aat aag gtg att act gaa aac aac agt cac    1728
Pro Gly Asp Leu Ser Ile Asn Lys Val Ile Thr Glu Asn Asn Ser His
                565                 570                 575 act att gtg aat aaa aat gac agg caa ctc cgt ctt gaa ccc tgg cag    1776
Thr Ile Val Asn Lys Asn Asp Arg Gln Leu Arg Leu Glu Pro Trp Gln
            580                 585                 590 tcg ggc att tat aaa ctt aat ccg tag                                1803
Ser Gly Ile Tyr Lys Leu Asn Pro
        595                 600

<210> SEQ ID NO 6
<211> LENGTH: 600
<212> TYPE: PRT
<213> ORGANISM: Erwinia rhapontici

<400> SEQUENCE: 6

Met Ser Ser Gln Gly Leu Lys Thr Ala Val Ala Ile Phe Leu Ala Thr
1               5                   10                  15

Thr Phe Ser Ala Thr Ser Tyr Gln Ala Cys Ser Ala Gly Pro Asp Thr
            20                  25                  30

Ala Pro Ser Leu Thr Val Gln Gln Ser Asn Ala Leu Pro Thr Trp Trp
        35                  40                  45

Lys Gln Ala Val Phe Tyr Gln Val Tyr Pro Arg Ser Phe Lys Asp Thr
    50                  55                  60

Asn Gly Asp Gly Ile Gly Asp Leu Asn Gly Ile Ile Glu Asn Leu Asp
65                  70                  75                  80

Tyr Leu Lys Lys Leu Gly Ile Asp Ala Ile Trp Ile Asn Pro His Tyr
                85                  90                  95

Asp Ser Pro Asn Thr Asp Asn Gly Tyr Asp Ile Arg Asp Tyr Arg Lys
            100                 105                 110

Ile Met Lys Glu Tyr Gly Thr Met Glu Asp Phe Asp Arg Leu Ile Ser
        115                 120                 125

Glu Met Lys Lys Arg Asn Met Arg Leu Met Ile Asp Ile Val Ile Asn
    130                 135                 140

His Thr Ser Asp Gln His Ala Trp Phe Val Gln Ser Lys Ser Gly Lys
145                 150                 155                 160

Asn Asn Pro Tyr Arg Asp Tyr Tyr Phe Trp Arg Asp Gly Lys Asp Gly
                165                 170                 175
```

```
His Ala Pro Asn Asn Tyr Pro Ser Phe Phe Gly Gly Ser Ala Trp Glu
            180                 185                 190
Lys Asp Asp Lys Ser Gly Gln Tyr Tyr Leu His Tyr Phe Ala Lys Gln
        195                 200                 205
Gln Pro Asp Leu Asn Trp Asp Asn Pro Lys Val Arg Gln Asp Leu Tyr
    210                 215                 220
Asp Met Leu Arg Phe Trp Leu Asp Lys Gly Val Ser Gly Leu Arg Phe
225                 230                 235                 240
Asp Thr Val Ala Thr Tyr Ser Lys Ile Pro Asn Phe Pro Asp Leu Ser
                245                 250                 255
Gln Gln Gln Leu Lys Asn Phe Ala Glu Glu Tyr Thr Lys Gly Pro Lys
            260                 265                 270
Ile His Asp Tyr Val Asn Glu Met Asn Arg Glu Val Leu Ser His Tyr
        275                 280                 285
Asp Ile Ala Thr Ala Gly Glu Ile Phe Gly Val Pro Leu Asp Lys Ser
    290                 295                 300
Ile Lys Phe Phe Asp Arg Arg Arg Asn Glu Leu Asn Ile Ala Phe Thr
305                 310                 315                 320
Phe Asp Leu Ile Arg Leu Asp Arg Asp Ala Asp Glu Arg Trp Arg Arg
                325                 330                 335
Lys Asp Trp Thr Leu Ser Gln Phe Arg Lys Ile Val Asp Lys Val Asp
            340                 345                 350
Gln Thr Ala Gly Glu Tyr Gly Trp Asn Ala Phe Phe Leu Asp Asn His
        355                 360                 365
Asp Asn Pro Arg Ala Val Ser His Phe Gly Asp Asp Arg Pro Gln Trp
    370                 375                 380
Arg Glu His Ala Ala Lys Ala Leu Ala Thr Leu Thr Leu Thr Gln Arg
385                 390                 395                 400
Ala Thr Pro Phe Ile Tyr Gln Gly Ser Glu Leu Gly Met Thr Asn Tyr
                405                 410                 415
Pro Phe Lys Lys Ile Asp Asp Phe Asp Asp Val Glu Val Lys Gly Phe
            420                 425                 430
Trp Gln Asp Tyr Val Glu Thr Gly Lys Val Lys Ala Glu Glu Phe Leu
        435                 440                 445
Gln Asn Val Arg Gln Thr Ser Arg Asp Asn Ser Arg Thr Pro Phe Gln
    450                 455                 460
Trp Asp Ala Ser Lys Asn Ala Gly Phe Thr Ser Gly Thr Pro Trp Leu
465                 470                 475                 480
Lys Ile Asn Pro Asn Tyr Lys Glu Ile Asn Ser Ala Asp Gln Ile Asn
                485                 490                 495
Asn Pro Asn Ser Val Phe Asn Tyr Tyr Arg Lys Leu Ile Asn Ile Arg
            500                 505                 510
His Asp Ile Pro Ala Leu Thr Tyr Gly Ser Tyr Ile Asp Leu Asp Pro
        515                 520                 525
Asp Asn Asn Ser Val Tyr Ala Tyr Thr Arg Thr Leu Gly Ala Glu Lys
    530                 535                 540
Tyr Leu Val Val Ile Asn Phe Lys Glu Glu Val Met His Tyr Thr Leu
545                 550                 555                 560
Pro Gly Asp Leu Ser Ile Asn Lys Val Ile Thr Glu Asn Asn Ser His
                565                 570                 575
Thr Ile Val Asn Lys Asn Asp Arg Gln Leu Arg Leu Glu Pro Trp Gln
            580                 585                 590
```

```
                Ser Gly Ile Tyr Lys Leu Asn Pro
                        595             600

<210> SEQ ID NO 7
<211> LENGTH: 1803
<212> TYPE: DNA
<213> ORGANISM: Protaminobacter rubrum
<220> FEATURE:
<221> NAME/KEY: CDS
<222> LOCATION: (1)..(1800)
<223> OTHER INFORMATION: coding for sucrose isomerase

<400> SEQUENCE: 7 atg ccc cgt caa gga ttg aaa act gca cta gcg att ttt cta acc aca      48
Met Pro Arg Gln Gly Leu Lys Thr Ala Leu Ala Ile Phe Leu Thr Thr
1               5                   10                  15 tca tta tgc atc tca tgc cag caa gcc ttc ggt acg caa caa ccc ttg      96
Ser Leu Cys Ile Ser Cys Gln Gln Ala Phe Gly Thr Gln Gln Pro Leu
            20                  25                  30 ctt aac gaa aag agt atc gaa cag tcg aaa acc ata cct aaa tgg tgg     144
Leu Asn Glu Lys Ser Ile Glu Gln Ser Lys Thr Ile Pro Lys Trp Trp
        35                  40                  45 aag gag gct gtt ttt tat cag gtg tat ccg cgc tcc ttt aaa gac acc     192
Lys Glu Ala Val Phe Tyr Gln Val Tyr Pro Arg Ser Phe Lys Asp Thr
    50                  55                  60 aac gga gat ggc atc ggg gat att aac ggc atc ata gaa aaa tta gac     240
Asn Gly Asp Gly Ile Gly Asp Ile Asn Gly Ile Ile Glu Lys Leu Asp
65                  70                  75                  80 tat cta aaa gcc ttg ggg att gat gcc att tgg atc aac cca cat tat     288
Tyr Leu Lys Ala Leu Gly Ile Asp Ala Ile Trp Ile Asn Pro His Tyr
                85                  90                  95 gat tct ccg aac acg gat aat ggt tac gat ata cgt gat tat cga aaa     336
Asp Ser Pro Asn Thr Asp Asn Gly Tyr Asp Ile Arg Asp Tyr Arg Lys
            100                 105                 110 atc atg aaa gaa tat ggc acg atg gag gat ttt gac cgc ctg att tct     384
Ile Met Lys Glu Tyr Gly Thr Met Glu Asp Phe Asp Arg Leu Ile Ser
        115                 120                 125 gaa atg aaa aaa cgg aat atg cgg ttg atg att gat gtg gtc atc aac     432
Glu Met Lys Lys Arg Asn Met Arg Leu Met Ile Asp Val Val Ile Asn
    130                 135                 140 cac acc agc gat caa aac gaa tgg ttt gtt aaa agt aaa agc agt aag     480
His Thr Ser Asp Gln Asn Glu Trp Phe Val Lys Ser Lys Ser Ser Lys
145                 150                 155                 160 gat aat cct tat cgc ggc tat tat ttc tgg aaa gat gct aaa gaa ggg     528
Asp Asn Pro Tyr Arg Gly Tyr Tyr Phe Trp Lys Asp Ala Lys Glu Gly
                165                 170                 175 cag gcg cct aat aat tac cct tca ttc ttt ggt ggc tcg gcg tgg caa     576
Gln Ala Pro Asn Asn Tyr Pro Ser Phe Phe Gly Gly Ser Ala Trp Gln
            180                 185                 190 aaa gat gaa aag acc aat caa tac tac ctg cac tat ttt gct aaa caa     624
Lys Asp Glu Lys Thr Asn Gln Tyr Tyr Leu His Tyr Phe Ala Lys Gln
        195                 200                 205 cag cct gac cta aac tgg gat aat ccc aaa gtc cgt caa gat ctt tat     672
Gln Pro Asp Leu Asn Trp Asp Asn Pro Lys Val Arg Gln Asp Leu Tyr
    210                 215                 220 gca atg tta cgt ttc tgg tta gat aaa ggc gtg tct ggt tta cgt ttt     720
Ala Met Leu Arg Phe Trp Leu Asp Lys Gly Val Ser Gly Leu Arg Phe
225                 230                 235                 240 gat acg gta gcg acc tac tca aaa att ccg gat ttc cca aat ctc acc     768
Asp Thr Val Ala Thr Tyr Ser Lys Ile Pro Asp Phe Pro Asn Leu Thr
                245                 250                 255
```

```
caa caa cag ctg aag aat ttt gca gcg gag tat acc aag ggc cct aat    816
Gln Gln Gln Leu Lys Asn Phe Ala Ala Glu Tyr Thr Lys Gly Pro Asn
            260                 265                 270 att cat cgt tac gtc aat gaa atg aat aaa gag gtc ttg tct cat tac    864
Ile His Arg Tyr Val Asn Glu Met Asn Lys Glu Val Leu Ser His Tyr
        275                 280                 285 gac att gcg act gcc ggt gaa atc ttt ggc gta ccc ttg gat caa tcg    912
Asp Ile Ala Thr Ala Gly Glu Ile Phe Gly Val Pro Leu Asp Gln Ser
    290                 295                 300 ata aag ttc ttc gat cgc cgc cgt gat gag ctg aac att gca ttt acc    960
Ile Lys Phe Phe Asp Arg Arg Arg Asp Glu Leu Asn Ile Ala Phe Thr
305                 310                 315                 320 ttt gac tta atc aga ctc gat cga gac tct gat caa aga tgg cgt cga   1008
Phe Asp Leu Ile Arg Leu Asp Arg Asp Ser Asp Gln Arg Trp Arg Arg
                325                 330                 335 aaa gat tgg aaa ttg tcg caa ttc cgg cag atc atc gat aac gtt gac   1056
Lys Asp Trp Lys Leu Ser Gln Phe Arg Gln Ile Ile Asp Asn Val Asp
            340                 345                 350 cgt act gca gga gaa tat ggt tgg aat gcc ttc ttc ttg gat aac cac   1104
Arg Thr Ala Gly Glu Tyr Gly Trp Asn Ala Phe Phe Leu Asp Asn His
        355                 360                 365 gac aat ccg cgc gct gtc tcg cac ttt ggc gat gat cgc cca caa tgg   1152
Asp Asn Pro Arg Ala Val Ser His Phe Gly Asp Asp Arg Pro Gln Trp
    370                 375                 380 cgt gag cca tcg gct aaa gcg ctt gca acc ttg acg ctg act caa cga   1200
Arg Glu Pro Ser Ala Lys Ala Leu Ala Thr Leu Thr Leu Thr Gln Arg
385                 390                 395                 400 gca aca cct ttt att tat caa ggt tca gaa ttg ggc atg acc aat tac   1248
Ala Thr Pro Phe Ile Tyr Gln Gly Ser Glu Leu Gly Met Thr Asn Tyr
                405                 410                 415 ccg ttt aaa gct att gat gaa ttc gat gat att gag gtg aaa ggt ttt   1296
Pro Phe Lys Ala Ile Asp Glu Phe Asp Asp Ile Glu Val Lys Gly Phe
            420                 425                 430 tgg cat gac tac gtt gag aca gga aag gtc aaa gcc gac gag ttc ttg   1344
Trp His Asp Tyr Val Glu Thr Gly Lys Val Lys Ala Asp Glu Phe Leu
        435                 440                 445 caa aat gta cgc ctg acg agc agg gat aac agc cgg acg ccg ttc caa   1392
Gln Asn Val Arg Leu Thr Ser Arg Asp Asn Ser Arg Thr Pro Phe Gln
    450                 455                 460 tgg gat ggg agc aaa aat gca gga ttc acg agc gga aaa cct tgg ttc   1440
Trp Asp Gly Ser Lys Asn Ala Gly Phe Thr Ser Gly Lys Pro Trp Phe
465                 470                 475                 480 aag gtc aac cca aac tac cag gaa atc aat gca gta agt caa gtc aca   1488
Lys Val Asn Pro Asn Tyr Gln Glu Ile Asn Ala Val Ser Gln Val Thr
                485                 490                 495 caa ccc gac tca gta ttt aac tat tat cgt cag ttg atc aag ata agg   1536
Gln Pro Asp Ser Val Phe Asn Tyr Tyr Arg Gln Leu Ile Lys Ile Arg
            500                 505                 510 cat gac atc ccg gca ctg acc tat ggt aca tac acc gat ttg gat cct   1584
His Asp Ile Pro Ala Leu Thr Tyr Gly Thr Tyr Thr Asp Leu Asp Pro
        515                 520                 525 gca aat gat tcg gtc tac gcc tat aca cgc agc ctt ggg gcg gaa aaa   1632
Ala Asn Asp Ser Val Tyr Ala Tyr Thr Arg Ser Leu Gly Ala Glu Lys
    530                 535                 540 tat ctt gtt gtt gtt aac ttc aag gag caa atg atg aga tat aaa tta   1680
Tyr Leu Val Val Val Asn Phe Lys Glu Gln Met Met Arg Tyr Lys Leu
545                 550                 555                 560 ccg gat aat tta tcc att gag aaa gtg att ata gac agc aac agc aaa   1728
Pro Asp Asn Leu Ser Ile Glu Lys Val Ile Ile Asp Ser Asn Ser Lys
                565                 570                 575
```

```
aac gtg gtg aaa aag aat gat tca tta ctc gag cta aaa cca tgg cag      1776
Asn Val Val Lys Lys Asn Asp Ser Leu Leu Glu Leu Lys Pro Trp Gln
        580                 585                 590 tca ggg gtt tat aaa cta aat caa taa                                  1803
Ser Gly Val Tyr Lys Leu Asn Gln
        595                 600

<210> SEQ ID NO 8
<211> LENGTH: 600
<212> TYPE: PRT
<213> ORGANISM: Protaminobacter rubrum

<400> SEQUENCE: 8

Met Pro Arg Gln Gly Leu Lys Thr Ala Leu Ala Ile Phe Leu Thr Thr
 1               5                  10                  15

Ser Leu Cys Ile Ser Cys Gln Gln Ala Phe Gly Thr Gln Gln Pro Leu
                20                  25                  30

Leu Asn Glu Lys Ser Ile Glu Gln Ser Lys Thr Ile Pro Lys Trp Trp
            35                  40                  45

Lys Glu Ala Val Phe Tyr Gln Val Tyr Pro Arg Ser Phe Lys Asp Thr
        50                  55                  60

Asn Gly Asp Gly Ile Gly Asp Ile Asn Gly Ile Ile Glu Lys Leu Asp
 65                  70                  75                  80

Tyr Leu Lys Ala Leu Gly Ile Asp Ala Ile Trp Ile Asn Pro His Tyr
                85                  90                  95

Asp Ser Pro Asn Thr Asp Asn Gly Tyr Asp Ile Arg Asp Tyr Arg Lys
            100                 105                 110

Ile Met Lys Glu Tyr Gly Thr Met Glu Asp Phe Asp Arg Leu Ile Ser
        115                 120                 125

Glu Met Lys Lys Arg Asn Met Arg Leu Met Ile Asp Val Val Ile Asn
    130                 135                 140

His Thr Ser Asp Gln Asn Glu Trp Phe Val Lys Ser Lys Ser Ser Lys
145                 150                 155                 160

Asp Asn Pro Tyr Arg Gly Tyr Tyr Phe Trp Lys Asp Ala Lys Glu Gly
                165                 170                 175

Gln Ala Pro Asn Asn Tyr Pro Ser Phe Phe Gly Gly Ser Ala Trp Gln
            180                 185                 190

Lys Asp Glu Lys Thr Asn Gln Tyr Tyr Leu His Tyr Phe Ala Lys Gln
        195                 200                 205

Gln Pro Asp Leu Asn Trp Asp Asn Pro Lys Val Arg Gln Asp Leu Tyr
    210                 215                 220

Ala Met Leu Arg Phe Trp Leu Asp Lys Gly Val Ser Gly Leu Arg Phe
225                 230                 235                 240

Asp Thr Val Ala Thr Tyr Ser Lys Ile Pro Asp Phe Pro Asn Leu Thr
                245                 250                 255

Gln Gln Gln Leu Lys Asn Phe Ala Ala Glu Tyr Thr Lys Gly Pro Asn
            260                 265                 270

Ile His Arg Tyr Val Asn Glu Met Asn Lys Glu Val Leu Ser His Tyr
        275                 280                 285

Asp Ile Ala Thr Ala Gly Glu Ile Phe Gly Val Pro Leu Asp Gln Ser
    290                 295                 300

Ile Lys Phe Phe Asp Arg Arg Asp Glu Leu Asn Ile Ala Phe Thr
305                 310                 315                 320

Phe Asp Leu Ile Arg Leu Asp Arg Asp Ser Asp Gln Arg Trp Arg Arg
                325                 330                 335
```

```
Lys Asp Trp Lys Leu Ser Gln Phe Arg Gln Ile Ile Asp Asn Val Asp
            340                 345                 350

Arg Thr Ala Gly Glu Tyr Gly Trp Asn Ala Phe Phe Leu Asp Asn His
            355                 360                 365

Asp Asn Pro Arg Ala Val Ser His Phe Gly Asp Asp Arg Pro Gln Trp
            370                 375                 380

Arg Glu Pro Ser Ala Lys Ala Leu Ala Thr Leu Thr Leu Thr Gln Arg
385                 390                 395                 400

Ala Thr Pro Phe Ile Tyr Gln Gly Ser Glu Leu Gly Met Thr Asn Tyr
                405                 410                 415

Pro Phe Lys Ala Ile Asp Glu Phe Asp Asp Ile Glu Val Lys Gly Phe
            420                 425                 430

Trp His Asp Tyr Val Glu Thr Gly Lys Val Lys Ala Asp Glu Phe Leu
            435                 440                 445

Gln Asn Val Arg Leu Thr Ser Arg Asp Asn Ser Arg Thr Pro Phe Gln
            450                 455                 460

Trp Asp Gly Ser Lys Asn Ala Gly Phe Thr Ser Gly Lys Pro Trp Phe
465                 470                 475                 480

Lys Val Asn Pro Asn Tyr Gln Glu Ile Asn Ala Val Ser Gln Val Thr
                485                 490                 495

Gln Pro Asp Ser Val Phe Asn Tyr Tyr Arg Gln Leu Ile Lys Ile Arg
            500                 505                 510

His Asp Ile Pro Ala Leu Thr Tyr Gly Thr Tyr Thr Asp Leu Asp Pro
            515                 520                 525

Ala Asn Asp Ser Val Tyr Ala Tyr Thr Arg Ser Leu Gly Ala Glu Lys
            530                 535                 540

Tyr Leu Val Val Val Asn Phe Lys Glu Gln Met Met Arg Tyr Lys Leu
545                 550                 555                 560

Pro Asp Asn Leu Ser Ile Glu Lys Val Ile Ile Asp Ser Asn Ser Lys
                565                 570                 575

Asn Val Val Lys Lys Asn Asp Ser Leu Leu Glu Leu Lys Pro Trp Gln
            580                 585                 590

Ser Gly Val Tyr Lys Leu Asn Gln
            595                 600

<210> SEQ ID NO 9
<211> LENGTH: 1794
<212> TYPE: DNA
<213> ORGANISM: Enterobacter sp.
<220> FEATURE:
<221> NAME/KEY: CDS
<222> LOCATION: (1)..(1791)
<223> OTHER INFORMATION: coding for sucrose isomerase

<400> SEQUENCE: 9 atg tct ttt gtt acg cta cgt acc ggg gtg gct gtc gcg ctg tca tct    48
Met Ser Phe Val Thr Leu Arg Thr Gly Val Ala Val Ala Leu Ser Ser
  1               5                  10                  15 ttg ata ata agt ctg gcc tgc ccg gct gtc agt gct gca cca tcc ttg    96
Leu Ile Ile Ser Leu Ala Cys Pro Ala Val Ser Ala Ala Pro Ser Leu
             20                  25                  30 aat cag gat att cac gtt caa aag gaa agt gaa tat cct gca tgg tgg   144
Asn Gln Asp Ile His Val Gln Lys Glu Ser Glu Tyr Pro Ala Trp Trp
         35                  40                  45 aaa gaa gct gtt ttt tat cag atc tat cct cgc tca ttt aaa gac acc   192
Lys Glu Ala Val Phe Tyr Gln Ile Tyr Pro Arg Ser Phe Lys Asp Thr
     50                  55                  60
```

```
aat gat gat ggc att ggc gat att cgc ggt att att gaa aag ctg gac        240
Asn Asp Asp Gly Ile Gly Asp Ile Arg Gly Ile Ile Glu Lys Leu Asp
 65                  70                  75                  80 tat ctg aaa tcg ctc ggt att gac gct atc tgg atc aat ccc cat tac        288
Tyr Leu Lys Ser Leu Gly Ile Asp Ala Ile Trp Ile Asn Pro His Tyr
                 85                  90                  95 gac tct ccg aac acc gat aac ggc tat gac atc agt aat tat cgt cag        336
Asp Ser Pro Asn Thr Asp Asn Gly Tyr Asp Ile Ser Asn Tyr Arg Gln
            100                 105                 110 ata atg aaa gag tat ggc aca atg gag gat ttt gat agc ctt gtt gcc        384
Ile Met Lys Glu Tyr Gly Thr Met Glu Asp Phe Asp Ser Leu Val Ala
        115                 120                 125 gaa atg aaa aaa cga aat atg cgc tta atg atc gac gtg gtc att aac        432
Glu Met Lys Lys Arg Asn Met Arg Leu Met Ile Asp Val Val Ile Asn
130                 135                 140 cat acc agt gat caa cac ccg tgg ttt att cag agt aaa agc gat aaa        480
His Thr Ser Asp Gln His Pro Trp Phe Ile Gln Ser Lys Ser Asp Lys
145                 150                 155                 160 aac aac cct tat cgt gac tat tat ttc tgg cgt gac gga aaa gat aat        528
Asn Asn Pro Tyr Arg Asp Tyr Tyr Phe Trp Arg Asp Gly Lys Asp Asn
                165                 170                 175 cag cca cct aat aat tac ccc tca ttt ttc ggc ggc tcg gca tgg caa        576
Gln Pro Pro Asn Asn Tyr Pro Ser Phe Phe Gly Gly Ser Ala Trp Gln
            180                 185                 190 aaa gat gca aag tca gga cag tac tat tta cac tat ttt gcc aga cag        624
Lys Asp Ala Lys Ser Gly Gln Tyr Tyr Leu His Tyr Phe Ala Arg Gln
        195                 200                 205 caa cct gat ctc aac tgg gat aac ccg aaa gta cgt gag gat ctt tac        672
Gln Pro Asp Leu Asn Trp Asp Asn Pro Lys Val Arg Glu Asp Leu Tyr
210                 215                 220 gca atg ctc cgc ttc tgg ctg gat aaa ggc gtt tca ggc atg cga ttt        720
Ala Met Leu Arg Phe Trp Leu Asp Lys Gly Val Ser Gly Met Arg Phe
225                 230                 235                 240 gat acg gtg gca act tat tcc aaa atc ccg gga ttt ccc aat ctg aca        768
Asp Thr Val Ala Thr Tyr Ser Lys Ile Pro Gly Phe Pro Asn Leu Thr
                245                 250                 255 cct gaa caa cag aaa aat ttt gct gaa caa tac acc atg ggd cct aat        816
Pro Glu Gln Gln Lys Asn Phe Ala Glu Gln Tyr Thr Met Xaa Pro Asn
            260                 265                 270 att cat cga tac att cag gaa atg aac cgg aaa gtt ctg tcc cgg tat        864
Ile His Arg Tyr Ile Gln Glu Met Asn Arg Lys Val Leu Ser Arg Tyr
        275                 280                 285 gat gtg gcc acc gcg ggt gaa att ttt ggc gtc ccg ctg gat cgt tcg        912
Asp Val Ala Thr Ala Gly Glu Ile Phe Gly Val Pro Leu Asp Arg Ser
290                 295                 300 tcg cag ttt ttt gat cgc cgc cga cat gag ctg aat atg gcg ttt atg        960
Ser Gln Phe Phe Asp Arg Arg Arg His Glu Leu Asn Met Ala Phe Met
305                 310                 315                 320 ttt gac ctc att cgt ctc gat cgc gac agc aat gaa cgc tgg cgt cac       1008
Phe Asp Leu Ile Arg Leu Asp Arg Asp Ser Asn Glu Arg Trp Arg His
                325                 330                 335 aag tcg tgg tcg ctc tct cag ttc cgc cag atc atc agc aaa atg gat       1056
Lys Ser Trp Ser Leu Ser Gln Phe Arg Gln Ile Ile Ser Lys Met Asp
            340                 345                 350 gtc acg gtc gga aag tat ggc tgg aac acg ttc ttc tta gac aac cat       1104
Val Thr Val Gly Lys Tyr Gly Trp Asn Thr Phe Phe Leu Asp Asn His
        355                 360                 365 gac aac ccc cgt gcg gta tct cac ttc ggg gat gac agg ccg caa tgg       1152
Asp Asn Pro Arg Ala Val Ser His Phe Gly Asp Asp Arg Pro Gln Trp
```

|  |  |
|---|---|
| cgg gag gcg tcg gct aag gca ctg gcg acg att acc ctc act cag cgg<br>Arg Glu Ala Ser Ala Lys Ala Leu Ala Thr Ile Thr Leu Thr Gln Arg<br>385                     390                     395                     400 | 1200 |
| gcg acg ccg ttt att tat cag ggt tca gag ctg gga atg act aat tat<br>Ala Thr Pro Phe Ile Tyr Gln Gly Ser Glu Leu Gly Met Thr Asn Tyr<br>                     405                     410                     415 | 1248 |
| ccc ttc agg caa ctc aac gaa ttt gac gac atc gag gtc aaa ggt ttc<br>Pro Phe Arg Gln Leu Asn Glu Phe Asp Asp Ile Glu Val Lys Gly Phe<br>               420                     425                     430 | 1296 |
| tgg cag gat tat gtc cag agt gga aaa gtc acg gcc aca gag ttt ctc<br>Trp Gln Asp Tyr Val Gln Ser Gly Lys Val Thr Ala Thr Glu Phe Leu<br>435                     440                     445 | 1344 |
| gat aat gtg cgc ctg acg agc cgc gat aac agc aga aca cct ttc cag<br>Asp Asn Val Arg Leu Thr Ser Arg Asp Asn Ser Arg Thr Pro Phe Gln<br>               450                     455                     460 | 1392 |
| tgg aat gac acc ctg aat gct ggt ttt act cgc gga aag ccg tgg ttt<br>Trp Asn Asp Thr Leu Asn Ala Gly Phe Thr Arg Gly Lys Pro Trp Phe<br>465                     470                     475                     480 | 1440 |
| cac atc aac cca aac tat gtg gag atc aac scc gaa cgc gaa gaa acc<br>His Ile Asn Pro Asn Tyr Val Glu Ile Asn Xaa Glu Arg Glu Glu Thr<br>               485                     490                     495 | 1488 |
| cgc gaa gat tca gtg ctg aat tac tat aaa aaa atg att cag cta cgc<br>Arg Glu Asp Ser Val Leu Asn Tyr Tyr Lys Lys Met Ile Gln Leu Arg<br>500                     505                     510 | 1536 |
| cac cat atc cct gct ctg gta tat ggc gcc tat cag gat ctt aat cca<br>His His Ile Pro Ala Leu Val Tyr Gly Ala Tyr Gln Asp Leu Asn Pro<br>               515                     520                     525 | 1584 |
| cag gac aat acc gtt tat gcc tat acc cga acg ctg ggt aac gag cgt<br>Gln Asp Asn Thr Val Tyr Ala Tyr Thr Arg Thr Leu Gly Asn Glu Arg<br>530                     535                     540 | 1632 |
| tat ctg gtc gtg gtg aac ttt aag gag tac ccg gtc cgc tat act ctc<br>Tyr Leu Val Val Val Asn Phe Lys Glu Tyr Pro Val Arg Tyr Thr Leu<br>545                     550                     555                     560 | 1680 |
| ccg gct aat gat gcc atc gag gaa gtg gtc att gat act cag cag caa<br>Pro Ala Asn Asp Ala Ile Glu Glu Val Val Ile Asp Thr Gln Gln Gln<br>               565                     570                     575 | 1728 |
| ggt gcg ccg cac agc aca tcc ctg tca ttg agc ccc tgg cag gca ggt<br>Gly Ala Pro His Ser Thr Ser Leu Ser Leu Ser Pro Trp Gln Ala Gly<br>580                     585                     590 | 1776 |
| gcg tat aag ctg cgg taa<br>Ala Tyr Lys Leu Arg<br>               595 | 1794 |

<210> SEQ ID NO 10
<211> LENGTH: 597
<212> TYPE: PRT
<213> ORGANISM: Enterobacter sp.
<220> FEATURE:
<221> NAME/KEY: misc_feature
<222> LOCATION: (270)..(270)
<223> OTHER INFORMATION: The 'Xaa' at location 270 stands for Gly.
<220> FEATURE:
<221> NAME/KEY: misc_feature
<222> LOCATION: (491)..(491)
<223> OTHER INFORMATION: The 'Xaa' at location 491 stands for Ala, or Pro.

<400> SEQUENCE: 10

Met Ser Phe Val Thr Leu Arg Thr Gly Val Ala Val Ala Leu Ser Ser
1                 5                 10                 15

Leu Ile Ile Ser Leu Ala Cys Pro Ala Val Ser Ala Ala Pro Ser Leu

-continued

```
                20                  25                  30
Asn Gln Asp Ile His Val Gln Lys Glu Ser Glu Tyr Pro Ala Trp Trp
            35                  40                  45
Lys Glu Ala Val Phe Tyr Gln Ile Tyr Pro Arg Ser Phe Lys Asp Thr
        50                  55                  60
Asn Asp Asp Gly Ile Gly Asp Ile Arg Gly Ile Ile Glu Lys Leu Asp
65                  70                  75                  80
Tyr Leu Lys Ser Leu Gly Ile Asp Ala Ile Trp Ile Asn Pro His Tyr
                85                  90                  95
Asp Ser Pro Asn Thr Asp Asn Gly Tyr Asp Ile Ser Asn Tyr Arg Gln
            100                 105                 110
Ile Met Lys Glu Tyr Gly Thr Met Glu Asp Phe Asp Ser Leu Val Ala
        115                 120                 125
Glu Met Lys Lys Arg Asn Met Arg Leu Met Ile Asp Val Val Ile Asn
130                 135                 140
His Thr Ser Asp Gln His Pro Trp Phe Ile Gln Ser Lys Ser Asp Lys
145                 150                 155                 160
Asn Asn Pro Tyr Arg Asp Tyr Tyr Phe Trp Arg Asp Gly Lys Asp Asn
                165                 170                 175
Gln Pro Pro Asn Asn Tyr Pro Ser Phe Phe Gly Gly Ser Ala Trp Gln
            180                 185                 190
Lys Asp Ala Lys Ser Gly Gln Tyr Tyr Leu His Tyr Phe Ala Arg Gln
        195                 200                 205
Gln Pro Asp Leu Asn Trp Asp Asn Pro Lys Val Arg Glu Asp Leu Tyr
    210                 215                 220
Ala Met Leu Arg Phe Trp Leu Asp Lys Gly Val Ser Gly Met Arg Phe
225                 230                 235                 240
Asp Thr Val Ala Thr Tyr Ser Lys Ile Pro Gly Phe Pro Asn Leu Thr
                245                 250                 255
Pro Glu Gln Gln Lys Asn Phe Ala Glu Gln Tyr Thr Met Xaa Pro Asn
            260                 265                 270
Ile His Arg Tyr Ile Gln Glu Met Asn Arg Lys Val Leu Ser Arg Tyr
        275                 280                 285
Asp Val Ala Thr Ala Gly Glu Ile Phe Gly Val Pro Leu Asp Arg Ser
    290                 295                 300
Ser Gln Phe Phe Asp Arg Arg Arg His Glu Leu Asn Met Ala Phe Met
305                 310                 315                 320
Phe Asp Leu Ile Arg Leu Asp Arg Asp Ser Asn Glu Arg Trp Arg His
                325                 330                 335
Lys Ser Trp Ser Leu Ser Gln Phe Arg Gln Ile Ile Ser Lys Met Asp
            340                 345                 350
Val Thr Val Gly Lys Tyr Gly Trp Asn Thr Phe Phe Leu Asp Asn His
        355                 360                 365
Asp Asn Pro Arg Ala Val Ser His Phe Gly Asp Asp Arg Pro Gln Trp
    370                 375                 380
Arg Glu Ala Ser Ala Lys Ala Leu Ala Thr Ile Thr Leu Thr Gln Arg
385                 390                 395                 400
Ala Thr Pro Phe Ile Tyr Gln Gly Ser Glu Leu Gly Met Thr Asn Tyr
                405                 410                 415
Pro Phe Arg Gln Leu Asn Glu Phe Asp Asp Ile Glu Val Lys Gly Phe
            420                 425                 430
Trp Gln Asp Tyr Val Gln Ser Gly Lys Val Thr Ala Thr Glu Phe Leu
        435                 440                 445
```

```
Asp Asn Val Arg Leu Thr Ser Arg Asp Asn Ser Arg Thr Pro Phe Gln
    450                 455                 460

Trp Asn Asp Thr Leu Asn Ala Gly Phe Thr Arg Gly Lys Pro Trp Phe
465                 470                 475                 480

His Ile Asn Pro Asn Tyr Val Glu Ile Asn Xaa Glu Arg Glu Glu Thr
                485                 490                 495

Arg Glu Asp Ser Val Leu Asn Tyr Tyr Lys Lys Met Ile Gln Leu Arg
            500                 505                 510

His His Ile Pro Ala Leu Val Tyr Gly Ala Tyr Gln Asp Leu Asn Pro
        515                 520                 525

Gln Asp Asn Thr Val Tyr Ala Tyr Thr Arg Thr Leu Gly Asn Glu Arg
    530                 535                 540

Tyr Leu Val Val Val Asn Phe Lys Glu Tyr Pro Val Arg Tyr Thr Leu
545                 550                 555                 560

Pro Ala Asn Asp Ala Ile Glu Glu Val Val Ile Asp Thr Gln Gln Gln
                565                 570                 575

Gly Ala Pro His Ser Thr Ser Leu Ser Leu Ser Pro Trp Gln Ala Gly
            580                 585                 590

Ala Tyr Lys Leu Arg
        595
```

```
<210> SEQ ID NO 11
<211> LENGTH: 1803
<212> TYPE: DNA
<213> ORGANISM: Serratia plymuthica
<220> FEATURE:
<221> NAME/KEY: CDS
<222> LOCATION: (1)..(1800)
<223> OTHER INFORMATION: coding for sucrose isomerase

<400> SEQUENCE: 11
```

```
atg ccc cgt caa gga ttg aaa act gca cta gcg att ttt cta acc aca    48
Met Pro Arg Gln Gly Leu Lys Thr Ala Leu Ala Ile Phe Leu Thr Thr
  1               5                  10                  15 tca tta agc gtc tca tgc cag caa gcc tta ggt acg caa caa ccc ttg    96
Ser Leu Ser Val Ser Cys Gln Gln Ala Leu Gly Thr Gln Gln Pro Leu
             20                  25                  30 ctt aac gaa aag agt atc gaa cag tcg aaa acc ata cct aaa tgg tgg   144
Leu Asn Glu Lys Ser Ile Glu Gln Ser Lys Thr Ile Pro Lys Trp Trp
         35                  40                  45 aag gag gct gtt ttt tat cag gtg tat ccg cgt tcc ttt aaa gac act   192
Lys Glu Ala Val Phe Tyr Gln Val Tyr Pro Arg Ser Phe Lys Asp Thr
 50                  55                  60 aac ggg gat ggt atc ggg gat att aaa ggc atc ata gaa aaa tta gac   240
Asn Gly Asp Gly Ile Gly Asp Ile Lys Gly Ile Ile Glu Lys Leu Asp
 65                  70                  75                  80 tat tta aaa gct ttg ggg att gat gcc att tgg atc aac cca cat tat   288
Tyr Leu Lys Ala Leu Gly Ile Asp Ala Ile Trp Ile Asn Pro His Tyr
                 85                  90                  95 gac tcc ccg aac acg gat aat ggt tac gat ata cgt gat tat cga aaa   336
Asp Ser Pro Asn Thr Asp Asn Gly Tyr Asp Ile Arg Asp Tyr Arg Lys
            100                 105                 110 atc atg aaa gaa tat ggc acg atg gag gat ttt gac cgc ctg att tct   384
Ile Met Lys Glu Tyr Gly Thr Met Glu Asp Phe Asp Arg Leu Ile Ser
        115                 120                 125 gaa atg aaa aaa cgt aac atg cgg ttg atg att gat gtg gtc atc aac   432
Glu Met Lys Lys Arg Asn Met Arg Leu Met Ile Asp Val Val Ile Asn
    130                 135                 140
```

-continued

| | |
|---|---|
| cac acc agc gat caa aac gaa tgg ttt gtt aaa agt aaa agc agt aag<br>His Thr Ser Asp Gln Asn Glu Trp Phe Val Lys Ser Lys Ser Ser Lys<br>145                      150                      155                      160 | 480 |
| gat aat cct tat cgt ggc tat tac ttc tgg aaa gat gct aaa gaa ggg<br>Asp Asn Pro Tyr Arg Gly Tyr Tyr Phe Trp Lys Asp Ala Lys Glu Gly<br>                      165                      170                      175 | 528 |
| cag gcg cct aat aat tac cct tca ttc ttt ggt ggc tcg gcg tgg caa<br>Gln Ala Pro Asn Asn Tyr Pro Ser Phe Phe Gly Gly Ser Ala Trp Gln<br>            180                      185                      190 | 576 |
| aaa gat gaa aag acc aat caa tac tac ctg cac tat ttt gct aaa caa<br>Lys Asp Glu Lys Thr Asn Gln Tyr Tyr Leu His Tyr Phe Ala Lys Gln<br>                195                      200                      205 | 624 |
| cag cct gac cta aac tgg gat aac ccc aaa gtc cgt caa gat ctt tat<br>Gln Pro Asp Leu Asn Trp Asp Asn Pro Lys Val Arg Gln Asp Leu Tyr<br>210                      215                      220 | 672 |
| gca atg ttg cgt ttc tgg tta gat aaa ggc gtg tct ggt tta cgc ttt<br>Ala Met Leu Arg Phe Trp Leu Asp Lys Gly Val Ser Gly Leu Arg Phe<br>225                      230                      235                      240 | 720 |
| gat acg gta gcg acc tac tca aaa att ccg gac ttc cca aat ctc acc<br>Asp Thr Val Ala Thr Tyr Ser Lys Ile Pro Asp Phe Pro Asn Leu Thr<br>                      245                      250                      255 | 768 |
| caa caa cag ctg aag aat ttt gca gct gag tat acc aag ggc cct aat<br>Gln Gln Gln Leu Lys Asn Phe Ala Ala Glu Tyr Thr Lys Gly Pro Asn<br>            260                      265                      270 | 816 |
| att cat cgt tac gtc aat gaa atg aat aga gaa gtt ttg tct cat tac<br>Ile His Arg Tyr Val Asn Glu Met Asn Arg Glu Val Leu Ser His Tyr<br>                275                      280                      285 | 864 |
| gac att gcc act gcc ggt gaa atc ttt ggc gta ccc ttg gat caa tcg<br>Asp Ile Ala Thr Ala Gly Glu Ile Phe Gly Val Pro Leu Asp Gln Ser<br>290                      295                      300 | 912 |
| ata aaa ttc ttc gat cgc cgt cgc gat gag ctg aac atc gca ttt acc<br>Ile Lys Phe Phe Asp Arg Arg Arg Asp Glu Leu Asn Ile Ala Phe Thr<br>305                      310                      315                      320 | 960 |
| ttt gac tta atc aga ctc gat cga gac tct gat caa aga tgg cgt cga<br>Phe Asp Leu Ile Arg Leu Asp Arg Asp Ser Asp Gln Arg Trp Arg Arg<br>                      325                      330                      335 | 1008 |
| aaa gag tgg aaa ttg tcg caa ttc cga cag gtc atc gat aac gtt gac<br>Lys Glu Trp Lys Leu Ser Gln Phe Arg Gln Val Ile Asp Asn Val Asp<br>            340                      345                      350 | 1056 |
| cgt act gcc ggc gaa tat ggt tgg aat gcc ttc ttc ttg gat aac cac<br>Arg Thr Ala Gly Glu Tyr Gly Trp Asn Ala Phe Phe Leu Asp Asn His<br>                355                      360                      365 | 1104 |
| gac aat ccg cgc gct gtc tcc cac ttt ggc gat gat cgc cca caa tgg<br>Asp Asn Pro Arg Ala Val Ser His Phe Gly Asp Asp Arg Pro Gln Trp<br>370                      375                      380 | 1152 |
| cgc gag cca tcg gct aaa gcg ctt gca acc ttg acg ctg act caa cga<br>Arg Glu Pro Ser Ala Lys Ala Leu Ala Thr Leu Thr Leu Thr Gln Arg<br>385                      390                      395                      400 | 1200 |
| gca acg cct ttt att tat caa ggt tca gaa ttg ggc atg acc aat tac<br>Ala Thr Pro Phe Ile Tyr Gln Gly Ser Glu Leu Gly Met Thr Asn Tyr<br>                405                      410                      415 | 1248 |
| ccc ttc aaa gct att gat gaa ttc gat gat att gag gtg aaa ggt ttt<br>Pro Phe Lys Ala Ile Asp Glu Phe Asp Asp Ile Glu Val Lys Gly Phe<br>            420                      425                      430 | 1296 |
| tgg cat gac tac gtt gag aca gga aag gtg aaa gcc gac gag ttc ttg<br>Trp His Asp Tyr Val Glu Thr Gly Lys Val Lys Ala Asp Glu Phe Leu<br>                435                      440                      445 | 1344 |
| caa aat gta cgc ctg acg agc agg gat aac agc cgg aca ccg ttc caa<br>Gln Asn Val Arg Leu Thr Ser Arg Asp Asn Ser Arg Thr Pro Phe Gln<br>450                      455                      460 | 1392 |

```
tgg gat acg agc aaa aat gca gga ttc acg agc gga aaa cct tgg ttc    1440
Trp Asp Thr Ser Lys Asn Ala Gly Phe Thr Ser Gly Lys Pro Trp Phe
465                 470                 475                 480 aag gtc aat cca aac tac cag gaa atc aat gcg gta agt caa gtc gca    1488
Lys Val Asn Pro Asn Tyr Gln Glu Ile Asn Ala Val Ser Gln Val Ala
                485                 490                 495 cag ccc gac tcg gta ttt aat tat tat cgt cag ttg atc aag ata agg    1536
Gln Pro Asp Ser Val Phe Asn Tyr Tyr Arg Gln Leu Ile Lys Ile Arg
            500                 505                 510 cat aac atc ccg gca ctg acc tat ggc aca tac acc gat ttg gat cct    1584
His Asn Ile Pro Ala Leu Thr Tyr Gly Thr Tyr Thr Asp Leu Asp Pro
        515                 520                 525 gca aat gat tcg gtc tac gcc tat aca cgc agc ctt ggg gcg gaa aaa    1632
Ala Asn Asp Ser Val Tyr Ala Tyr Thr Arg Ser Leu Gly Ala Glu Lys
    530                 535                 540 tat ctt gtt gtc gtt aac ttc cag gaa caa gtg atg aga tat aaa tta    1680
Tyr Leu Val Val Val Asn Phe Gln Glu Gln Val Met Arg Tyr Lys Leu
545                 550                 555                 560 ccg gat aat cta tcc atc gag aaa gtg att ata gaa agc aac agc aaa    1728
Pro Asp Asn Leu Ser Ile Glu Lys Val Ile Ile Glu Ser Asn Ser Lys
                565                 570                 575 aac gtt gtg aaa aag aat gat tcc tta ctc gaa cta aaa cca tgg cag    1776
Asn Val Val Lys Lys Asn Asp Ser Leu Leu Glu Leu Lys Pro Trp Gln
            580                 585                 590 tca ggg gtt tat aaa cta aat caa taa                                1803
Ser Gly Val Tyr Lys Leu Asn Gln
        595                 600

<210> SEQ ID NO 12
<211> LENGTH: 600
<212> TYPE: PRT
<213> ORGANISM: Serratia plymuthica

<400> SEQUENCE: 12

Met Pro Arg Gln Gly Leu Lys Thr Ala Leu Ala Ile Phe Leu Thr Thr
1               5                   10                  15

Ser Leu Ser Val Ser Cys Gln Gln Ala Leu Gly Thr Gln Gln Pro Leu
            20                  25                  30

Leu Asn Glu Lys Ser Ile Glu Gln Ser Lys Thr Ile Pro Lys Trp Trp
        35                  40                  45

Lys Glu Ala Val Phe Tyr Gln Val Tyr Pro Arg Ser Phe Lys Asp Thr
    50                  55                  60

Asn Gly Asp Gly Ile Gly Asp Ile Lys Gly Ile Ile Glu Lys Leu Asp
65                  70                  75                  80

Tyr Leu Lys Ala Leu Gly Ile Asp Ala Ile Trp Ile Asn Pro His Tyr
                85                  90                  95

Asp Ser Pro Asn Thr Asp Asn Gly Tyr Asp Ile Arg Asp Tyr Arg Lys
            100                 105                 110

Ile Met Lys Glu Tyr Gly Thr Met Glu Asp Phe Asp Arg Leu Ile Ser
        115                 120                 125

Glu Met Lys Lys Arg Asn Met Arg Leu Met Ile Asp Val Val Ile Asn
    130                 135                 140

His Thr Ser Asp Gln Asn Glu Trp Phe Val Lys Ser Lys Ser Ser Lys
145                 150                 155                 160

Asp Asn Pro Tyr Arg Gly Tyr Tyr Phe Trp Lys Asp Ala Lys Glu Gly
                165                 170                 175

Gln Ala Pro Asn Asn Tyr Pro Ser Phe Phe Gly Gly Ser Ala Trp Gln
```

-continued

```
                180                 185                 190
Lys Asp Glu Lys Thr Asn Gln Tyr Tyr Leu His Tyr Phe Ala Lys Gln
            195                 200                 205
Gln Pro Asp Leu Asn Trp Asp Asn Pro Lys Val Arg Gln Asp Leu Tyr
        210                 215                 220
Ala Met Leu Arg Phe Trp Leu Asp Lys Gly Val Ser Gly Leu Arg Phe
225                 230                 235                 240
Asp Thr Val Ala Thr Tyr Ser Lys Ile Pro Asp Phe Pro Asn Leu Thr
                245                 250                 255
Gln Gln Gln Leu Lys Asn Phe Ala Ala Glu Tyr Thr Lys Gly Pro Asn
            260                 265                 270
Ile His Arg Tyr Val Asn Glu Met Asn Arg Glu Val Leu Ser His Tyr
        275                 280                 285
Asp Ile Ala Thr Ala Gly Glu Ile Phe Gly Val Pro Leu Asp Gln Ser
        290                 295                 300
Ile Lys Phe Phe Asp Arg Arg Asp Glu Leu Asn Ile Ala Phe Thr
305                 310                 315                 320
Phe Asp Leu Ile Arg Leu Asp Arg Asp Ser Asp Gln Arg Trp Arg Arg
                325                 330                 335
Lys Glu Trp Lys Leu Ser Gln Phe Arg Gln Val Ile Asp Asn Val Asp
            340                 345                 350
Arg Thr Ala Gly Glu Tyr Gly Trp Asn Ala Phe Phe Leu Asp Asn His
        355                 360                 365
Asp Asn Pro Arg Ala Val Ser His Phe Gly Asp Asp Arg Pro Gln Trp
    370                 375                 380
Arg Glu Pro Ser Ala Lys Ala Leu Ala Thr Leu Thr Leu Thr Gln Arg
385                 390                 395                 400
Ala Thr Pro Phe Ile Tyr Gln Gly Ser Glu Leu Gly Met Thr Asn Tyr
                405                 410                 415
Pro Phe Lys Ala Ile Asp Glu Phe Asp Asp Ile Glu Val Lys Gly Phe
            420                 425                 430
Trp His Asp Tyr Val Glu Thr Gly Lys Val Lys Ala Asp Glu Phe Leu
        435                 440                 445
Gln Asn Val Arg Leu Thr Ser Arg Asp Asn Ser Arg Thr Pro Phe Gln
    450                 455                 460
Trp Asp Thr Ser Lys Asn Ala Gly Phe Thr Ser Gly Lys Pro Trp Phe
465                 470                 475                 480
Lys Val Asn Pro Asn Tyr Gln Glu Ile Asn Ala Val Ser Gln Val Ala
                485                 490                 495
Gln Pro Asp Ser Val Phe Asn Tyr Tyr Arg Gln Leu Ile Lys Ile Arg
            500                 505                 510
His Asn Ile Pro Ala Leu Thr Tyr Gly Thr Tyr Thr Asp Leu Asp Pro
        515                 520                 525
Ala Asn Asp Ser Val Tyr Ala Tyr Thr Arg Ser Leu Gly Ala Glu Lys
    530                 535                 540
Tyr Leu Val Val Val Asn Phe Gln Glu Gln Val Met Arg Tyr Lys Leu
545                 550                 555                 560
Pro Asp Asn Leu Ser Ile Glu Lys Val Ile Glu Ser Asn Ser Lys
                565                 570                 575
Asn Val Val Lys Lys Asn Asp Ser Leu Leu Glu Leu Lys Pro Trp Gln
            580                 585                 590
Ser Gly Val Tyr Lys Leu Asn Gln
        595                 600
```

<210> SEQ ID NO 13
<211> LENGTH: 1844
<212> TYPE: DNA
<213> ORGANISM: Artificial sequence
<220> FEATURE:
<223> OTHER INFORMATION: Description of the artificial sequence: coding
    for fusion protein of signal peptide from proteinase
    inhibitor I and sucrose isomerase from Erwinia
    rhapontici
<220> FEATURE:
<221> NAME/KEY: CDS
<222> LOCATION: (24)..(1835)
<220> FEATURE:
<221> NAME/KEY: sig_peptide
<222> LOCATION: (24)..(143)
<223> OTHER INFORMATION: signal peptide from proteinase inhibitor I
<220> FEATURE:
<221> NAME/KEY: misc_feature
<222> LOCATION: (144)..(1835)
<223> OTHER INFORMATION: coding for mature peptide of sucrose isomerase
    from Erwinia rhapontici    (palI)

<400> SEQUENCE: 13

```
ggtaccctaa ttaattatcc atc atg gat gtt cac aag gaa gtt aat ttc gtt         53
                         Met Asp Val His Lys Glu Val Asn Phe Val
                          1               5                  10 gct tac cta cta att gtt ctt gga tta ttg gta ctt gta agc gcg atg          101
Ala Tyr Leu Leu Ile Val Leu Gly Leu Leu Val Leu Val Ser Ala Met
             15                  20                  25 gag cat gtt gat gcg aag gct tgc acc gaa ttg ggg atc ctc acc gtt         149
Glu His Val Asp Ala Lys Ala Cys Thr Glu Leu Gly Ile Leu Thr Val
         30                  35                  40 cag caa tca aat gcc ctg ccc aca tgg tgg aag cag gct gtt ttt tat         197
Gln Gln Ser Asn Ala Leu Pro Thr Trp Trp Lys Gln Ala Val Phe Tyr
     45                  50                  55 cag gta tat cca cgc tca ttt aaa gat acg aat ggg gat ggc att ggg         245
Gln Val Tyr Pro Arg Ser Phe Lys Asp Thr Asn Gly Asp Gly Ile Gly
 60                  65                  70 gat tta aac ggt att att gag aat tta gac tat ctg aag aaa ctg ggt         293
Asp Leu Asn Gly Ile Ile Glu Asn Leu Asp Tyr Leu Lys Lys Leu Gly
75                  80                  85                  90 att gat gcg att tgg atc aat cca cat tac gat tcg ccg aat acg gat         341
Ile Asp Ala Ile Trp Ile Asn Pro His Tyr Asp Ser Pro Asn Thr Asp
             95                 100                 105 aat ggt tat gac atc cgg gat tac cgt aag ata atg aaa gaa tac ggt         389
Asn Gly Tyr Asp Ile Arg Asp Tyr Arg Lys Ile Met Lys Glu Tyr Gly
         110                 115                 120 acg atg gaa gac ttt gac cgt ctt att tca gaa atg aag aaa cgc aat         437
Thr Met Glu Asp Phe Asp Arg Leu Ile Ser Glu Met Lys Lys Arg Asn
     125                 130                 135 atg cgt ttg atg att gat att gtt atc aac cac acc agc gat cag cat         485
Met Arg Leu Met Ile Asp Ile Val Ile Asn His Thr Ser Asp Gln His
 140                 145                 150 gcc tgg ttt gtt cag agc aaa tcg ggt aag aac aac ccc tac agg gac         533
Ala Trp Phe Val Gln Ser Lys Ser Gly Lys Asn Asn Pro Tyr Arg Asp
155                 160                 165                 170 tat tac ttc tgg cgt gac ggt aag gat ggc cat gcc ccc aat aac tat         581
Tyr Tyr Phe Trp Arg Asp Gly Lys Asp Gly His Ala Pro Asn Asn Tyr
             175                 180                 185 ccc tcc ttc ttc ggt ggc tca gcc tgg gaa aaa gac gat aaa tca ggc         629
Pro Ser Phe Phe Gly Gly Ser Ala Trp Glu Lys Asp Asp Lys Ser Gly
         190                 195                 200 cag tat tac ctc cat tac ttt gcc aaa cag caa ccc gac ctc aac tgg         677
```

```
                Gln Tyr Tyr Leu His Tyr Phe Ala Lys Gln Gln Pro Asp Leu Asn Trp
                        205                 210                 215 gac aat ccc aaa gtc cgt caa gac ctg tat gac atg ctc cgc ttc tgg            725
Asp Asn Pro Lys Val Arg Gln Asp Leu Tyr Asp Met Leu Arg Phe Trp
220                 225                 230 tta gat aaa ggc gtt tct ggt tta cgc ttt gat acc gtt gcc acc tac            773
Leu Asp Lys Gly Val Ser Gly Leu Arg Phe Asp Thr Val Ala Thr Tyr
235                 240                 245                 250 tcg aaa atc ccg aac ttc cct gac ctt agc caa cag cag tta aaa aat            821
Ser Lys Ile Pro Asn Phe Pro Asp Leu Ser Gln Gln Gln Leu Lys Asn
                255                 260                 265 ttc gcc gag gaa tat act aaa ggt cct aaa att cac gac tac gtg aat            869
Phe Ala Glu Glu Tyr Thr Lys Gly Pro Lys Ile His Asp Tyr Val Asn
                270                 275                 280 gaa atg aac aga gaa gta tta tcc cac tat gat atc gcc act gcg ggg            917
Glu Met Asn Arg Glu Val Leu Ser His Tyr Asp Ile Ala Thr Ala Gly
                285                 290                 295 gaa ata ttt ggg gtt cct ctg gat aaa tcg att aag ttt ttc gat cgc            965
Glu Ile Phe Gly Val Pro Leu Asp Lys Ser Ile Lys Phe Phe Asp Arg
        300                 305                 310 cgt aga aat gaa tta aat ata gcg ttt acg ttt gat ctg atc agg ctc           1013
Arg Arg Asn Glu Leu Asn Ile Ala Phe Thr Phe Asp Leu Ile Arg Leu
315                 320                 325                 330 gat cgt gat gct gat gaa aga tgg cgg cga aaa gac tgg acc ctt tcg           1061
Asp Arg Asp Ala Asp Glu Arg Trp Arg Arg Lys Asp Trp Thr Leu Ser
                335                 340                 345 cag ttc cga aaa att gtc gat aag gtt gac caa acg gca gga gag tat           1109
Gln Phe Arg Lys Ile Val Asp Lys Val Asp Gln Thr Ala Gly Glu Tyr
                350                 355                 360 ggg tgg aat gcc ttt ttc tta gac aat cac gac aat ccc cgc gcg gtt           1157
Gly Trp Asn Ala Phe Phe Leu Asp Asn His Asp Asn Pro Arg Ala Val
                365                 370                 375 tct cac ttt ggt gat gat cga cca caa tgg cgc gag cat gcg gcg aaa           1205
Ser His Phe Gly Asp Asp Arg Pro Gln Trp Arg Glu His Ala Ala Lys
        380                 385                 390 gca ctg gca aca ttg acg ctg acc cag cgt gca acg ccg ttt atc tat           1253
Ala Leu Ala Thr Leu Thr Leu Thr Gln Arg Ala Thr Pro Phe Ile Tyr
395                 400                 405                 410 cag ggt tca gaa ctc ggt atg acc aat tat ccc ttt aaa aaa atc gat           1301
Gln Gly Ser Glu Leu Gly Met Thr Asn Tyr Pro Phe Lys Lys Ile Asp
                415                 420                 425 gat ttc gat gat gta gag gtg aaa ggt ttt tgg caa gac tac gtt gaa           1349
Asp Phe Asp Asp Val Glu Val Lys Gly Phe Trp Gln Asp Tyr Val Glu
                430                 435                 440 aca ggc aaa gtg aaa gct gag gaa ttc ctt caa aac gta cgc caa acc           1397
Thr Gly Lys Val Lys Ala Glu Glu Phe Leu Gln Asn Val Arg Gln Thr
                445                 450                 455 agc cgt gat aac agc aga acc ccc ttc cag tgg gat gca agc aaa aac           1445
Ser Arg Asp Asn Ser Arg Thr Pro Phe Gln Trp Asp Ala Ser Lys Asn
        460                 465                 470 gcg ggc ttt acc agt gga acc ccc tgg tta aaa atc aat ccc aat tat           1493
Ala Gly Phe Thr Ser Gly Thr Pro Trp Leu Lys Ile Asn Pro Asn Tyr
475                 480                 485                 490 aaa gaa atc aac agc gca gat cag att aat aat cca aat tcc gta ttt           1541
Lys Glu Ile Asn Ser Ala Asp Gln Ile Asn Asn Pro Asn Ser Val Phe
                495                 500                 505 aac tat tat aga aag ctg att aac att cgc cat gac atc cct gcc ttg           1589
Asn Tyr Tyr Arg Lys Leu Ile Asn Ile Arg His Asp Ile Pro Ala Leu
        510                 515                 520
```

```
acc tac ggc agt tat att gat tta gac cct gac aac aat tca gtc tat    1637
Thr Tyr Gly Ser Tyr Ile Asp Leu Asp Pro Asp Asn Asn Ser Val Tyr
            525                 530                 535 gct tac acc cga acg ctc ggc gct gaa aaa tat ctt gtg gtc att aat    1685
Ala Tyr Thr Arg Thr Leu Gly Ala Glu Lys Tyr Leu Val Val Ile Asn
    540                 545                 550 ttt aaa gaa gaa gtg atg cac tac acc ctg ccc ggg gat tta tcc atc    1733
Phe Lys Glu Glu Val Met His Tyr Thr Leu Pro Gly Asp Leu Ser Ile
555                 560                 565                 570 aat aag gtg att act gaa aac aac agt cac act att gtg aat aaa aat    1781
Asn Lys Val Ile Thr Glu Asn Asn Ser His Thr Ile Val Asn Lys Asn
                575                 580                 585 gac agg caa ctc cgt ctt gaa ccc tgg cag tcg ggc att tat aaa ctt    1829
Asp Arg Gln Leu Arg Leu Glu Pro Trp Gln Ser Gly Ile Tyr Lys Leu
            590                 595                 600 aat ccg taggtcgac                                                   1844
Asn Pro <210> SEQ ID NO 14
<211> LENGTH: 604
<212> TYPE: PRT
<213> ORGANISM: Artificial sequence
<220> FEATURE:
<223> OTHER INFORMATION: Description of the artificial sequence: coding
      for fusion protein of signal peptide from proteinase
      inhibitor I and sucrose isomerase from Erwinia
      rhapontici

<400> SEQUENCE: 14

Met Asp Val His Lys Glu Val Asn Phe Val Ala Tyr Leu Leu Ile Val
 1               5                  10                  15

Leu Gly Leu Leu Val Leu Val Ser Ala Met Glu His Val Asp Ala Lys
            20                  25                  30

Ala Cys Thr Glu Leu Gly Ile Leu Thr Val Gln Gln Ser Asn Ala Leu
        35                  40                  45

Pro Thr Trp Trp Lys Gln Ala Val Phe Tyr Gln Val Tyr Pro Arg Ser
    50                  55                  60

Phe Lys Asp Thr Asn Gly Asp Gly Ile Gly Asp Leu Asn Gly Ile Ile
65                  70                  75                  80

Glu Asn Leu Asp Tyr Leu Lys Lys Leu Gly Ile Asp Ala Ile Trp Ile
                85                  90                  95

Asn Pro His Tyr Asp Ser Pro Asn Thr Asp Asn Gly Tyr Asp Ile Arg
            100                 105                 110

Asp Tyr Arg Lys Ile Met Lys Glu Tyr Gly Thr Met Glu Asp Phe Asp
        115                 120                 125

Arg Leu Ile Ser Glu Met Lys Lys Arg Asn Met Arg Leu Met Ile Asp
    130                 135                 140

Ile Val Ile Asn His Thr Ser Asp Gln His Ala Trp Phe Val Gln Ser
145                 150                 155                 160

Lys Ser Gly Lys Asn Asn Pro Tyr Arg Asp Tyr Tyr Phe Trp Arg Asp
                165                 170                 175

Gly Lys Asp Gly His Ala Pro Asn Asn Tyr Pro Ser Phe Phe Gly Gly
            180                 185                 190

Ser Ala Trp Glu Lys Asp Lys Ser Gly Gln Tyr Tyr Leu His Tyr
        195                 200                 205

Phe Ala Lys Gln Gln Pro Asp Leu Asn Trp Asp Asn Pro Lys Val Arg
    210                 215                 220

Gln Asp Leu Tyr Asp Met Leu Arg Phe Trp Leu Asp Lys Gly Val Ser
```

```
            225                 230                 235                 240
Gly Leu Arg Phe Asp Thr Val Ala Thr Tyr Ser Lys Ile Pro Asn Phe
                245                 250                 255
Pro Asp Leu Ser Gln Gln Leu Lys Asn Phe Ala Glu Glu Tyr Thr
            260                 265                 270
Lys Gly Pro Lys Ile His Asp Tyr Val Asn Glu Met Asn Arg Glu Val
            275                 280                 285
Leu Ser His Tyr Asp Ile Ala Thr Ala Gly Glu Ile Phe Gly Val Pro
            290                 295                 300
Leu Asp Lys Ser Ile Lys Phe Phe Asp Arg Arg Asn Glu Leu Asn
305                 310                 315                 320
Ile Ala Phe Thr Phe Asp Leu Ile Arg Leu Asp Arg Asp Ala Asp Glu
                325                 330                 335
Arg Trp Arg Arg Lys Asp Trp Thr Leu Ser Gln Phe Arg Lys Ile Val
                340                 345                 350
Asp Lys Val Asp Gln Thr Ala Gly Glu Tyr Gly Trp Asn Ala Phe Phe
            355                 360                 365
Leu Asp Asn His Asp Asn Pro Arg Ala Val Ser His Phe Gly Asp Asp
            370                 375                 380
Arg Pro Gln Trp Arg Glu His Ala Ala Lys Ala Leu Ala Thr Leu Thr
385                 390                 395                 400
Leu Thr Gln Arg Ala Thr Pro Phe Ile Tyr Gln Gly Ser Glu Leu Gly
                405                 410                 415
Met Thr Asn Tyr Pro Phe Lys Lys Ile Asp Asp Phe Asp Asp Val Glu
                420                 425                 430
Val Lys Gly Phe Trp Gln Asp Tyr Val Glu Thr Gly Lys Val Lys Ala
            435                 440                 445
Glu Glu Phe Leu Gln Asn Val Arg Gln Thr Ser Arg Asp Asn Ser Arg
            450                 455                 460
Thr Pro Phe Gln Trp Asp Ala Ser Lys Asn Ala Gly Phe Thr Ser Gly
465                 470                 475                 480
Thr Pro Trp Leu Lys Ile Asn Pro Asn Tyr Lys Glu Ile Asn Ser Ala
                485                 490                 495
Asp Gln Ile Asn Asn Pro Asn Ser Val Phe Asn Tyr Tyr Arg Lys Leu
            500                 505                 510
Ile Asn Ile Arg His Asp Ile Pro Ala Leu Thr Tyr Gly Ser Tyr Ile
            515                 520                 525
Asp Leu Asp Pro Asp Asn Asn Ser Val Tyr Ala Tyr Thr Arg Thr Leu
            530                 535                 540
Gly Ala Glu Lys Tyr Leu Val Val Ile Asn Phe Lys Glu Glu Val Met
545                 550                 555                 560
His Tyr Thr Leu Pro Gly Asp Leu Ser Ile Asn Lys Val Ile Thr Glu
                565                 570                 575
Asn Asn Ser His Thr Ile Val Asn Lys Asn Asp Arg Gln Leu Arg Leu
            580                 585                 590
Glu Pro Trp Gln Ser Gly Ile Tyr Lys Leu Asn Pro
            595                 600

<210> SEQ ID NO 15
<211> LENGTH: 2477
<212> TYPE: DNA
<213> ORGANISM: Klebsiella sp.
<220> FEATURE:
<221> NAME/KEY: CDS
<222> LOCATION: (214)..(2007)
```

<223> OTHER INFORMATION: coding for sucrose isomerase

<400> SEQUENCE: 15

| | |
|---|---:|
| gatatcactg gtattatgga gtattatact cccccttat ttactcatca aagccaggcg | 60 |
| ttccactctg cctccggtat ataactttcc gggaaacaat cccttcctga aaataattat | 120 |
| tgttaccgga gtcatactct ggctattgat gatttacgct tttctttaat aacaattcgt | 180 |
| ctcattcaca actgactttg caaggaaatt att atg tct ttt gtt acg cta cgt | 234 |

|  |  |  |  |  |  |  |
|---|---|---|---|---|---|---|
|  |  |  | Met | Ser | Phe | Val | Thr | Leu | Arg |
|  |  |  | 1 |  |  | 5 |

| | |
|---|---:|
| acc ggg gtg gct gtc gcg ctg tca tct ttg ata ata agt ctg gcc tgc<br>Thr Gly Val Ala Val Ala Leu Ser Ser Leu Ile Ile Ser Leu Ala Cys<br>     10              15              20 | 282 |
| ccg gct gtc agt gct gca cca tcc ttg aat cag gat att cac gtt caa<br>Pro Ala Val Ser Ala Ala Pro Ser Leu Asn Gln Asp Ile His Val Gln<br>25               30              35 | 330 |
| aag gaa agt gaa tat cct gca tgg tgg aaa gaa gct gtt ttt tat cag<br>Lys Glu Ser Glu Tyr Pro Ala Trp Trp Lys Glu Ala Val Phe Tyr Gln<br>40               45              50              55 | 378 |
| atc tat cct cgc tca ttt aaa gac acc aat gat gat ggc att ggc gat<br>Ile Tyr Pro Arg Ser Phe Lys Asp Thr Asn Asp Asp Gly Ile Gly Asp<br>         60              65              70 | 426 |
| att cgc ggt att att gaa aag ctg gac tat ctg aaa tcg ctc ggt att<br>Ile Arg Gly Ile Ile Glu Lys Leu Asp Tyr Leu Lys Ser Leu Gly Ile<br>            75              80              85 | 474 |
| gac gct atc tgg atc aat ccc cat tac gac tct ccg aac acc gat aac<br>Asp Ala Ile Trp Ile Asn Pro His Tyr Asp Ser Pro Asn Thr Asp Asn<br>         90              95             100 | 522 |
| ggc tat gac atc agt aat tat cgt cag ata atg aaa gag tat ggc aca<br>Gly Tyr Asp Ile Ser Asn Tyr Arg Gln Ile Met Lys Glu Tyr Gly Thr<br>105              110             115 | 570 |
| atg gag gat ttt gat agc ctt gtt gcc gaa atg aaa aaa cga aat atg<br>Met Glu Asp Phe Asp Ser Leu Val Ala Glu Met Lys Lys Arg Asn Met<br>120              125            130            135 | 618 |
| cgc tta atg atc gac gtg gtc att aac cat acc agt gat caa cac ccg<br>Arg Leu Met Ile Asp Val Val Ile Asn His Thr Ser Asp Gln His Pro<br>         140             145            150 | 666 |
| tgg ttt att cag agt aaa agc gat aaa aac aac cct tat cgt gac tat<br>Trp Phe Ile Gln Ser Lys Ser Asp Lys Asn Asn Pro Tyr Arg Asp Tyr<br>            155             160            165 | 714 |
| tat ttc tgg cgt gac gga aaa gat aat cag cca cct aat aat tac ccc<br>Tyr Phe Trp Arg Asp Gly Lys Asp Asn Gln Pro Pro Asn Asn Tyr Pro<br>170              175            180 | 762 |
| tca ttt ttc ggc ggc tcg gca tgg caa aaa gat gca aag tca gga cag<br>Ser Phe Phe Gly Gly Ser Ala Trp Gln Lys Asp Ala Lys Ser Gly Gln<br>185              190            195 | 810 |
| tac tat tta cac tat ttt gcc aga cag caa cct gat ctc aac tgg gat<br>Tyr Tyr Leu His Tyr Phe Ala Arg Gln Gln Pro Asp Leu Asn Trp Asp<br>200              205            210            215 | 858 |
| aac ccg aaa gta cgt gag gat ctt tac gca atg ctc cgc ttc tgg ctg<br>Asn Pro Lys Val Arg Glu Asp Leu Tyr Ala Met Leu Arg Phe Trp Leu<br>         220             225            230 | 906 |
| gat aaa ggc gtt tca ggc atg cga ttt gat acg gtg gca act tat tcc<br>Asp Lys Gly Val Ser Gly Met Arg Phe Asp Thr Val Ala Thr Tyr Ser<br>            235             240            245 | 954 |
| aaa atc ccg gga ttt ccc aat ctg aca cct gaa caa cag aaa aat ttt<br>Lys Ile Pro Gly Phe Pro Asn Leu Thr Pro Glu Gln Gln Lys Asn Phe<br>250              255            260 | 1002 |
| gct gaa caa tac acc atg ggg cct aat att cat cga tac att cag gaa | 1050 |

```
                Ala Glu Gln Tyr Thr Met Gly Pro Asn Ile His Arg Tyr Ile Gln Glu
                    265                 270                 275 atg aac cgg aaa gtt ctg tcc cgg tat gat gtg gcc acc gcg ggt gaa          1098
Met Asn Arg Lys Val Leu Ser Arg Tyr Asp Val Ala Thr Ala Gly Glu
280                 285                 290                 295 att ttt ggc gtc ccg ctg gat cgt tcg tcg cag ttt ttt gat cgc cgc          1146
Ile Phe Gly Val Pro Leu Asp Arg Ser Ser Gln Phe Phe Asp Arg Arg
                300                 305                 310 cga cat gag ctg aat atg gcg ttt atg ttt gac ctc att cgt ctc gat          1194
Arg His Glu Leu Asn Met Ala Phe Met Phe Asp Leu Ile Arg Leu Asp
            315                 320                 325 cgc gac agc aat gaa cgc tgg cgt cac aag tcg tgg tcg ctc tct cag          1242
Arg Asp Ser Asn Glu Arg Trp Arg His Lys Ser Trp Ser Leu Ser Gln
        330                 335                 340 ttc cgc cag atc atc agc aaa atg gat gtc acg gtc gga aag tat ggc          1290
Phe Arg Gln Ile Ile Ser Lys Met Asp Val Thr Val Gly Lys Tyr Gly
    345                 350                 355 tgg aac acg ttc ttc tta gat aac cat gac aac ccc cgt gcg gta tct          1338
Trp Asn Thr Phe Phe Leu Asp Asn His Asp Asn Pro Arg Ala Val Ser
360                 365                 370                 375 cac ttc ggg gat gac agg ccg caa tgg cgg gag gcg tcg gct aag gca          1386
His Phe Gly Asp Asp Arg Pro Gln Trp Arg Glu Ala Ser Ala Lys Ala
                380                 385                 390 ctg gcg acg att acc ctc act cag cgg gcg acg ccg ttt att tat cag          1434
Leu Ala Thr Ile Thr Leu Thr Gln Arg Ala Thr Pro Phe Ile Tyr Gln
            395                 400                 405 ggt tca gag ctg gga atg act aat tat ccc ttc agg caa ctc aac gaa          1482
Gly Ser Glu Leu Gly Met Thr Asn Tyr Pro Phe Arg Gln Leu Asn Glu
        410                 415                 420 ttt gac gac atc gag gtc aaa ggt ttc tgg cag gat tat gtc cag agt          1530
Phe Asp Asp Ile Glu Val Lys Gly Phe Trp Gln Asp Tyr Val Gln Ser
    425                 430                 435 gga aaa gtc acg gcc aca gag ttt ctc gat aat gtg cgc ctg acg agc          1578
Gly Lys Val Thr Ala Thr Glu Phe Leu Asp Asn Val Arg Leu Thr Ser
440                 445                 450                 455 cgc gat aac agc aga aca cct ttc cag tgg aat gac acc ctg aat gct          1626
Arg Asp Asn Ser Arg Thr Pro Phe Gln Trp Asn Asp Thr Leu Asn Ala
                460                 465                 470 ggt ttt act cgc gga aag ccg tgg ttt cac atc aac cca aac tat gtg          1674
Gly Phe Thr Arg Gly Lys Pro Trp Phe His Ile Asn Pro Asn Tyr Val
            475                 480                 485 gag atc aac gcc gaa cgc gaa gaa acc cgc gaa gat tca gtg ctg aat          1722
Glu Ile Asn Ala Glu Arg Glu Glu Thr Arg Glu Asp Ser Val Leu Asn
        490                 495                 500 tac tat aaa aaa atg att cag cta cgc cac cat atc cct gct ctg gta          1770
Tyr Tyr Lys Lys Met Ile Gln Leu Arg His His Ile Pro Ala Leu Val
    505                 510                 515 tat ggc gcc tat cag gat ctt aat cca cag gac aat acc gtt tat gcc          1818
Tyr Gly Ala Tyr Gln Asp Leu Asn Pro Gln Asp Asn Thr Val Tyr Ala
520                 525                 530                 535 tat acc cga acg ctg ggt aac gag cgt tat ctg gtc gtg gtg aac ttt          1866
Tyr Thr Arg Thr Leu Gly Asn Glu Arg Tyr Leu Val Val Val Asn Phe
                540                 545                 550 aag gag tac ccg gtc cgc tat act ctc ccg gct aat gat gcc atc gag          1914
Lys Glu Tyr Pro Val Arg Tyr Thr Leu Pro Ala Asn Asp Ala Ile Glu
            555                 560                 565 gaa gtg gtc att gat act cag cag cag gcg gct gcg ccg cac agc aca          1962
Glu Val Val Ile Asp Thr Gln Gln Gln Ala Ala Ala Pro His Ser Thr
        570                 575                 580
```

-continued

```
tcc ctg tca ttg agc ccc tgg cag gca ggt gtg tat aag ctg cgg        2007
Ser Leu Ser Leu Ser Pro Trp Gln Ala Gly Val Tyr Lys Leu Arg
    585                 590                 595 taatcacctg ggggattgat gacaagttcc ccagacaata gagttttcca ggtctttagc   2067
actgctgtgc tcagcgatag ttgtgctctc ctgtgacttc gtaagtgcct gtctcatggc   2127
aggcattgtc aggtcagaag ccttctcagg cagcctcgag taacagcgcc cagttagcat   2187 cccccctgaaa gatgggggt atgtataaat tagcgttaaa gaacatgaac cagccaccgt   2247
catcttatca accaacaggc gagatgagct ccgattcctg attcttcaca ttgccgttga   2307
tgcgcctgaa gcctcgccct ttagggccgg gaaataagca cagcatctgg cgatctcttt   2367
tgccacttta ctgatcacat ccggcctcat ccatttccgg gcggcttcag ccatcaggag   2427
aaagggtagt ggtcgtgtat atgagccagg ccaaaaaaag gtgtgatatc              2477
```

<210> SEQ ID NO 16
<211> LENGTH: 598
<212> TYPE: PRT
<213> ORGANISM: Klebsiella sp.

<400> SEQUENCE: 16

```
Met Ser Phe Val Thr Leu Arg Thr Gly Val Ala Val Ala Leu Ser Ser
 1               5                  10                  15

Leu Ile Ile Ser Leu Ala Cys Pro Ala Val Ser Ala Ala Pro Ser Leu
            20                  25                  30

Asn Gln Asp Ile His Val Gln Lys Glu Ser Glu Tyr Pro Ala Trp Trp
        35                  40                  45

Lys Glu Ala Val Phe Tyr Gln Ile Tyr Pro Arg Ser Phe Lys Asp Thr
    50                  55                  60

Asn Asp Asp Gly Ile Gly Asp Ile Arg Gly Ile Ile Glu Lys Leu Asp
65                  70                  75                  80

Tyr Leu Lys Ser Leu Gly Ile Asp Ala Ile Trp Ile Asn Pro His Tyr
                85                  90                  95

Asp Ser Pro Asn Thr Asp Asn Gly Tyr Asp Ile Ser Asn Tyr Arg Gln
            100                 105                 110

Ile Met Lys Glu Tyr Gly Thr Met Glu Asp Phe Asp Ser Leu Val Ala
        115                 120                 125

Glu Met Lys Lys Arg Asn Met Arg Leu Met Ile Asp Val Val Ile Asn
    130                 135                 140

His Thr Ser Asp Gln His Pro Trp Phe Ile Gln Ser Lys Ser Asp Lys
145                 150                 155                 160

Asn Asn Pro Tyr Arg Asp Tyr Tyr Phe Trp Arg Asp Gly Lys Asp Asn
                165                 170                 175

Gln Pro Pro Asn Asn Tyr Pro Ser Phe Phe Gly Gly Ser Ala Trp Gln
            180                 185                 190

Lys Asp Ala Lys Ser Gly Gln Tyr Tyr Leu His Tyr Phe Ala Arg Gln
        195                 200                 205

Gln Pro Asp Leu Asn Trp Asp Asn Pro Lys Val Arg Glu Asp Leu Tyr
    210                 215                 220

Ala Met Leu Arg Phe Trp Leu Asp Lys Gly Val Ser Gly Met Arg Phe
225                 230                 235                 240

Asp Thr Val Ala Thr Tyr Ser Lys Ile Pro Gly Phe Pro Asn Leu Thr
                245                 250                 255

Pro Glu Gln Gln Lys Asn Phe Ala Glu Gln Tyr Thr Met Gly Pro Asn
            260                 265                 270
```

```
Ile His Arg Tyr Ile Gln Glu Met Asn Arg Lys Val Leu Ser Arg Tyr
        275                 280                 285

Asp Val Ala Thr Ala Gly Glu Ile Phe Gly Val Pro Leu Asp Arg Ser
        290                 295                 300

Ser Gln Phe Phe Asp Arg Arg His Glu Leu Asn Met Ala Phe Met
305                 310                 315                 320

Phe Asp Leu Ile Arg Leu Asp Arg Asp Ser Asn Glu Arg Trp Arg His
                325                 330                 335

Lys Ser Trp Ser Leu Ser Gln Phe Arg Gln Ile Ile Ser Lys Met Asp
                340                 345                 350

Val Thr Val Gly Lys Tyr Gly Trp Asn Thr Phe Leu Asp Asn His
        355                 360                 365

Asp Asn Pro Arg Ala Val Ser His Phe Gly Asp Arg Pro Gln Trp
        370                 375                 380

Arg Glu Ala Ser Ala Lys Ala Leu Ala Thr Ile Thr Leu Thr Gln Arg
385                 390                 395                 400

Ala Thr Pro Phe Ile Tyr Gln Gly Ser Glu Leu Gly Met Thr Asn Tyr
                405                 410                 415

Pro Phe Arg Gln Leu Asn Glu Phe Asp Asp Ile Glu Val Lys Gly Phe
                420                 425                 430

Trp Gln Asp Tyr Val Gln Ser Gly Lys Val Thr Ala Thr Glu Phe Leu
                435                 440                 445

Asp Asn Val Arg Leu Thr Ser Arg Asp Asn Ser Arg Thr Pro Phe Gln
450                 455                 460

Trp Asn Asp Thr Leu Asn Ala Gly Phe Thr Arg Gly Lys Pro Trp Phe
465                 470                 475                 480

His Ile Asn Pro Asn Tyr Val Glu Ile Asn Ala Glu Arg Glu Thr
                485                 490                 495

Arg Glu Asp Ser Val Leu Asn Tyr Tyr Lys Lys Met Ile Gln Leu Arg
                500                 505                 510

His His Ile Pro Ala Leu Val Tyr Gly Ala Tyr Gln Asp Leu Asn Pro
        515                 520                 525

Gln Asp Asn Thr Val Tyr Ala Tyr Thr Arg Thr Leu Gly Asn Glu Arg
        530                 535                 540

Tyr Leu Val Val Val Asn Phe Lys Glu Tyr Pro Val Arg Tyr Thr Leu
545                 550                 555                 560

Pro Ala Asn Asp Ala Ile Glu Glu Val Ile Asp Thr Gln Gln Gln
                565                 570                 575

Ala Ala Ala Pro His Ser Thr Ser Leu Ser Leu Ser Pro Trp Gln Ala
                580                 585                 590

Gly Val Tyr Lys Leu Arg
        595

<210> SEQ ID NO 17
<211> LENGTH: 1797
<212> TYPE: DNA
<213> ORGANISM: Klebsiella sp.
<220> FEATURE:
<221> NAME/KEY: CDS
<222> LOCATION: (1)..(1794)
<223> OTHER INFORMATION: coding for sucrose isomerase

<400> SEQUENCE: 17 atg tct ttt gtt acg cta cgt acc ggg gtg gct gtc gcg ctg tca tct    48
Met Ser Phe Val Thr Leu Arg Thr Gly Val Ala Val Ala Leu Ser Ser
 1               5                  10                  15
```

-continued

| | | |
|---|---|---|
| ttg ata ata agt ctg gcc tgc ccg gct gtc agt gct gca cca tcc ttg<br>Leu Ile Ile Ser Leu Ala Cys Pro Ala Val Ser Ala Ala Pro Ser Leu<br>                20                        25                        30 | 96 | |
| aat cag gat att cac gtt caa aag gaa agt gaa tat cct gca tgg tgg<br>Asn Gln Asp Ile His Val Gln Lys Glu Ser Glu Tyr Pro Ala Trp Trp<br>       35                        40                        45 | 144 | |
| aaa gaa gct gtt ttt tat cag atc tat cct cgc tca ttt aaa gac acc<br>Lys Glu Ala Val Phe Tyr Gln Ile Tyr Pro Arg Ser Phe Lys Asp Thr<br> 50                        55                        60 | 192 | |
| aat gat gat ggc att ggc gat att cgc ggt att att gaa aag ctg gac<br>Asn Asp Asp Gly Ile Gly Asp Ile Arg Gly Ile Ile Glu Lys Leu Asp<br>65                      70                        75                        80 | 240 | |
| tat ctg aaa tcg ctc ggt att gac gct atc tgg atc aat ccc cat tac<br>Tyr Leu Lys Ser Leu Gly Ile Asp Ala Ile Trp Ile Asn Pro His Tyr<br>                85                        90                        95 | 288 | |
| gac tct ccg aac acc gat aac ggc tat gac atc agt aat tat cgt cag<br>Asp Ser Pro Asn Thr Asp Asn Gly Tyr Asp Ile Ser Asn Tyr Arg Gln<br>                   100                      105                   110 | 336 | |
| ata atg aaa gag tat ggc aca atg gag gat ttt gat agc ctt gtt gcc<br>Ile Met Lys Glu Tyr Gly Thr Met Glu Asp Phe Asp Ser Leu Val Ala<br>       115                       120                       125 | 384 | |
| gaa atg aaa aaa cga aat atg cgc tta atg atc gac gtg gtc att aac<br>Glu Met Lys Lys Arg Asn Met Arg Leu Met Ile Asp Val Val Ile Asn<br>130                       135                        140 | 432 | |
| cat acc agt gat caa cac ccg tgg ttt att cag agt aaa agc gat aaa<br>His Thr Ser Asp Gln His Pro Trp Phe Ile Gln Ser Lys Ser Asp Lys<br>145                       150                       155                       160 | 480 | |
| aac aac cct tat cgt gac tat tat ttc tgg cgt gac gga aaa gat aat<br>Asn Asn Pro Tyr Arg Asp Tyr Tyr Phe Trp Arg Asp Gly Lys Asp Asn<br>                   165                      170                      175 | 528 | |
| cag cca cct aat aat tac ccc tca ttt ttc ggc ggc tcg gca tgg caa<br>Gln Pro Pro Asn Asn Tyr Pro Ser Phe Phe Gly Gly Ser Ala Trp Gln<br>                 180                      185                   190 | 576 | |
| aaa gat gca aag tca gga cag tac tat tta cac tat ttt gcc aga cag<br>Lys Asp Ala Lys Ser Gly Gln Tyr Tyr Leu His Tyr Phe Ala Arg Gln<br>     195                       200                       205 | 624 | |
| caa cct gat ctc aac tgg gat aac ccg aaa gta cgt gag gat ctt tac<br>Gln Pro Asp Leu Asn Trp Asp Asn Pro Lys Val Arg Glu Asp Leu Tyr<br>210                       215                        220 | 672 | |
| gca atg ctc cgc ttc tgg ctg gat aaa ggc gtt tca ggc atg cga ttt<br>Ala Met Leu Arg Phe Trp Leu Asp Lys Gly Val Ser Gly Met Arg Phe<br>225                       230                       235                    240 | 720 | |
| gat acg gtg gca act tat tcc aaa atc ccg gga ttt ccc aat ctg aca<br>Asp Thr Val Ala Thr Tyr Ser Lys Ile Pro Gly Phe Pro Asn Leu Thr<br>                   245                      250                      255 | 768 | |
| cct gaa caa cag aaa aat ttt gct gaa caa tac acc atg ggg cct aat<br>Pro Glu Gln Gln Lys Asn Phe Ala Glu Gln Tyr Thr Met Gly Pro Asn<br>               260                      265                     270 | 816 | |
| att cat cga tac att cag gaa atg aac cgg aaa gtt ctg tcc cgg tat<br>Ile His Arg Tyr Ile Gln Glu Met Asn Arg Lys Val Leu Ser Arg Tyr<br>     275                       280                       285 | 864 | |
| gat gtg gcc acc gcg ggt gaa att ttt ggc gtc ccg ctg gat cgt tcg<br>Asp Val Ala Thr Ala Gly Glu Ile Phe Gly Val Pro Leu Asp Arg Ser<br>          290                     295                      300 | 912 | |
| tcg cag ttt ttt gat cgc cgc cga cat gag ctg aat atg gcg ttt atg<br>Ser Gln Phe Phe Asp Arg Arg Arg His Glu Leu Asn Met Ala Phe Met<br>305                       310                       315                    320 | 960 | |
| ttt gac ctc att cgt ctc gat cgc gac agc aat gaa cgc tgg cgt cac<br>Phe Asp Leu Ile Arg Leu Asp Arg Asp Ser Asn Glu Arg Trp Arg His<br>                   325                      330                      335 | 1008 | |

```
aag tcg tgg tcg ctc tct cag ttc cgc cag atc atc agc aaa atg gat    1056
Lys Ser Trp Ser Leu Ser Gln Phe Arg Gln Ile Ile Ser Lys Met Asp
        340                 345                 350 gtc acg gtc gga aag tat ggc tgg aac acg ttc ttc tta gat aac cat    1104
Val Thr Val Gly Lys Tyr Gly Trp Asn Thr Phe Phe Leu Asp Asn His
355                 360                 365 gac aac ccc cgt gcg gta tct cac ttc ggg gat gac agg ccg caa tgg    1152
Asp Asn Pro Arg Ala Val Ser His Phe Gly Asp Asp Arg Pro Gln Trp
    370                 375                 380 cgg gag gcg tcg gct aag gca ctg gcg acg att acc ctc act cag cgg    1200
Arg Glu Ala Ser Ala Lys Ala Leu Ala Thr Ile Thr Leu Thr Gln Arg
385                 390                 395                 400 gcg acg ccg ttt att tat cag ggt tca gag ctg gga atg act aat tat    1248
Ala Thr Pro Phe Ile Tyr Gln Gly Ser Glu Leu Gly Met Thr Asn Tyr
                405                 410                 415 ccc ttc agg caa ctc aac gaa ttt gac gac atc gag gtc aaa ggt ttc    1296
Pro Phe Arg Gln Leu Asn Glu Phe Asp Asp Ile Glu Val Lys Gly Phe
            420                 425                 430 tgg cag gat tat gtc cag agt gga aaa gtc acg gcc aca gag ttt ctc    1344
Trp Gln Asp Tyr Val Gln Ser Gly Lys Val Thr Ala Thr Glu Phe Leu
        435                 440                 445 gat aat gtg cgc ctg acg agc cgc gat aac agc aga aca cct ttc cag    1392
Asp Asn Val Arg Leu Thr Ser Arg Asp Asn Ser Arg Thr Pro Phe Gln
450                 455                 460 tgg aat gac acc ctg aat gct ggt ttt act cgc gga aag ccg tgg ttt    1440
Trp Asn Asp Thr Leu Asn Ala Gly Phe Thr Arg Gly Lys Pro Trp Phe
465                 470                 475                 480 cac atc aac cca aac tat gtg gag atc aac gcc gaa cgc gaa gaa acc    1488
His Ile Asn Pro Asn Tyr Val Glu Ile Asn Ala Glu Arg Glu Glu Thr
                485                 490                 495 cgc gaa gat tca gtg ctg aat tac tat aaa aaa atg att cag cta cgc    1536
Arg Glu Asp Ser Val Leu Asn Tyr Tyr Lys Lys Met Ile Gln Leu Arg
            500                 505                 510 cac cat atc cct gct ctg gta tat ggc gcc tat cag gat ctt aat cca    1584
His His Ile Pro Ala Leu Val Tyr Gly Ala Tyr Gln Asp Leu Asn Pro
        515                 520                 525 cag gac aat acc gtt tat gcc tat acc cga acg ctg ggt aac gag cgt    1632
Gln Asp Asn Thr Val Tyr Ala Tyr Thr Arg Thr Leu Gly Asn Glu Arg
530                 535                 540 tat ctg gtc gtg gtg aac ttt aag gag tac ccg gtc cgc tat act ctc    1680
Tyr Leu Val Val Val Asn Phe Lys Glu Tyr Pro Val Arg Tyr Thr Leu
545                 550                 555                 560 ccg gct aat gat gcc atc gag gaa gtg gtc att gat act cag cag cag    1728
Pro Ala Asn Asp Ala Ile Glu Glu Val Val Ile Asp Thr Gln Gln Gln
                565                 570                 575 gcg gct gcg ccg cac agc aca tcc ctg tca ttg agc ccc tgg cag gca    1776
Ala Ala Ala Pro His Ser Thr Ser Leu Ser Leu Ser Pro Trp Gln Ala
            580                 585                 590 ggt gtg tat aag ctg cgg taa                                        1797
Gly Val Tyr Lys Leu Arg
        595

<210> SEQ ID NO 18
<211> LENGTH: 598
<212> TYPE: PRT
<213> ORGANISM: Klebsiella sp.

<400> SEQUENCE: 18

Met Ser Phe Val Thr Leu Arg Thr Gly Val Ala Val Ala Leu Ser Ser
1               5                   10                  15
```

```
Leu Ile Ile Ser Leu Ala Cys Pro Ala Val Ser Ala Ala Pro Ser Leu
                 20                  25                  30

Asn Gln Asp Ile His Val Gln Lys Glu Ser Glu Tyr Pro Ala Trp Trp
         35                  40                  45

Lys Glu Ala Val Phe Tyr Gln Ile Tyr Pro Arg Ser Phe Lys Asp Thr
     50                  55                  60

Asn Asp Asp Gly Ile Gly Asp Ile Arg Gly Ile Ile Glu Lys Leu Asp
 65                  70                  75                  80

Tyr Leu Lys Ser Leu Gly Ile Asp Ala Ile Trp Ile Asn Pro His Tyr
                 85                  90                  95

Asp Ser Pro Asn Thr Asp Asn Gly Tyr Asp Ile Ser Asn Tyr Arg Gln
            100                 105                 110

Ile Met Lys Glu Tyr Gly Thr Met Glu Asp Phe Asp Ser Leu Val Ala
            115                 120                 125

Glu Met Lys Lys Arg Asn Met Arg Leu Met Ile Asp Val Val Ile Asn
130                 135                 140

His Thr Ser Asp Gln His Pro Trp Phe Ile Gln Ser Lys Ser Asp Lys
145                 150                 155                 160

Asn Asn Pro Tyr Arg Asp Tyr Tyr Phe Trp Arg Asp Gly Lys Asp Asn
                165                 170                 175

Gln Pro Pro Asn Asn Tyr Pro Ser Phe Phe Gly Gly Ser Ala Trp Gln
            180                 185                 190

Lys Asp Ala Lys Ser Gly Gln Tyr Tyr Leu His Tyr Phe Ala Arg Gln
            195                 200                 205

Gln Pro Asp Leu Asn Trp Asp Asn Pro Lys Val Arg Glu Asp Leu Tyr
            210                 215                 220

Ala Met Leu Arg Phe Trp Leu Asp Lys Gly Val Ser Gly Met Arg Phe
225                 230                 235                 240

Asp Thr Val Ala Thr Tyr Ser Lys Ile Pro Gly Phe Pro Asn Leu Thr
                245                 250                 255

Pro Glu Gln Gln Lys Asn Phe Ala Glu Gln Tyr Thr Met Gly Pro Asn
            260                 265                 270

Ile His Arg Tyr Ile Gln Glu Met Asn Arg Lys Val Leu Ser Arg Tyr
            275                 280                 285

Asp Val Ala Thr Ala Gly Glu Ile Phe Gly Val Pro Leu Asp Arg Ser
            290                 295                 300

Ser Gln Phe Phe Asp Arg Arg His Glu Leu Asn Met Ala Phe Met
305                 310                 315                 320

Phe Asp Leu Ile Arg Leu Asp Arg Asp Ser Asn Glu Arg Trp Arg His
                325                 330                 335

Lys Ser Trp Ser Leu Ser Gln Phe Arg Gln Ile Ile Ser Lys Met Asp
            340                 345                 350

Val Thr Val Gly Lys Tyr Gly Trp Asn Thr Phe Phe Leu Asp Asn His
            355                 360                 365

Asp Asn Pro Arg Ala Val Ser His Phe Gly Asp Asp Arg Pro Gln Trp
            370                 375                 380

Arg Glu Ala Ser Ala Lys Ala Leu Ala Thr Ile Thr Leu Thr Gln Arg
385                 390                 395                 400

Ala Thr Pro Phe Ile Tyr Gln Gly Ser Glu Leu Gly Met Thr Asn Tyr
                405                 410                 415

Pro Phe Arg Gln Leu Asn Glu Phe Asp Asp Ile Glu Val Lys Gly Phe
            420                 425                 430
```

```
Trp Gln Asp Tyr Val Gln Ser Gly Lys Val Thr Ala Thr Glu Phe Leu
        435                 440                 445

Asp Asn Val Arg Leu Thr Ser Arg Asp Asn Ser Arg Thr Pro Phe Gln
    450                 455                 460

Trp Asn Asp Thr Leu Asn Ala Gly Phe Thr Arg Gly Lys Pro Trp Phe
465                 470                 475                 480

His Ile Asn Pro Asn Tyr Val Glu Ile Asn Ala Glu Arg Glu Thr
                485                 490                 495

Arg Glu Asp Ser Val Leu Asn Tyr Tyr Lys Lys Met Ile Gln Leu Arg
            500                 505                 510

His His Ile Pro Ala Leu Val Tyr Gly Ala Tyr Gln Asp Leu Asn Pro
        515                 520                 525

Gln Asp Asn Thr Val Tyr Ala Tyr Thr Arg Thr Leu Gly Asn Glu Arg
    530                 535                 540

Tyr Leu Val Val Val Asn Phe Lys Glu Tyr Pro Val Arg Tyr Thr Leu
545                 550                 555                 560

Pro Ala Asn Asp Ala Ile Glu Glu Val Val Ile Asp Thr Gln Gln Gln
                565                 570                 575

Ala Ala Ala Pro His Ser Thr Ser Leu Ser Leu Ser Pro Trp Gln Ala
            580                 585                 590

Gly Val Tyr Lys Leu Arg
        595

<210> SEQ ID NO 19
<211> LENGTH: 471
<212> TYPE: DNA
<213> ORGANISM: Enterobacter sp.
<220> FEATURE:
<221> NAME/KEY: CDS
<222> LOCATION: (1)..(471)
<223> OTHER INFORMATION: coding for fragment of sucrose isomerase

<400> SEQUENCE: 19 gtt ttt tat cag atc tat cct cgc tca ttt aaa gac acc aat gat gat      48
Val Phe Tyr Gln Ile Tyr Pro Arg Ser Phe Lys Asp Thr Asn Asp Asp
 1               5                  10                  15 ggc att ggc gat att cgc ggt att att gaa aag ctg gac tat ctg aaa      96
Gly Ile Gly Asp Ile Arg Gly Ile Ile Glu Lys Leu Asp Tyr Leu Lys
            20                  25                  30 tcg ctc ggt att gac gct atc tgg atc aat ccc cat tac gac tct ccg     144
Ser Leu Gly Ile Asp Ala Ile Trp Ile Asn Pro His Tyr Asp Ser Pro
        35                  40                  45 aac acc gat aac ggc tat gac atc agt aat tat cgt cag ata atg aaa     192
Asn Thr Asp Asn Gly Tyr Asp Ile Ser Asn Tyr Arg Gln Ile Met Lys
    50                  55                  60 gag tat ggc aca atg gag gat ttt gat agc ctt gtt gcc gaa atg aaa     240
Glu Tyr Gly Thr Met Glu Asp Phe Asp Ser Leu Val Ala Glu Met Lys
65                  70                  75                  80 aaa cga aat atg cgc tta atg atc gac gtg gtc att aac cat acc agt     288
Lys Arg Asn Met Arg Leu Met Ile Asp Val Val Ile Asn His Thr Ser
                85                  90                  95 gat caa cac ccg tgg ttt att cag agt aaa agc gat aaa aac aac cct     336
Asp Gln His Pro Trp Phe Ile Gln Ser Lys Ser Asp Lys Asn Asn Pro
            100                 105                 110 tat cgt gac tat tat ttc tgg cgt gac gga aaa gat aat cag cca cct     384
Tyr Arg Asp Tyr Tyr Phe Trp Arg Asp Gly Lys Asp Asn Gln Pro Pro
        115                 120                 125 aat aat tac ccc tca ttt ttc ggc ggc tcg gca tgg caa aaa gat gca     432
Asn Asn Tyr Pro Ser Phe Phe Gly Gly Ser Ala Trp Gln Lys Asp Ala
```

-continued

```
             130                 135                 140
aag tca gga cag tac tat tta cac tat ttt gcc aga cag                    471
Lys Ser Gly Gln Tyr Tyr Leu His Tyr Phe Ala Arg Gln
145                 150                 155

<210> SEQ ID NO 20
<211> LENGTH: 157
<212> TYPE: PRT
<213> ORGANISM: Enterobacter sp.

<400> SEQUENCE: 20

Val Phe Tyr Gln Ile Tyr Pro Arg Ser Phe Lys Asp Thr Asn Asp Asp
  1               5                  10                  15

Gly Ile Gly Asp Ile Arg Gly Ile Ile Glu Lys Leu Asp Tyr Leu Lys
             20                  25                  30

Ser Leu Gly Ile Asp Ala Ile Trp Ile Asn Pro His Tyr Asp Ser Pro
         35                  40                  45

Asn Thr Asp Asn Gly Tyr Asp Ile Ser Asn Tyr Arg Gln Ile Met Lys
     50                  55                  60

Glu Tyr Gly Thr Met Glu Asp Phe Asp Ser Leu Val Ala Glu Met Lys
 65                  70                  75                  80

Lys Arg Asn Met Arg Leu Met Ile Asp Val Val Ile Asn His Thr Ser
                 85                  90                  95

Asp Gln His Pro Trp Phe Ile Gln Ser Lys Ser Asp Lys Asn Asn Pro
            100                 105                 110

Tyr Arg Asp Tyr Tyr Phe Trp Arg Asp Gly Lys Asp Asn Gln Pro Pro
        115                 120                 125

Asn Asn Tyr Pro Ser Phe Phe Gly Gly Ser Ala Trp Gln Lys Asp Ala
    130                 135                 140

Lys Ser Gly Gln Tyr Tyr Leu His Tyr Phe Ala Arg Gln
145                 150                 155

<210> SEQ ID NO 21
<211> LENGTH: 1782
<212> TYPE: DNA
<213> ORGANISM: Pseudomonas mesoacidophila MX45
<220> FEATURE:
<221> NAME/KEY: misc_feature
<222> LOCATION: (1237)..(1331)
<223> OTHER INFORMATION: n is a, c, g, or t
<220> FEATURE:
<221> NAME/KEY: CDS
<222> LOCATION: (1)..(1779)
<223> OTHER INFORMATION: coding for sucrose isomerase

<400> SEQUENCE: 21 atg ctt atg aag aga tta ttc gcc gcg tct ctg atg ctt gct ttt tca     48
Met Leu Met Lys Arg Leu Phe Ala Ala Ser Leu Met Leu Ala Phe Ser
  1               5                  10                  15 agc gtc tcc tct gtg agg gct gag gag gcc gta aag ccg ggc gcg cca     96
Ser Val Ser Ser Val Arg Ala Glu Glu Ala Val Lys Pro Gly Ala Pro
             20                  25                  30 tgg tgg aaa agt gct gtc ttc tat cag gtc tat ccg cgc tcg ttc aag    144
Trp Trp Lys Ser Ala Val Phe Tyr Gln Val Tyr Pro Arg Ser Phe Lys
         35                  40                  45 gat acc aac ggt gat ggg atc ggc gat ttc aaa gga ctg acg gag aag    192
Asp Thr Asn Gly Asp Gly Ile Gly Asp Phe Lys Gly Leu Thr Glu Lys
     50                  55                  60 ctc gac tat ctc aag ggg ctc ggc ata gac gcc atc tgg atc aat cca    240
Leu Asp Tyr Leu Lys Gly Leu Gly Ile Asp Ala Ile Trp Ile Asn Pro
 65                  70                  75                  80
```

```
cat tac gcg tct ccc aac acc gat aat ggc tac gat atc agc gac tat        288
His Tyr Ala Ser Pro Asn Thr Asp Asn Gly Tyr Asp Ile Ser Asp Tyr
                 85                  90                  95 cga gag gtc atg aag gaa tat ggg acg atg gag gac ttc gat cgt ctg        336
Arg Glu Val Met Lys Glu Tyr Gly Thr Met Glu Asp Phe Asp Arg Leu
            100                 105                 110 atg gct gag ttg aag aag cgc ggc atg cgg ctc atg gtt gat gtc gtg        384
Met Ala Glu Leu Lys Lys Arg Gly Met Arg Leu Met Val Asp Val Val
                115                 120                 125 atc aac cat tcg agt gac caa cac gaa tgg ttc aag agc agc cgg gcc        432
Ile Asn His Ser Ser Asp Gln His Glu Trp Phe Lys Ser Ser Arg Ala
        130                 135                 140 tcc aaa gac aat ccc tac cgt gac tat tat ttc tgg cgt gac ggc aaa        480
Ser Lys Asp Asn Pro Tyr Arg Asp Tyr Tyr Phe Trp Arg Asp Gly Lys
145                 150                 155                 160 gac ggt cac gag cca aac aat tac cct tcc ttc ttc ggc ggt tcg gca        528
Asp Gly His Glu Pro Asn Asn Tyr Pro Ser Phe Phe Gly Gly Ser Ala
                165                 170                 175 tgg gag aag gac ccc gta acc ggg caa tat tac ctg cat tat ttc ggt        576
Trp Glu Lys Asp Pro Val Thr Gly Gln Tyr Tyr Leu His Tyr Phe Gly
                180                 185                 190 cgt cag cag cca gat ctg aac tgg gac acg ccg aag ctt cgc gag gaa        624
Arg Gln Gln Pro Asp Leu Asn Trp Asp Thr Pro Lys Leu Arg Glu Glu
            195                 200                 205 ctc tat gcg atg ctg cgg ttc tgg ctc gac aag ggc gta tca ggc atg        672
Leu Tyr Ala Met Leu Arg Phe Trp Leu Asp Lys Gly Val Ser Gly Met
        210                 215                 220 cgg ttc gat acg gtg gct acc tac tcg aag aca ccg ggt ttc ccg gat        720
Arg Phe Asp Thr Val Ala Thr Tyr Ser Lys Thr Pro Gly Phe Pro Asp
225                 230                 235                 240 ctg aca ccg gag cag atg aag aac ttc gcg gag gcc tat acc cag ggg        768
Leu Thr Pro Glu Gln Met Lys Asn Phe Ala Glu Ala Tyr Thr Gln Gly
                245                 250                 255 ccg aac ctt cat cgt tac ctg cag gaa atg cac gag aag gtc ttc gat        816
Pro Asn Leu His Arg Tyr Leu Gln Glu Met His Glu Lys Val Phe Asp
            260                 265                 270 cat tat gac gcg gtc acg gcc ggc gaa atc ttc ggc gct ccg ctc aat        864
His Tyr Asp Ala Val Thr Ala Gly Glu Ile Phe Gly Ala Pro Leu Asn
        275                 280                 285 caa gtg ccg ctg ttc atc gac agc cgg agg aaa gag ctg gat atg gct        912
Gln Val Pro Leu Phe Ile Asp Ser Arg Arg Lys Glu Leu Asp Met Ala
        290                 295                 300 ttc acc ttc gat ctg atc cgt tat gat cgc gca ctg gat cgt tgg cat        960
Phe Thr Phe Asp Leu Ile Arg Tyr Asp Arg Ala Leu Asp Arg Trp His
305                 310                 315                 320 acc att ccg cgt acc tta gcg gac ttc cgt caa acg atc gat aag gtc       1008
Thr Ile Pro Arg Thr Leu Ala Asp Phe Arg Gln Thr Ile Asp Lys Val
                325                 330                 335 gac gcc atc gcg ggc gaa tat ggc tgg aac acg ttc ttc ctc ggc aat       1056
Asp Ala Ile Ala Gly Glu Tyr Gly Trp Asn Thr Phe Phe Leu Gly Asn
            340                 345                 350 cac gac aat ccc cgt gcg gta tcg cat ttt ggt gac gat cgg ccg caa       1104
His Asp Asn Pro Arg Ala Val Ser His Phe Gly Asp Asp Arg Pro Gln
        355                 360                 365 tgg cgc gaa gcc tcg gcc aag gct ctg gcc acc gtc acc ttg acc cag       1152
Trp Arg Glu Ala Ser Ala Lys Ala Leu Ala Thr Val Thr Leu Thr Gln
        370                 375                 380 cga gga acg ccg ttc atc ttc caa gga gat gaa ctc gga atg acc aac       1200
Arg Gly Thr Pro Phe Ile Phe Gln Gly Asp Glu Leu Gly Met Thr Asn
```

```
                385                 390                 395                 400
tac ccc ttc aag acg ctg cag gac ttt gat gat atc nnn nnn nnn nnn           1248
Tyr Pro Phe Lys Thr Leu Gln Asp Phe Asp Asp Ile Xaa Xaa Xaa Xaa
                405                 410                 415 nnn nnn nnn nnn nnn nnn nnn nnn nnn nnn nnn nnn nnn nnn nnn nnn           1296
Xaa Xaa Xaa Xaa Xaa Xaa Xaa Xaa Xaa Xaa Xaa Xaa Xaa Xaa Xaa Xaa
            420                 425                 430 nnn nnn nnn nnn nnn nnn nnn nnn nnn nnn nnt gtg gcg ttg act               1344
Xaa Xaa Xaa Xaa Xaa Xaa Xaa Xaa Xaa Xaa Xaa Val Ala Leu Thr
        435                 440                 445 agc cga gca aac gcc cgc acg ccc ttt caa tgg gat gac agt gct aat           1392
Ser Arg Ala Asn Ala Arg Thr Pro Phe Gln Trp Asp Asp Ser Ala Asn
450                 455                 460 gcg gga ttc aca act ggc aag cct tgg cta aag gtc aat cca aac tac           1440
Ala Gly Phe Thr Thr Gly Lys Pro Trp Leu Lys Val Asn Pro Asn Tyr
465                 470                 475                 480 act gag atc aac gcc gcg cgg gaa att ggc gat cct aaa tcg gtc tac           1488
Thr Glu Ile Asn Ala Ala Arg Glu Ile Gly Asp Pro Lys Ser Val Tyr
                485                 490                 495 agc ttt tac cgc aac ctg atc tca atc cgg cat gaa act ccc gct ctt           1536
Ser Phe Tyr Arg Asn Leu Ile Ser Ile Arg His Glu Thr Pro Ala Leu
            500                 505                 510 tcg acc ggg agc tat cgc gac atc gat ccg agt aat gcc gat gtc tat           1584
Ser Thr Gly Ser Tyr Arg Asp Ile Asp Pro Ser Asn Ala Asp Val Tyr
        515                 520                 525 gcc tat acg cgc agc cag gat ggc gag acc tat ctg gtc gta gtc aac           1632
Ala Tyr Thr Arg Ser Gln Asp Gly Glu Thr Tyr Leu Val Val Val Asn
530                 535                 540 ttc aag gca gag cca agg agt ttc acg ctt ccg gac ggc atg cat att           1680
Phe Lys Ala Glu Pro Arg Ser Phe Thr Leu Pro Asp Gly Met His Ile
545                 550                 555                 560 gcc gaa acc ctg att gag agc agt tcg cca gca gct ccg gcg gcg ggg           1728
Ala Glu Thr Leu Ile Glu Ser Ser Ser Pro Ala Ala Pro Ala Ala Gly
                565                 570                 575 gct gca agc ctt gag ctg cag cct tgg cag tcc ggc atc tac aag gtg           1776
Ala Ala Ser Leu Glu Leu Gln Pro Trp Gln Ser Gly Ile Tyr Lys Val
            580                 585                 590 aag taa                                                                    1782
Lys <210> SEQ ID NO 22
<211> LENGTH: 593
<212> TYPE: PRT
<213> ORGANISM: Pseudomonas mesoacidophila MX45
<220> FEATURE:
<221> NAME/KEY: misc_feature
<222> LOCATION: (413)..(443)
<223> OTHER INFORMATION: The 'Xaa' at locations 413-443 stands for Lys,
      Asn, Arg, Ser, Thr, Ile, Met, Glu, Asp, Gly, Ala, Val, Gln, His,
      Pro, Leu, Tyr, Trp, Cys, or Phe.
<220> FEATURE:
<221> NAME/KEY: misc_feature
<222> LOCATION: (444)..(444)
<223> OTHER INFORMATION: The 'Xaa' at location 444 stands for Asn, Ser,
      Thr, Ile, Asp, Gly, Ala, Val, His, Arg, Pro, Leu, Tyr, Cys, or
      Phe.

<400> SEQUENCE: 22

Met Leu Met Lys Arg Leu Phe Ala Ala Ser Leu Met Leu Ala Phe Ser
 1               5                  10                  15

Ser Val Ser Ser Val Arg Ala Glu Glu Ala Val Lys Pro Gly Ala Pro
            20                  25                  30
```

```
Trp Trp Lys Ser Ala Val Phe Tyr Gln Val Tyr Pro Arg Ser Phe Lys
         35                  40                  45

Asp Thr Asn Gly Asp Gly Ile Gly Asp Phe Lys Gly Leu Thr Glu Lys
 50                  55                  60

Leu Asp Tyr Leu Lys Gly Leu Gly Ile Asp Ala Ile Trp Ile Asn Pro
 65                  70                  75                  80

His Tyr Ala Ser Pro Asn Thr Asp Asn Gly Tyr Asp Ile Ser Asp Tyr
                 85                  90                  95

Arg Glu Val Met Lys Glu Tyr Gly Thr Met Glu Asp Phe Asp Arg Leu
                100                 105                 110

Met Ala Glu Leu Lys Lys Arg Gly Met Arg Leu Met Val Asp Val Val
            115                 120                 125

Ile Asn His Ser Asp Gln His Glu Trp Phe Lys Ser Ser Arg Ala
130                 135                 140

Ser Lys Asp Asn Pro Tyr Arg Asp Tyr Phe Trp Arg Asp Gly Lys
145                 150                 155                 160

Asp Gly His Glu Pro Asn Asn Tyr Pro Ser Phe Gly Gly Ser Ala
                165                 170                 175

Trp Glu Lys Asp Pro Val Thr Gly Gln Tyr Tyr Leu His Tyr Phe Gly
                180                 185                 190

Arg Gln Gln Pro Asp Leu Asn Trp Asp Thr Pro Lys Leu Arg Glu Glu
            195                 200                 205

Leu Tyr Ala Met Leu Arg Phe Trp Leu Asp Lys Gly Val Ser Gly Met
        210                 215                 220

Arg Phe Asp Thr Val Ala Thr Tyr Ser Lys Thr Pro Gly Phe Pro Asp
225                 230                 235                 240

Leu Thr Pro Glu Gln Met Lys Asn Phe Ala Glu Ala Tyr Thr Gln Gly
                245                 250                 255

Pro Asn Leu His Arg Tyr Leu Gln Glu Met His Glu Lys Val Phe Asp
                260                 265                 270

His Tyr Asp Ala Val Thr Ala Gly Glu Ile Phe Gly Ala Pro Leu Asn
            275                 280                 285

Gln Val Pro Leu Phe Ile Asp Ser Arg Arg Lys Glu Leu Asp Met Ala
        290                 295                 300

Phe Thr Phe Asp Leu Ile Arg Tyr Asp Arg Ala Leu Asp Arg Trp His
305                 310                 315                 320

Thr Ile Pro Arg Thr Leu Ala Asp Phe Arg Gln Thr Ile Asp Lys Val
                325                 330                 335

Asp Ala Ile Ala Gly Glu Tyr Gly Trp Asn Thr Phe Phe Leu Gly Asn
            340                 345                 350

His Asp Asn Pro Arg Ala Val Ser His Phe Gly Asp Asp Arg Pro Gln
        355                 360                 365

Trp Arg Glu Ala Ser Ala Lys Ala Leu Ala Thr Val Thr Leu Thr Gln
370                 375                 380

Arg Gly Thr Pro Phe Ile Phe Gln Gly Asp Glu Leu Gly Met Thr Asn
385                 390                 395                 400

Tyr Pro Phe Lys Thr Leu Gln Asp Phe Asp Asp Ile Xaa Xaa Xaa Xaa
                405                 410                 415

Xaa Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Val Ala Leu Thr
            435                 440                 445

Ser Arg Ala Asn Ala Arg Thr Pro Phe Gln Trp Asp Asp Ser Ala Asn
```

```
          450                 455                 460
Ala Gly Phe Thr Thr Gly Lys Pro Trp Leu Lys Val Asn Pro Asn Tyr
465                 470                 475                 480

Thr Glu Ile Asn Ala Ala Arg Glu Ile Gly Asp Pro Lys Ser Val Tyr
                485                 490                 495

Ser Phe Tyr Arg Asn Leu Ile Ser Ile Arg His Glu Thr Pro Ala Leu
                500                 505                 510

Ser Thr Gly Ser Tyr Arg Asp Ile Asp Pro Ser Asn Ala Asp Val Tyr
                515                 520                 525

Ala Tyr Thr Arg Ser Gln Asp Gly Glu Thr Tyr Leu Val Val Val Asn
                530                 535                 540

Phe Lys Ala Glu Pro Arg Ser Phe Thr Leu Pro Asp Gly Met His Ile
545                 550                 555                 560

Ala Glu Thr Leu Ile Glu Ser Ser Ser Pro Ala Ala Pro Ala Ala Gly
                565                 570                 575

Ala Ala Ser Leu Glu Leu Gln Pro Trp Gln Ser Gly Ile Tyr Lys Val
                580                 585                 590

Lys

<210> SEQ ID NO 23
<211> LENGTH: 1417
<212> TYPE: DNA
<213> ORGANISM: Lycopersicon esculentum
<220> FEATURE:
<221> NAME/KEY: promoter
<222> LOCATION: (1)..(1417)
<223> OTHER INFORMATION: promoter of lemmi9

<400> SEQUENCE: 23
ataatttaac catctagaga tccacaaatc atgtttccat atcatggtag tagttggtgc      60
tacgaagtat ctataaatta ttgagaaata cctggtggaa tcccaagtga aacggaaagg     120
cccttactta ttaaataaaa aaacatttga caatagaaaa ttgagaccaa tctgcatatg     180
aaacatcagg atccccacat ttcacaaatt ttacaagtta attaagccct actctgtcca     240
tatggaactt ttctgcactt ccacgcacca acgaatatgc tgaaaattga tgttttagat     300
gtgtacgaat aaagcaatca agaacgcgg gcgcaacgcg cgctggagac actgccattc     360
atgtgtgcct aacgtgtttt ctttagtcat tacgctccta ctaccgactc aatatatatt     420
aactatagta ttttttattt atgacgagaa acgtaatttt aaatgtagat atattttaac     480
aagctatgat aattacatct tgttgccgta gtcataaatg acacaaatta aggtttgatt     540
ttcgtccact tctaagattt cttgttctaa tactagtata tttctgattt aaaaagttat     600
ttagtttttt ttgaattagc tgataaatgc caaaaactga aaattaaagt acttttaat      660 tttataaaaa taatatcatg gaaattaaaa cgagaaatta atgaaaagt agaagattgc      720 tttgccataa tatagtgtta cttttcgtat tattttatta agcgtaaaat tacataaagg     780
tatccgtgct taaatttcta gcttgagagc attttttgaa gcaaaagttt cgataaatca     840
agttttaata taaaattaca atcatcattt ctaattatat taattcttta aaaataaaat     900
taaaaaaata tatacaataa ttgaagctcg gataaattaa aatatgtaac tattaaatat     960
tactcggata tattaaatat tattcgatta tattaatatg tagctcaaaa tatattaaat    1020
aataatacaa atatattaat atatgtaaat catatacatt aaaaactatc ttaaatatat    1080
aatatgcagc tgtaatatat taacccagat acataagcac ctcgagtaca ttaaacaaat    1140
aaaagaattt aaaaataata aaaataagtg aaagcaataa attgtatatt tctataattt    1200
```

```
atcccttat taatactaaa taaagttaga gaacctaaac aggaagcaca attatgacac      1260
gaggagagaa tagcgcgtca attgtgaccc tttacgcgga agtatatgta ataaatagta      1320
gactcttttt ctatatttgt atatcccata acaagagcag agatattcgt ttagcacaaa      1380
acaggcatac tattcaattc cctttcgttc cagaagc                               1417

<210> SEQ ID NO 24
<211> LENGTH: 374
<212> TYPE: DNA
<213> ORGANISM: Nicotiana tabacum
<220> FEATURE:
<221> NAME/KEY: promoter
<222> LOCATION: (1)..(374)
<223> OTHER INFORMATION: promoter of delta-0.3TobRB7

<400> SEQUENCE: 24
agcttatcta aacaaagttt taaattcatt tcttaaacgt ccattacaat gtaatataac        60
ttagtcgtct caattaaacc attaatgtga aatataaatc aaaaaaagcc aaagggcggt      120
gggacggcgc caatcatttg tcctagtcca ctcaaataag gcccatggtc ggcaaaacca      180
aacacaaaat gtgttatttt taatttttc ctcttttatt gttaaagttg caaaatgtgt       240 tattttggt aagaccctat ggatatataa agacaggtta tgtgaaactt ggaaaaccat       300
caagttttaa gcaaaaccct cttaagaact taaattgagc ttcttttggg gcattttct       360 agtgagaact aaaa                                                        374

<210> SEQ ID NO 25
<211> LENGTH: 27
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 25
ggatccggta ccgttcagca atcaaat                                          27

<210> SEQ ID NO 26
<211> LENGTH: 23
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 26
gtcgacgtct tgccaaaaac ctt                                              23

<210> SEQ ID NO 27
<211> LENGTH: 25
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 27
gtcgacctac gtgattaagt ttata                                            25

<210> SEQ ID NO 28
<211> LENGTH: 28
<212> TYPE: DNA
<213> ORGANISM: Artificial sequence
```

```
<220> FEATURE:
<223> OTHER INFORMATION: Description of the artificial sequence:
      oligonucleotide primer

<400> SEQUENCE: 28
atcgaattca taatttaacc atctagag                                            28

<210> SEQ ID NO 29
<211> LENGTH: 28
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 29
atcggtacct gcttctggaa cgaaaggg                                            28

<210> SEQ ID NO 30
<211> LENGTH: 34
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 30
ggaattcagc ttatctaaac aaagttttaa attc                                     34

<210> SEQ ID NO 31
<211> LENGTH: 30
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 31
gggtaccagt tctcactaga aaaatgcccc                                          30

<210> SEQ ID NO 32
<211> LENGTH: 461
<212> TYPE: DNA
<213> ORGANISM: Wheat dwarf virus
<220> FEATURE:
<221> NAME/KEY: promoter
<222> LOCATION: (1)..(461)
<223> OTHER INFORMATION: V-sense promoter from Wheat Dwarf Virus

<400> SEQUENCE: 32
ccggcaggtc cttagcgaaa aaacggggtg tgccagaaaa ctctatgctc tacccctgcgt        60 ggaggtgtga attctgcaca ctgctaatgc aatgtgtcca atgctttata tagggcaggt       120
tttggcggga gaacagggcc cttgtgttcc cacgggagcg tagcgtatcg tgtgggccct       180
gttcggtgtg tggtcggggg gcctccacgc gggttataat attacccccgc gtggtggccc     240 ccgacgcgca ctcggctttt cgtgagtgcg cggaggcttt tggaccacat cttttctgac       300
cactttcgtg gaatatgttg atttatcaca cttttgacgc ggaaatctgt gccatgcctt       360
agcttataag gaagtgcgtg gtagcccatc tcgatggagc aggcaatagc ccccccgctt       420
cctatacggg actatcaata ccagacccct tccattcccg g                           461

<210> SEQ ID NO 33
<211> LENGTH: 1173
<212> TYPE: DNA
```

<213> ORGANISM: Maize streak virus
<220> FEATURE:
<221> NAME/KEY: promoter
<222> LOCATION: (1)..(1173)
<223> OTHER INFORMATION: V-sense promotor from Maize Streak Virus

<400> SEQUENCE: 33

| | | | | | |
|---|---|---|---|---|---|
| aagcttattt | gcagagtatt | caaaatactg | caattttgtg | gaccaatcaa | agggaagctc | 60 |
| tttctggatc | atgagaggt | actcttcttt | ggaagtagcg | tgtgaaataa | tgtctcgcat | 120 |
| tatttcatct | ttagaaggct | ttttttcctt | tacctctgaa | tcagattttc | cgaggaaggg | 180 |
| ggacttccta | ggaatgaaag | tacctctctc | aaacacagcc | agaggttcct | tgagaatgta | 240 |
| atccctcacc | ctgtttactg | acttggcact | ctgaatattt | gggtgaaacc | catttatatc | 300 |
| aaagaacctt | gagtcagata | tccttaccgg | cttctctgtc | tgaagcaatg | catgtaaatg | 360 |
| caaacttcca | tctttatgtg | cctctcgggc | acatagaatg | tatttgggaa | tccaacgaac | 420 |
| aacgagctcc | cagatcatct | gacaggcgat | ttcaggattt | tctggacact | ttggataggt | 480 |
| taggaacgtg | ttagcgttcc | ggtgtgagaa | ctgacggttg | gatgaggagg | aggccattgc | 540 |
| cgacgacgga | ggttgaggct | gagggatggc | agactgggag | ctccaaactc | tatagtatac | 600 |
| ccgtgcgcct | tcgcctcgag | gcgaaatccg | ccgctccctt | gtcttgtagt | ggttgcaaat | 660 |
| gggccggacc | gggccggccc | agcaggaaaa | gaaggcgcgc | actaatatta | ccgcgccttc | 720 |
| ttttcctgcg | agggcccggt | agggtcgacc | ccgagcgatt | tgatgtaaag | tttggtcctg | 780 |
| ctttgtatga | tttatctaaa | gcagcccatt | ctaaagaatc | cggtcccggt | cactataaat | 840 |
| tgcctaacaa | gtgcgattca | ttcatggatc | cacagaacgc | cctgtattat | cagccgcggg | 900 |
| tacccacagc | agctccgaca | tccggaggag | tgccgtggag | tcgcgtaggc | gaggtagcta | 960 |
| ttttgagctt | tgttgcattg | atttgctttt | acctgcttta | cctttgggtg | ctgagagacc | 1020 |
| ttatcttagt | tctgaaggct | cgacaaggca | gatccacgga | ggagctgata | tttggtggac | 1080 |
| aagctgtgga | taggagcaac | cctatcccta | atataccagc | accaccaagt | cagggcaatc | 1140 |
| ccgggccatt | tgttccatcg | actctagtcg | acc | | | 1173 |

<210> SEQ ID NO 34
<211> LENGTH: 353
<212> TYPE: DNA
<213> ORGANISM: Pepper huasteco virus
<220> FEATURE:
<221> NAME/KEY: promoter
<222> LOCATION: (1)..(353)
<223> OTHER INFORMATION: V-sense promoter from Pepper huasteco virus

<400> SEQUENCE: 34

| | | | | | |
|---|---|---|---|---|---|
| catatttgta | ataagagagg | tgtacaccga | ttggagctct | ttaacctggg | cttattgtat | 60 |
| cggtgtattg | gtagccaata | tatagtatat | gggagttatc | taggatcttc | gtacacgtga | 120 |
| gggccatccg | ttataatatt | accggatggc | cgaccgctta | ccttatctat | ccgtactgct | 180 |
| ttatttgaat | taaagatgtt | acttttatgc | tatccaatga | agcgtagcgt | ctgggaagct | 240 |
| tagttatcag | ttccagacgt | ggggaccaag | tagtgtatga | ccactttatt | gactgtcagc | 300 |
| tttataaatt | gaaattaaaa | cataagtggt | ccatgtacct | ttaattcaaa | atg | 353 |

<210> SEQ ID NO 35
<211> LENGTH: 1803
<212> TYPE: DNA
<213> ORGANISM: Serratia plymuthica
<220> FEATURE:
<221> NAME/KEY: CDS
<222> LOCATION: (1)..(1800)
<223> OTHER INFORMATION: coding for sucrose isomerase

<400> SEQUENCE: 35

| | | | | | | | | | | | | | | | | |
|---|---|---|---|---|---|---|---|---|---|---|---|---|---|---|---|---|
| atg | ccc | cgt | caa | gga | ttg | aaa | act | gca | cta | gcg | att | ttt | cta | acc | aca | 48 |
| Met | Pro | Arg | Gln | Gly | Leu | Lys | Thr | Ala | Leu | Ala | Ile | Phe | Leu | Thr | Thr | |
| 1 | | | | 5 | | | | | 10 | | | | | 15 | | |
| tca | tta | agc | gtc | tca | tgc | cag | caa | gcc | tta | ggt | acg | caa | caa | ccc | ttg | 96 |
| Ser | Leu | Ser | Val | Ser | Cys | Gln | Gln | Ala | Leu | Gly | Thr | Gln | Gln | Pro | Leu | |
| | | | 20 | | | | | 25 | | | | | 30 | | | |
| ctt | aac | gaa | aag | agt | atc | gaa | cag | tcg | aaa | acc | ata | cct | aaa | tgg | tgg | 144 |
| Leu | Asn | Glu | Lys | Ser | Ile | Glu | Gln | Ser | Lys | Thr | Ile | Pro | Lys | Trp | Trp | |
| | | | 35 | | | | | 40 | | | | | 45 | | | |
| aag | gag | gct | gtt | ttt | tat | cag | gtg | tat | ccg | cgt | tcc | ttt | aaa | gac | act | 192 |
| Lys | Glu | Ala | Val | Phe | Tyr | Gln | Val | Tyr | Pro | Arg | Ser | Phe | Lys | Asp | Thr | |
| | 50 | | | | | 55 | | | | | 60 | | | | | |
| aac | ggg | gat | ggt | atc | ggg | gat | att | aaa | ggc | atc | ata | gaa | aaa | tta | gac | 240 |
| Asn | Gly | Asp | Gly | Ile | Gly | Asp | Ile | Lys | Gly | Ile | Ile | Glu | Lys | Leu | Asp | |
| 65 | | | | | 70 | | | | | 75 | | | | | 80 | |
| tat | tta | aaa | gct | ttg | ggg | att | gat | gcc | att | tgg | atc | aac | cca | cat | tat | 288 |
| Tyr | Leu | Lys | Ala | Leu | Gly | Ile | Asp | Ala | Ile | Trp | Ile | Asn | Pro | His | Tyr | |
| | | | | 85 | | | | | 90 | | | | | 95 | | |
| gac | tcc | ccg | aac | acg | gat | aat | ggt | tac | gat | ata | cgt | gat | tat | cga | aaa | 336 |
| Asp | Ser | Pro | Asn | Thr | Asp | Asn | Gly | Tyr | Asp | Ile | Arg | Asp | Tyr | Arg | Lys | |
| | | | 100 | | | | | 105 | | | | | 110 | | | |
| atc | atg | aaa | gaa | tat | ggc | acg | atg | gag | gat | ttt | gac | cgc | ctg | att | tct | 384 |
| Ile | Met | Lys | Glu | Tyr | Gly | Thr | Met | Glu | Asp | Phe | Asp | Arg | Leu | Ile | Ser | |
| | | | 115 | | | | | 120 | | | | | 125 | | | |
| gaa | atg | aaa | aaa | cgt | aac | atg | cgg | ttg | atg | att | gat | gtg | gtc | atc | aac | 432 |
| Glu | Met | Lys | Lys | Arg | Asn | Met | Arg | Leu | Met | Ile | Asp | Val | Val | Ile | Asn | |
| | 130 | | | | | 135 | | | | | 140 | | | | | |
| cac | acc | agc | gat | caa | aac | gaa | tgg | ttt | gtt | aaa | agt | aaa | agc | agt | aag | 480 |
| His | Thr | Ser | Asp | Gln | Asn | Glu | Trp | Phe | Val | Lys | Ser | Lys | Ser | Ser | Lys | |
| 145 | | | | | 150 | | | | | 155 | | | | | 160 | |
| gat | aat | cct | tat | cgt | ggc | tat | tac | ttc | tgg | aaa | gat | gct | aaa | gaa | ggg | 528 |
| Asp | Asn | Pro | Tyr | Arg | Gly | Tyr | Tyr | Phe | Trp | Lys | Asp | Ala | Lys | Glu | Gly | |
| | | | | 165 | | | | | 170 | | | | | 175 | | |
| cag | gcg | cct | aat | aat | tac | cct | tca | ttc | ttt | ggt | ggc | tcg | gcg | tgg | caa | 576 |
| Gln | Ala | Pro | Asn | Asn | Tyr | Pro | Ser | Phe | Phe | Gly | Gly | Ser | Ala | Trp | Gln | |
| | | | 180 | | | | | 185 | | | | | 190 | | | |
| aaa | gat | gaa | aag | acc | aat | caa | tac | tac | ctg | cac | tat | ttt | gct | aaa | caa | 624 |
| Lys | Asp | Glu | Lys | Thr | Asn | Gln | Tyr | Tyr | Leu | His | Tyr | Phe | Ala | Lys | Gln | |
| | | | 195 | | | | | 200 | | | | | 205 | | | |
| cag | cct | gac | cta | aac | tgg | gat | aac | ccc | aaa | gtc | cgt | caa | gat | ctt | tat | 672 |
| Gln | Pro | Asp | Leu | Asn | Trp | Asp | Asn | Pro | Lys | Val | Arg | Gln | Asp | Leu | Tyr | |
| | 210 | | | | | 215 | | | | | 220 | | | | | |
| gca | atg | ttg | cgt | ttc | tgg | tta | gat | aaa | ggc | gtg | tct | ggt | tta | cgc | ttt | 720 |
| Ala | Met | Leu | Arg | Phe | Trp | Leu | Asp | Lys | Gly | Val | Ser | Gly | Leu | Arg | Phe | |
| 225 | | | | | 230 | | | | | 235 | | | | | 240 | |
| gat | acg | gta | gcg | acc | tac | tca | aaa | att | ccg | gac | ttc | cca | aat | ctc | acc | 768 |
| Asp | Thr | Val | Ala | Thr | Tyr | Ser | Lys | Ile | Pro | Asp | Phe | Pro | Asn | Leu | Thr | |
| | | | | 245 | | | | | 250 | | | | | 255 | | |
| caa | caa | cag | ctg | aag | aat | ttt | gca | gct | gag | tat | acc | aag | ggc | cct | aat | 816 |
| Gln | Gln | Gln | Leu | Lys | Asn | Phe | Ala | Ala | Glu | Tyr | Thr | Lys | Gly | Pro | Asn | |
| | | | 260 | | | | | 265 | | | | | 270 | | | |
| att | cat | cgt | tac | gtc | aat | gaa | atg | aat | aga | gaa | gtt | ttg | tct | cat | tac | 864 |
| Ile | His | Arg | Tyr | Val | Asn | Glu | Met | Asn | Arg | Glu | Val | Leu | Ser | His | Tyr | |
| | | | 275 | | | | | 280 | | | | | 285 | | | |
| gac | att | gcc | act | gcc | ggt | gaa | atc | ttt | ggc | gta | ccc | ttg | gat | caa | tcg | 912 |
| Asp | Ile | Ala | Thr | Ala | Gly | Glu | Ile | Phe | Gly | Val | Pro | Leu | Asp | Gln | Ser | |

```
                 290                 295                 300
ata aaa ttc ttc gat cgc cgt cgc gat gag ctg aac atc gca ttt acc      960
Ile Lys Phe Phe Asp Arg Arg Arg Asp Glu Leu Asn Ile Ala Phe Thr
305                 310                 315                 320 ttt gac tta atc aga ctc gat cga gac tct gat caa aga tgg cgt cga     1008
Phe Asp Leu Ile Arg Leu Asp Arg Asp Ser Asp Gln Arg Trp Arg Arg
                325                 330                 335 aaa gag tgg aaa ttg tcg caa ttc cga cag gtc atc gat aac gtt gac     1056
Lys Glu Trp Lys Leu Ser Gln Phe Arg Gln Val Ile Asp Asn Val Asp
        340                 345                 350 cgt act gcc ggc gaa tat ggt tgg aat gcc ttc ttc ttg gat aac cac     1104
Arg Thr Ala Gly Glu Tyr Gly Trp Asn Ala Phe Phe Leu Asp Asn His
                355                 360                 365 gac aat ccg cgc gct gtc tcc cac ttt ggc gat gat cgc cca caa tgg     1152
Asp Asn Pro Arg Ala Val Ser His Phe Gly Asp Asp Arg Pro Gln Trp
370                 375                 380 cgc gag cca tcg gct aaa gcg ctt gca acc ttg acg ctg act caa cga     1200
Arg Glu Pro Ser Ala Lys Ala Leu Ala Thr Leu Thr Leu Thr Gln Arg
385                 390                 395                 400 gca acg cct ttt att tat caa ggt tca gaa ttg ggc atg acc aat tac     1248
Ala Thr Pro Phe Ile Tyr Gln Gly Ser Glu Leu Gly Met Thr Asn Tyr
                405                 410                 415 ccc ttc aaa gct att gat gaa ttc gat gat att gag gtg aaa ggt ttt     1296
Pro Phe Lys Ala Ile Asp Glu Phe Asp Asp Ile Glu Val Lys Gly Phe
                420                 425                 430 tgg cat gac tac gtt gag aca gga aag gtg aaa gcc gac gag ttc ttg     1344
Trp His Asp Tyr Val Glu Thr Gly Lys Val Lys Ala Asp Glu Phe Leu
                435                 440                 445 caa aat gta cgc ctg acg agc agg gat aac agc cgg aca ccg ttc caa     1392
Gln Asn Val Arg Leu Thr Ser Arg Asp Asn Ser Arg Thr Pro Phe Gln
450                 455                 460 tgg gat acg agc aaa aat gca gga ttc acg agc gga aaa cct tgg ttc     1440
Trp Asp Thr Ser Lys Asn Ala Gly Phe Thr Ser Gly Lys Pro Trp Phe
465                 470                 475                 480 aag gtc aat cca aac tac cag gaa atc aat gcg gta agt caa gtc gca     1488
Lys Val Asn Pro Asn Tyr Gln Glu Ile Asn Ala Val Ser Gln Val Ala
                485                 490                 495 cag ccc gac tcg gta ttt aat tat tat cgt cag ttg atc aag ata agg     1536
Gln Pro Asp Ser Val Phe Asn Tyr Tyr Arg Gln Leu Ile Lys Ile Arg
            500                 505                 510 cat aac atc ccg gca ctg acc tat ggc aca tac acc gat ttg gat cct     1584
His Asn Ile Pro Ala Leu Thr Tyr Gly Thr Tyr Thr Asp Leu Asp Pro
            515                 520                 525 gca aat gat tcg gtc tac gcc tat aca cgc agc ctt ggg gcg gaa aaa     1632
Ala Asn Asp Ser Val Tyr Ala Tyr Thr Arg Ser Leu Gly Ala Glu Lys
530                 535                 540 tat ctt gtt gtc gtt aac ttc cag gaa caa gtg atg aga tat aaa tta     1680
Tyr Leu Val Val Val Asn Phe Gln Glu Gln Val Met Arg Tyr Lys Leu
545                 550                 555                 560 ccg gat aat cta tcc atc gag aaa gtg att ata gaa agc aac agc aaa     1728
Pro Asp Asn Leu Ser Ile Glu Lys Val Ile Ile Glu Ser Asn Ser Lys
                565                 570                 575 aac gtt gtg aaa aag aat gat tcc tta ctc gaa cta aaa cca tgg cag     1776
Asn Val Val Lys Lys Asn Asp Ser Leu Leu Glu Leu Lys Pro Trp Gln
            580                 585                 590 tca ggg gtt tat aaa cta aat caa taa                                 1803
Ser Gly Val Tyr Lys Leu Asn Gln
            595                 600
```

```
<210> SEQ ID NO 36
<211> LENGTH: 600
<212> TYPE: PRT
<213> ORGANISM: Serratia plymuthica

<400> SEQUENCE: 36
```

| | | | | | | | | | | | | | | | |
|---|---|---|---|---|---|---|---|---|---|---|---|---|---|---|---|
| Met | Pro | Arg | Gln | Gly | Leu | Lys | Thr | Ala | Leu | Ala | Ile | Phe | Leu | Thr | Thr |
| 1 | | | | 5 | | | | | 10 | | | | | 15 | |
| Ser | Leu | Ser | Val | Ser | Cys | Gln | Gln | Ala | Leu | Gly | Thr | Gln | Gln | Pro | Leu |
| | | | 20 | | | | | 25 | | | | | 30 | | |
| Leu | Asn | Glu | Lys | Ser | Ile | Glu | Gln | Ser | Lys | Thr | Ile | Pro | Lys | Trp | Trp |
| | | | | 35 | | | | | 40 | | | | | 45 | |
| Lys | Glu | Ala | Val | Phe | Tyr | Gln | Val | Tyr | Pro | Arg | Ser | Phe | Lys | Asp | Thr |
| | | 50 | | | | | 55 | | | | | 60 | | | |
| Asn | Gly | Asp | Gly | Ile | Gly | Asp | Ile | Lys | Gly | Ile | Ile | Glu | Lys | Leu | Asp |
| 65 | | | | | 70 | | | | | 75 | | | | | 80 |
| Tyr | Leu | Lys | Ala | Leu | Gly | Ile | Asp | Ala | Ile | Trp | Ile | Asn | Pro | His | Tyr |
| | | | | 85 | | | | | 90 | | | | | 95 | |
| Asp | Ser | Pro | Asn | Thr | Asp | Asn | Gly | Tyr | Asp | Ile | Arg | Asp | Tyr | Arg | Lys |
| | | | 100 | | | | | 105 | | | | | 110 | | |
| Ile | Met | Lys | Glu | Tyr | Gly | Thr | Met | Glu | Asp | Phe | Asp | Arg | Leu | Ile | Ser |
| | | | | 115 | | | | | 120 | | | | | 125 | |
| Glu | Met | Lys | Lys | Arg | Asn | Met | Arg | Leu | Met | Ile | Asp | Val | Val | Ile | Asn |
| | | 130 | | | | | 135 | | | | | 140 | | | |
| His | Thr | Ser | Asp | Gln | Asn | Glu | Trp | Phe | Val | Lys | Ser | Lys | Ser | Ser | Lys |
| 145 | | | | | 150 | | | | | 155 | | | | | 160 |
| Asp | Asn | Pro | Tyr | Arg | Gly | Tyr | Tyr | Phe | Trp | Lys | Asp | Ala | Lys | Glu | Gly |
| | | | | 165 | | | | | 170 | | | | | 175 | |
| Gln | Ala | Pro | Asn | Asn | Tyr | Pro | Ser | Phe | Phe | Gly | Gly | Ser | Ala | Trp | Gln |
| | | | 180 | | | | | 185 | | | | | 190 | | |
| Lys | Asp | Glu | Lys | Thr | Asn | Gln | Tyr | Tyr | Leu | His | Tyr | Phe | Ala | Lys | Gln |
| | | | | 195 | | | | | 200 | | | | | 205 | |
| Gln | Pro | Asp | Leu | Asn | Trp | Asp | Asn | Pro | Lys | Val | Arg | Gln | Asp | Leu | Tyr |
| | | 210 | | | | | 215 | | | | | 220 | | | |
| Ala | Met | Leu | Arg | Phe | Trp | Leu | Asp | Lys | Gly | Val | Ser | Gly | Leu | Arg | Phe |
| 225 | | | | | 230 | | | | | 235 | | | | | 240 |
| Asp | Thr | Val | Ala | Thr | Tyr | Ser | Lys | Ile | Pro | Asp | Phe | Pro | Asn | Leu | Thr |
| | | | | 245 | | | | | 250 | | | | | 255 | |
| Gln | Gln | Gln | Leu | Lys | Asn | Phe | Ala | Ala | Glu | Tyr | Thr | Lys | Gly | Pro | Asn |
| | | | 260 | | | | | 265 | | | | | 270 | | |
| Ile | His | Arg | Tyr | Val | Asn | Glu | Met | Asn | Arg | Glu | Val | Leu | Ser | His | Tyr |
| | | | | 275 | | | | | 280 | | | | | 285 | |
| Asp | Ile | Ala | Thr | Ala | Gly | Glu | Ile | Phe | Gly | Val | Pro | Leu | Asp | Gln | Ser |
| | | 290 | | | | | 295 | | | | | 300 | | | |
| Ile | Lys | Phe | Phe | Asp | Arg | Arg | Asp | Glu | Leu | Asn | Ile | Ala | Phe | Thr |
| 305 | | | | | 310 | | | | | 315 | | | | | 320 |
| Phe | Asp | Leu | Ile | Arg | Leu | Asp | Arg | Asp | Ser | Asp | Gln | Arg | Trp | Arg | Arg |
| | | | | 325 | | | | | 330 | | | | | 335 | |
| Lys | Glu | Trp | Lys | Leu | Ser | Gln | Phe | Arg | Gln | Val | Ile | Asp | Asn | Val | Asp |
| | | | 340 | | | | | 345 | | | | | 350 | | |
| Arg | Thr | Ala | Gly | Glu | Tyr | Gly | Trp | Asn | Ala | Phe | Phe | Leu | Asp | Asn | His |
| | | | | 355 | | | | | 360 | | | | | 365 | |
| Asp | Asn | Pro | Arg | Ala | Val | Ser | His | Phe | Gly | Asp | Asp | Arg | Pro | Gln | Trp |
| | | 370 | | | | | 375 | | | | | 380 | | | |

```
                                    -continued
Arg Glu Pro Ser Ala Lys Ala Leu Ala Thr Leu Thr Leu Thr Gln Arg
385                 390                 395                 400

Ala Thr Pro Phe Ile Tyr Gln Gly Ser Glu Leu Gly Met Thr Asn Tyr
                405                 410                 415

Pro Phe Lys Ala Ile Asp Glu Phe Asp Asp Ile Glu Val Lys Gly Phe
            420                 425                 430

Trp His Asp Tyr Val Glu Thr Gly Lys Val Lys Ala Asp Glu Phe Leu
        435                 440                 445

Gln Asn Val Arg Leu Thr Ser Arg Asp Asn Ser Arg Thr Pro Phe Gln
    450                 455                 460

Trp Asp Thr Ser Lys Asn Ala Gly Phe Thr Ser Gly Lys Pro Trp Phe
465                 470                 475                 480

Lys Val Asn Pro Asn Tyr Gln Glu Ile Asn Ala Val Ser Gln Val Ala
            485                 490                 495

Gln Pro Asp Ser Val Phe Asn Tyr Tyr Arg Gln Leu Ile Lys Ile Arg
            500                 505                 510

His Asn Ile Pro Ala Leu Thr Tyr Gly Thr Tyr Thr Asp Leu Asp Pro
        515                 520                 525

Ala Asn Asp Ser Val Tyr Ala Tyr Thr Arg Ser Leu Gly Ala Glu Lys
    530                 535                 540

Tyr Leu Val Val Val Asn Phe Gln Glu Gln Val Met Arg Tyr Lys Leu
545                 550                 555                 560

Pro Asp Asn Leu Ser Ile Glu Lys Val Ile Ile Glu Ser Asn Ser Lys
            565                 570                 575

Asn Val Val Lys Lys Asn Asp Ser Leu Leu Glu Leu Lys Pro Trp Gln
            580                 585                 590

Ser Gly Val Tyr Lys Leu Asn Gln
            595                 600
```

METHODS FOR OBTAINING PATHOGEN RESISTANCE IN PLANTS

RELATED APPLICATIONS

This application is a national stage application (under 35 U.S.C. §371) of PCT/EP03/07027 filed Jul. 2, 2003, which claims the benefit of German application 10230220.0 filed Jul. 4, 2002.

INCORPORATION OF SEQUENCE LISTING

The contents of the following submission on compact discs are incorporated herein by reference in it's entirety: two copies of the Sequence Listing (COPY 1 and COPY 2) and a computer-readable form of the Sequence list-13173-00012-US, date recorded: Feb. 17, 2006, size: 151 KB.

FIELD OF THE INVENTION

The invention relates to methods for generating or increasing a pathogen resistance in plants by expression, preferably pathogen-inducible expression, of a sucrose isomerase.

DESCRIPTION OF THE BACKGROUND

Palatinose (isomaltulose) and trehalulose are produced on a large scale from sucrose by an enzymatic rearrangement reaction using immobilized bacterial cells. The α1->β2-glycosidic bond, which exists between the monosaccharides of the disaccharide sucrose, is isomerized, in the case of palatinose to an α1->α6 bond or, in the case of trehalulose an α1->α1 bond. This rearrangement of sucrose to give the two noncariogenic disaccharides is catalyzed by the bacterial enzyme sucrose isomerase, also referred to as sucrose mutase. Suitable sequences are described for example in WO 95/20047 (U.S. Pat. No. 5,786,140; U.S. Pat. No. 5,985,622).

Also described are sucrose isomerases from *Erwinia rhapontici* (palI gene, GenBank Acc. No.: AF279281; Börnke et al. (2001) J Bacteriol 183(8):2425-2430) and *Klebsiella* sp. Strain LX3 (GenBank Acc. No.: AY040843; Zhang et al. (2002) Appl Environ Microbiol (68):2676-2682).

WO 01/59136 describes methods for the direct production of noncariogenic sugars directly in transgenic plants which comprise recombinant nucleic acid molecules encoding proteins with the enzymatic activity of a sucrose isomerase. Described are expression constructs for said sucrose isomerase for expression in plants, and the transgenic plants transformed therewith.

WO 01/59135 describes methods for influencing the pollen development using anther-, tapetum- or pollen-specifically expressed sucrose isomerases. However, the constitutive expression of sucrose isomerase in plants has an adverse effect on plant growth (Börnke F et al. (2002) Planta 214:356-364).

The aim of plant biotechnology work is the generation of plants with advantageous novel properties, for example for increasing agricultural productivity, increasing the quality in the case of foodstuffs, or for producing specific chemicals or pharmaceuticals. The plants' natural defense mechanisms against pathogens are frequently insufficient. Fungal-diseases alone result in annual yield losses of many billions of US$. The introduction of foreign genes from plants, animals or microbial sources can increase the defenses. Examples are the protection of tobacco against feeding damage by insects by expressing *Bacillus thuringiensis* endotoxins under the control of the 35S CaMV promoter (Vaeck et al. (1987) Nature 328:33-37) or the protection of tobacco against fungal infection by expressing a bean chitinase under the control of the CaMV promoter (Broglie et al. (1991) Science 254:1194-1197). However, most of the approaches described only offer resistance to a single pathogen or a narrow spectrum of pathogens.

Only a few approaches exist which impart a resistance to a broader spectrum of pathogens, in particular fungal pathogens, to plants. Systemic acquired resistance (SAR)—a defense mechanism in a variety of plant/pathogen interactions—can be conferred by the application of endogenous messenger substances such as jasmonic acid (JA) or salicylic acid (SA) (Ward, et al. (1991) Plant Cell 3:1085-1094; Uknes, et al. (1992) Plant Cell 4(6):645-656). Similar effects can also be achieved by synthetic compounds such as 2,6-dichloroisonicotinic acid (INA) or S-methyl benzo(1,2,3)thiadiazole-7-thiocarboxylate (BTH; BION) (Friedrich et al. (1996) Plant J 10(1):61-70; Lawton et al. (1996) Plant J. 10:71-82). The expression of pathogenesis-related (PR) proteins, which are upregulated in the case of SAR, may also cause pathogen resistance in some cases.

In barley, the Mlo locus has been described for some time as a negative regulator of plant defense. The loss, or loss of function, of the Mlo gene causes an increased and, above all, race-unspecific resistance for example against a large number of mildew species (Büschges R et al. (1997) Cell 88:695-705; Jorgensen J H (1977) Euphytica 26:55-62; Lyngkjaer M F et al. (1995) Plant Pathol 44:786-790). The Mlo gene has only recently been cloned (Buschges R et al. (1997) Cell 88:695-705; WO 98/04586; Schulze-Lefert P, Vogel J (2000) Trends Plant Sci. 5:343-348). Various methods for obtaining pathogen resistance using these genes have been described (WO 98/04586; WO 00/01722; WO 99/47552). It is unclear whether an Mlo-based approach can also be performed successfully in dicotyledonous plants.

Phytopathogenic fungal species generally live as saprophytes or parasites. The latter depend—at least during certain phases of their lifecycle—on a supply of active substances (for example a supply of vitamins, carbohydrates and the like), as it can only be provided in this form by live plant cells. The expert classifies parasitic fungi as necrotrophic, hemibiotrophic and biotrophic. In the case of necrotrophic fungal parasites, the infection results in destruction of the tissue and thus in the death of the plant. In most cases, these fungi are only facultative parasites; they are just as capable of saprophytic multiplication in dead or dying plant material.

Biotrophic fungal parasites are characterized in that parasite and host cohabit, at least over prolonged periods. While the fungus withdraws nutrients from the host, it does not kill it. Most biotrophic fungi are obligate parasites. Hemibiotrophic fungi live temporarily as biotrophs and kill the host at a later point in time, i.e. they enter a necrotrophic phase.

A further, large group of biotrophic plant pathogens of enormous agro-economical importance are nematodes. Phytopathogenic nematodes feed on the outermost parts of plant tissue (ectoparasites) or, after penetration into the plant, in cell layers further in (endoparasites). Two groups of endoparasitic root nematodes are distinguished according to their lifestyle and nutrition: cyst nematodes (*Heterodera* and *Globodera* species) and root-knot nematodes (*Meloidogyne* species). Both groups are obligate biotrophic parasites which induce the development of specific feeder cells in the roots. These feeder cells are plant cells whose metabolism has been modified by the nematodes in such a way that they specifically serve the supply of nutrients to the developing nematodes. The development of endoparasitic root nematodes depends totally on these feeder cells (for a review, see Sijmons et al. (1994) Ann. Rev. Phytopathol. 32: 235-259). Cyst nematodes (Heterodera and *Globodera* species) remain at the parasitization site in the root (sessile endoparasites) and convert the surrounding cells by protoplast fusion into syncytia while dissolving some of the cell walls. The nematodes feed off these feeder cells, which are formed in the root's central cylinder, during which process the nematodes swell greatly in size. Root-knot nematodes (Meloidogyne species) likewise remain at the parasitization site, once chosen, and bring about the development of feeder cells which, in contrast to the cyst nematodes, consist of several, multinucleate giant cells which develop as a result of synchronous divisions of the nucleus without cell wall formation (Fenoll and Del Campo (1998) Physiol. Mol. Biol. Plants 4:9-18). The development of the feeder cell systems is induced by signal molecules in the nematodes' saliva. It is known that a series of plant genes change their expression profile greatly during these differentiation, processes. Promoters which are induced specifically in the feeder cell system (syncytia) are described in the literature. Those which may be mentioned by way of example are the tobacco Δ0.3 TobRB7 promoter (Opperman et al. (1994) Science 263:221-223), the tomato Lemmi9 promoter (Ecobar et al. (1999) Mol Plant Microbe Interact 12: 440-449) and the geminivirus V sense promoters (WO 00/01832).

WO 94/10320 describes DNA constructs for the expression of genes which act as inhibitors of endogenous plant genes (for example ATP synthase, cytochrome C, pyruvate kinase) under the control of nematode-induced promoters in den syncytia.

Despite several advances in some fields of plant biotechnology, success in achieving a pathogen resistance in plants has been very limited and as yet only sufficiently documented in the case of viruses. Yield losses in particular as a result of fungal and nematode attack are a serious problem; then as now, they require an intensive application of fungicides and nematicides. However, the problems which this entails have still not been tackled sufficiently.

SUMMARY OF THE INVENTION

The present invention provides, generally, processes for generating or increasing resistance of plants to at least one pathogen with a protein containing a sucrose isomerase activity.

One embodiment of the invention is directed to methods for generating or increasing resistance of a plant to at least one pathogen comprising: transforming a collection of plant cells with a transgenic protein that possesses a sucrose isomerase activity; and selecting a plant cell from the transformed collection that generates or shows increased resistance, as compared to the untransformed plant cell, to the at least one pathogen. Preferably the sucrose isomerase activity is derived from: i) a protein containing the sequence of SEQ ID NO: 2, 6, 8, 10, 12, 14, 16, 18 or 36; ii) a functional equivalent to said protein; or iii) a fragment of said protein or said functional equivalent. Preferably the expression of the sucrose isomerase activity is ensured by a transgenic expression cassette comprising at least one nucleic acid sequence selected from the group consisting of: a) nucleic acid sequences encoding the amino acid sequence of SEQ ID NO: 2,4, 6, 8, 10, 12, 14, 16, 18, 20,22 or 36; b) nucleic acid sequences encoding proteins with at least 40% homology with the sequence of SEQ ID NO: 2, 4, 6, 8, 10, 12, 14, 16, 1 8, 20, 22 or 36; c) nucleic acid sequences that contain the sequence of SEQ ID No: 1, 3, 5, 7, 9, 11, 13, 15, 17, 19,21 or 35; d) nucleic acid sequences which is degenerated to a nucleic acid sequence of c); e) nucleic acid sequences with at least 40% homology with the nucleic acid sequence of SEQ ID No: 1, 3, 5, 7, 9, 11, 13, 15, 17, 19, 21 or 35; and f) nucleic acid sequences that hybridize with a complementary strand of the nucleic acid sequence of SEQ ID No: 1, 3, 5, 7,9, 11, 13, 15, 17, 19,21 or 35.

Preferably the sucrose isomerase activity is expressed under the control of a pathogen-inducible promoter which is functional in plants. Preferably the pathogen is selected from the group consisting of fungi and nematodes, and also preferably, the fungi is selected from the group consisting of Plasmodiophoramycota, Oomycota, Ascomycota, Chytridiomycetes, Zygomycetes, Basidiomycota and Deuteromycetes. Plants such as potato, beet, sugar beet, tomato, banana, carrot, sugar cane, strawberry, pineapple, paw paw, soybean, oats, barley, wheat, rye, tricicale, sorghum and millet, and maize, are often the preferred plants.

Another embodiment of the invention is directed to transgenic expression cassettes comprising nucleic acid sequences that encode a sucrose isomerase, which is in functional linkage with a pathogen-inducible promoter that is functional in plants. Preferably the sucrose isomerase is a protein containing the sequence of SEQ ID NO: 2, 6, 8, 10, 12, 14, 16, 18 or 36; a functional equivalent of said protein; or a fragment of said protein or said functional equivalent. Also preferably, the pathogen-inducible promoter contains a sequence selected from the group consisting of the sequences of SEQ ID NO: 23, 24, 32, 33 and 34.

Another embodiment of the invention is directed to transgenic expression vectors comprising the transgenic expression cassette of the invention.

Another embodiment of the invention is directed to transgenic organisms comprising the transgenic expression cassettes of the invention. Preferably, the transgenic organism is a plant selected from the group consisting of potato, beet, sugar beet, tomato, banana, carrot, sugar cane, strawberry, pineapple, paw paw, soybean, oats, barley, wheat, rye, tricicale, sorghum and millet, and maize.

Another embodiment of the invention is directed to a transgenic crop product, propagation material, cells, organs, parts, calli, cell cultures, seeds, tubers, sets or transgenic progeny of the transgenic organism of the invention.

Another embodiment of the invention is directed to methods for the production of palatinose comprising the transgenic organism or the transgenic expression vectors of the invention. Preferably, methods for the production of palatinose comprises transgenic crop products, propagation material, cells, organs, parts, calli, cell cultures, seeds, tubers, sets or transgenic progeny of the invention.

Another embodiment of the invention is directed to methods for increasing resistance of a plant to at least one pathogen comprising expressing a transgenic protein in said plant, wherein the transgenic protein possesses a sucrose isomerase activity that provides increased resistance, as compared to an unexpressing plant, to the at least one pathogen. Preferably, the transgenic protein is a protein containing the sequence of SEQ ID NO: 2, 6, 8, 10, 12, 14, 16, 18 or 36; is a functional equivalent of said protein; or is a fragment of said protein or said functional equivalent.

Other embodiments and advantages of the invention are set forth in part in the description, which follows, and in part, may be obvious from this description, or may be learned from the practice of the invention.

DESCRIPTION OF THE INVENTION

Figure 1:
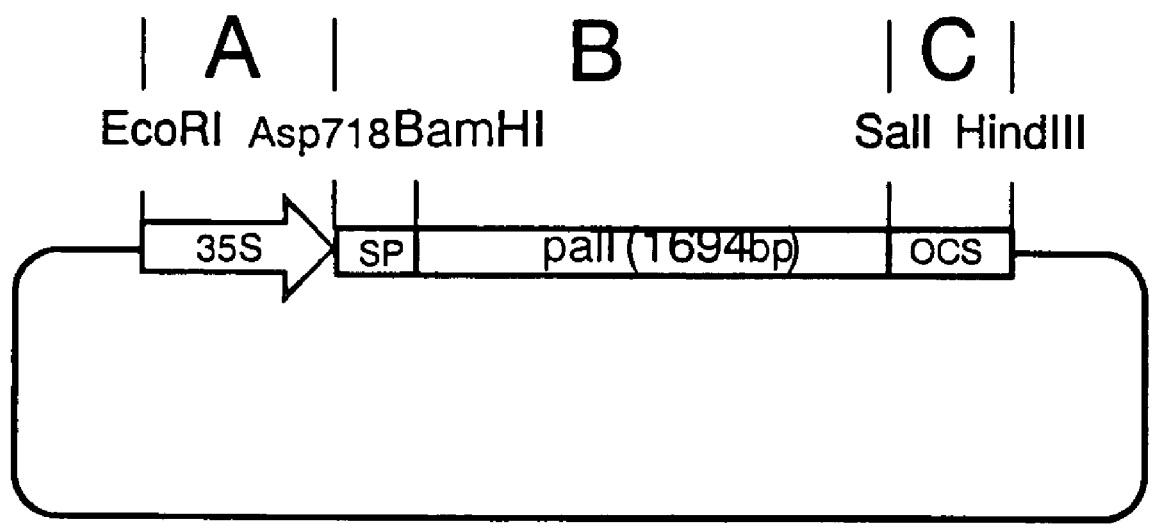
FIG. 1. Schematic representation of the expression cassette in the plasmid p35S -cwlso.

The present invention is based on the object of providing novel methods for pathogen defense, in plants, which bring about an effective defense of as broad a pathogen spectrum as possible, preferably a spectrum of fungi and nematodes, in as many different plant species as possible, preferably in agricultural crop plants. This object is achieved by the method according to the invention.

A first subject matter of the invention comprises a method for generating or increasing the resistance to at least one pathogen in plant organisms, which comprises the following process steps a) transgenic expression of a protein with sucrose isomerase activity in a plant organism or a tissue, organ, part or cell thereof, and
b) selection of those plant organisms in which, as opposed or as compared to the original plant, the resistance to at least one pathogen exists or is increased.

In principle, the method according to the invention can be applied to all plant organisms which produce sucrose. This includes all higher plants. Surprisingly, it was observed that the growth of the fungus *Alternaria* is significantly inhibited on potato disks of transgenic potato plants in whose tubers sucrose is converted into palatinose owing to the recombinant expression of a sucrose isomerase.

It can also be observed that the recombinant expression of the sucrose isomerase also brings about a resistance to nematodes. In particular syncytia-specific expression of the sucrose isomerase sequence, caused by endoparasitic root nematodes, brings about a marked reduction of the nematode infestation.

Since a large number of pathogens, in particular fungi and nematodes, are not capable of metabolizing palatinose, overcoming the resistance by simple mutation in the pathogens is hardly possible since acquiring a novel enzyme activity would be required.

Within the context of the present invention, "protein with sucrose isomerase activity" refers to a protein whose "essential property" is the catalysis of the isomerization of sucrose to other disaccharides, the α1->β2-glycosidic bond between glucose and fructose in the sucrose being converted into a different glycosidic bond between two monosaccharide units, in particular into an α1->α6 bond and/or an α1->α1 bond.

A sucrose isomerase activity can be measured indirectly via analyzing the resulting carbohydrates (for example palatinose content) in the manner with which the skilled worker is familiar, for example by analyzing ethanolic extracts of suitable biological material (for example material from a transgenic plant or a microorganism). Said extracts can be analyzed for example by HPLC and the sugars can be identified with reference to corresponding standards. An analytical method is described for example in WO 01/59136. Thus, to detect sucrose isomerase activity in plant extracts, leaf disks with a diameter of approximately 0.8 cm are extracted for 2 hours at 70° C. with 100 μl of 80% ethanol and 10 mM HEPES buffer (pH 7.5). An aliquot of these extracts can be analyzed using an HPLC system, for example from Dionex, which can be equipped with a PA-1 (4×250 mm) column and a pulsed electrochemical detector. Prior to injection, the samples can be spun down for 2 minutes at 13 000 rpm. The sugars can subsequently be eluted after 4 minutes at 150 mM NaOH and a flow rate of 1 ml/min, using a 10-minute gradient from 0 to 1 M sodium acetate. The sugars can be identified and determined quantitatively with the corresponding standards from Sigma.

A protein with sucrose isomerase activity is especially preferably understood as a protein which is capable of isomerizing sucrose into palatinose and/or trehalulose, as essential property. The palatinose and trehalulose amounts to at least 2%, preferably at least 20%, especially preferably at least 50% and most preferably at least 60% of the total disaccharides which are formed by the isomerization of sucrose.

The nucleic acid sequence encoding a protein with sucrose isomerase activity can be isolated from natural sources or synthesized by traditional methods.

Examples of organisms whose cells comprise proteins with sucrose isomerase activity and the nucleic acid sequences encoding therefor are, in particular, microorganisms of the genera *Protaminobacter, Erwinia, Serratia, Leuconostoc, Pseudomonas, Agrobacterium, Klebsiella* and *Enterobacter*. The following examples of such microorganisms may be mentioned in particular in this context: *Protaminobacter rubrum* (CBS 547, 77), *Erwinia rhapontici* (NCPPB 1578), *Serratia plymuthica* (ATCC 15928), *Serratia marcescens* (NCIB 8285), *Leuconostoc mesenteroides* NRRL B-52 If (ATCC 1083 0a). *Pseudomonas mesoacidophila* MX-45 (FERM 11808 or FERM BP 3619), *Agrobacterium radiobacter* MX-232 (FERM 12397 or FERM BP 3620), *Klebsiella* subspecies and *Enterobacter* species.

In a preferred embodiment, the nucleic acid sequence encoding a protein with a sucrose isomerase activity comprises nucleic acid sequences which encode proteins with sucrose isomerase activity, the nucleic acids being selected from the group consisting of i) nucleic acid sequences encoding a protein as shown in SEQ ID NO: 2, 6, 8, 10, 12, 14, 16, 18 or 36 and
ii) nucleic acid sequences encoding a functional equivalent to a protein as shown in SEQ ID NO: 2, 6, 8, 10, 12, 14, 16, 18 or 36 and
iii) nucleic acid sequences encoding functionally equivalent fragments to a protein as shown in i) and ii).

Further nucleic acid sequences which encode proteins with sucrose isomerase activity are known in the art and are thus available to the skilled worker for the transfer to plant cells. Thus, for example, sequences, from *Protaminobacter rubrum, Erwinia rhapontici, Enterobacter* species SZ 62 and *Pseudomonas mesoacidophila* MX-45 are described in WO 95/20047. The disclosure of this patent application is expressly referred to herewith, both with regard to the disclosed sequences themselves and with regard to the identification and characterization of these and further sucrose-isomerase-encoding sequences from other sources.

Further DNA sequences which encode sucrose isomerases can be found by the skilled worker in, inter alia, the gene databases using suitable search profiles and computer programs for screening for homologous sequences or for sequence alignments. In addition, the skilled worker can himself find, and employ for the purposes of the present invention, further sucrose-isomerase-encoding nucleic acid sequences from other organisms by means of conventional molecular-biological techniques. Thus, the skilled worker can for example derive suitable hybridization probes from the known sucrose isomerase sequences and employ them for screening cDNA libraries and/or genomic libraries of the desired organism in question from which a novel sucrose isomerase gene is to be isolated. In this context, the skilled worker can resort to customary hybridization, cloning and sequencing techniques (see, for example, Sambrook et al. (1989) Molecular Cloning: A Laboratory Manual, $2^{nd}$ edition, Cold Spring Harbor Laboratory Press, Cold Spring Harbor, N.Y.). Likewise, the skilled worker is capable of using PCR to synthesize, with the aid of known sucrose isomerase DNA sequences, suitable—optionally degenerate—oligonucleotides as primers for cloning novel genes; such primers can be employed successfully.

Proteins with sucrose isomerase activity and the nucleic acid sequences encoding them can be isolated without difficulty by the skilled worker in the familiar manner from those organisms in which such activities were detected. Suitable methods are described (for example DE 44 14 185). Thus, a genetic library whose clones comprise genomic segments, of between 2 and 15 kb, of the donor organism can be obtained for example by partial digestion of genomic DNA of such an organism (preferably a microorganism) and introducing the resulting fragments into suitable E. coli vectors, followed by transformation. Among E. coli cells which harbor these plasmids, those whose colonies develop a red coloration are selected by plating on McConkey palatinose medium. The plasmid DNA present in these cells is transferred into an E. coli mutant which is not capable of growth on galactose as the single C source (for example ED 8654, Sambrook et al., supra, pages A9-A13). This transformed cell line is capable of identifying palatinose producers in the genetic library which has been generated as described above with DNA of the donor organism. To identify the desired palatinose-forming clones, individual cells from the genetic library are grown on minimal salt media supplemented with galactose and sucrose. Following replica-plating of the clonies onto plates with the same medium, the cells are killed by applying toluene vapor. Cells of the screening strain are subsequently applied above the colonies of the genetic library in the form of a lawn in soft minimal salt agar without added C source, and incubated. Significant cell growth of the screening strain only develops at the location of cells of the genetic library which have produced palatinose. Testing the cells of the replica control reveals the isomerase content. The E. coli clones identified thus are not capable of growing on palatinose as the single C source in the medium, show no ability to cleave sucrose when the intact cells or cell extracts are tested, but will form palatinose when grown under these conditions and without addition of sucrose to the medium.

Alternatively, isomerase clones can also be identified using a PCR fragment. If plasmid DNA of the thus-identified E. coli clones is used as probes for hybridization on filters with immobilized DNA from the donor organism, gene regions which bear isomerase genes can be detected and made available in a targeted manner.

Functional equivalents of the proteins with sucrose isomerase activity disclosed within the present invention comprise preferably those from other organisms, for example from microorganisms, whose genomic sequence is known in its entirety or in part, such as, for example, from microorganisms of the genera *Protaminobacter, Erwinia, Serratia, Leuconostoc, Pseudomonas, Agrobacterium, Klebsiella* and *Enterobacter*. These can be identified for example by database search in sequence databases such as GenBank or by screening genetic libraries or cDNA libraries—for example using the sequence as shown in SEQ ID NO: 1 or a part thereof as search sequence or probe. Mutations comprise substitutions, additions, deletions, inversion or insertions of one or more amino acid residues.

If desired, the skilled worker can thus additionally resort to routine techniques in order to introduce various types of mutations into the sucrose-isomerase-encoding DNA sequence, which results in the synthesis of proteins whose biological properties may be modified. Thus, for example, it is possible specifically to prepare enzymes which are localized in specific compartments of the plant cell owing to addition of suitable signal sequences. Such sequences are described in the literature and known to the skilled worker (see, for example, Braun et al. (1992) EMBO J 11:3219-3227; Wolter F et al. (1988) Proc Natl Acad Sci USA 85:846-850; Sonnewald U et al. (1991) Plant J 1:95-106).

Also feasible is the introduction of point mutations at positions where for example a modification of the amino acid sequence affects, for example, enzyme activity or the regulation of the enzyme. In this manner it is possible, for example, to generate mutants which are no longer subject to the regulatory mechanisms via allosteric regulation or covalent modification, mechanisms which normally prevail in the cell. Moreover, mutants with a modified substrate or product specificity can be generated. Moreover, mutants with a modified activity, temperature and/or pH profile can be generated.

The degeneracy of the genetic code allows the skilled worker, inter alia, to adapt the nucleotide sequence of the DNA sequence to the codon preference of the target plant, that is to say the plant or plant cell which is pathogen-resistant owing to the expression of the sucrose isomerase-nucleic acid sequence, thus optimizing expression.

In order to perform recombinant manipulation in prokaryotic cells, the recombinant nucleic acid molecules according to the invention, or parts thereof, can be introduced into plasmids which permit mutagenesis or sequence modification by recombination of DNA sequences. Base substitutions can be carried out, or natural or synthetic sequences added, with the aid of standard methods (see, for example, Sambrook et al. (1989), vide supra). To link the DNA fragments to one another, adaptors or linkers may be added to the fragments where required. Moreover, suitable restriction cleavage sites can be provided, or excess DNA or restriction cleavage sites eliminated, by means of enzymatic and other manipulations. Where insertions, deletions or substitutions are suitable, invitro mutagenesis, primer repair, restriction or ligation may be used. Analytical methods which are generally carried out are sequence analysis, restriction analysis and further biochemical/molecular-biological methods.

Said functional equivalents preferably have at least 40%, particularly preferably at least 50%, particularly preferably at least 70%, most preferably at least 90%, homology with one of the polypeptide sequences with the SEQ ID NO: 2, 4, 6, 8, 10, 12, 14, 16, 18, 20, 22 or 36. The homology extends over at least 30 amino acids, preferably at least 60 amino acids, especially preferably at least 90 amino acids, most preferably over the entire length of one of the polypeptides as shown in SEQ ID NO: 2, 4, 6, 8, 10, 12, 14, 16, 18, 20, 22 or 36.

Homology between two polypeptides is understood as meaning the identity of the amino acid sequence over in each case the entire sequence length which is calculated by comparison with the aid of the program algorithm GAP (Wisconsin Package Version 10.0, University of Wisconsin, Genetics Computer Group (GCG), Madison, USA), setting the following parameters:

| | |
|---|---|
| Gap weight: 8 | Length weight: 2 |
| Average match: 2,912 | Average mismatch: −2,003 |

For example a sequence which has at least 80% homology with sequence SEQ ID NO: 2 at the protein-level is understood as meaning a sequence which, upon comparison with the sequence SEQ ID NO: 2 by the above program algorithm with the above parameter set, has at least 80% homology.

The term functional equivalents comprises also those proteins which are encoded by nucleic acid sequences which have at least 40%, especially preferably at least 50%, especially preferably at least 70%, most preferably at least 90% homology with one of the nucleic acid sequences with the SEQ ID NO: 1, 3, 5, 7, 9, 11, 13, 15, 17, 19, 21 or 35. The homology extends over at least 100 bases, preferably at least 200 bases, especially preferably at least 300 bases, most preferably over the entire length of one of the sequences as shown in SEQ ID NO: 1, 3, 5, 7, 9, 11, 13, 15, 17, 19, 21 or 35.

Homology between two nucleic acid sequences is understood as meaning the identity of the two nucleic acid sequences over in each case the entire sequence length which is calculated by comparison with the aid of the program algorithm GAP (Wisconsin Package Version 10.0, University of Wisconsin, Genetics Computer Group (GCG), Madison, USA; Altschul et al. (1997) Nucleic Acids Res. 25:3389 et seq.), setting the following parameters:

| | |
|---|---|
| Gap weight: 50 | Length weight: 3 |
| Average match: 10 | Average mismatch: 0 |

For example a sequence which has at least 80% homology with sequence SEQ ID NO: 1 at the nucleic acid level is understood as meaning a sequence which, upon comparison with the sequence SEQ ID NO: 1 by the above program algorithm with the above parameter set, has at least 80% homology.

The term functional equivalents also comprises those proteins which are encoded by nucleic acid sequences which hybridize under standard conditions with one of the nucleic acid sequences described by SEQ ID NO: 1, 3, 5, 7, 9, 11, 13, 15, 17, 19, 21 or 35, the nucleic acid sequence complementary thereto or parts of the above, and which have the essential properties of a sucrose isomerase.

"Standard hybridization conditions" is to be understood in the broad sense and means stringent or else less stringent hybridization conditions. Such hybridization conditions are described, inter alia, by Sambrook J, Fritsch E F, Maniatis T et al., in Molecular Cloning (A Laboratory Manual), 2nd Edition, Cold Spring Harbor Laboratory Press, 1989, pages 9.31-9.57 or in Current Protocols in Molecular Biology, John Wiley & Sons, N.Y. (1989), 6.3.1-6.3.6.

For example, the conditions during the wash step can be selected from the range of conditions delimited by low-stringency conditions (approximately 2×SSC at 50° C.) and high-stringency conditions (approximately 0.2×SSC at 50° C., preferably at 65° C.) (20×SSC: 0.3M sodium citrate, 3M NaCl, pH 7.0). In addition, the temperature during the wash step can be raised from low-stringency conditions at room temperature, approximately 22° C., to higher-stringency conditions at approximately 65° C. Both of the parameters salt concentration and temperature can be varied simultaneously, or else one of the two parameters can be kept constant while only the other is varied. Denaturants, for example formamide or SDS, may also be employed during the hybridization. In the presence of 50% formamide, hybridization is preferably effected at 42° C. Some examples of conditions for hybridization and wash step are shown hereinbelow:

(1) Hybridization conditions can be selected, for example, from the following conditions:
 a) 4×SSC at 65° C.,
 b) 6×SSC at 45° C.,
 c) 6×SSC, 100 μg/ml denatured fragmented fish sperm DNA at 68° C.,
 f) 50% formamide, 4×SSC at 42° C.,
 g) 2× or 4×SSC at 50° C. (low-stringency condition),
 h) 30 to 40% formamide, 2× or 4×SSC at 42° C. (low-stringency condition).

(2) Wash steps can be selected, for example, from the following conditions:
 a) 0.015 M NaCl/0.0015 M sodium citrate/0.1% SDS at 50° C.
 b) 0.1×SSC at 65° C.
 c) 0.1×SSC, 0.5% SDS at 68° C.
 d) 0.1×SSC, 0.5% SDS, 50% formamide at 42° C.
 e) 0.2×SSC, 0.1% SDS at 42° C.
 f) 2×SSC at 65° C. (low-stringency condition).

In a preferred embodiment, the nucleic acid sequence encoding a protein with a sucrose isomerase activity comprises nucleic acid sequences which encode proteins with sucrose isomerase activity, the nucleic acids being selected from the group consisting of a) nucleic acid sequences encoding an amino acid sequence as shown in SEQ ID NO: 2, 4, 6, 8, 10, 12, 14, 16, 18, 20, 22 or 36, and b) nucleic acid sequences encoding proteins with at least 40% homology with the sequence as shown in SEQ ID NO: 2, 4, 6, 8, 10, 12, 14, 16, 18, 20, 22 or 36, and c) nucleic acid sequences as shown in SEQ ID No: 1, 3, 5, 7, 9, 11, 13, 15, 17, 19, 21 or 35, and d) nucleic acid sequences which are degenerated to a nucleic acid sequence of c), and e) nucleic acid sequences with at least 40% homology with a nucleic acid sequence as shown in SEQ ID No: 1, 3, 5, 7, 9, 11, 13, 15, 17, 19, 21 or 35, and f) nucleic acid sequences which hybridize with a complementary strand of the nucleic acid sequence as shown in SEQ ID No: 1, 3, 5, 7, 9, 11, 13, 15, 17, 19, 21 or 35, and functionally equivalent fragments of the above.

With regard to a protein with sucrose isomerase activity or a nucleic acid sequence encoding such a protein, functionally equivalent fragments refers to all those polypeptides, or nucleic acid sequences encoding those polypeptides which, in comparison with their starting sequence, are truncated at the 5' and/or 3' end and/or have one or more deletions, but which still retain a sucrose isomerase activity, or still encode a protein with such an activity. One possibility in this context is the generation of deletion mutants where a progressive deletion from the 5' or the 3' end of the coding DNA sequence results in the synthesis of suitably truncated proteins.

As mentioned above, the coding sequences for sucrose isomerases can also be complemented by signal sequences which ensure that the gene product, i.e. predominantly the protein with sucrose isomerase activity, is transported into a particular compartment.

In a preferred embodiment of the invention, signal sequences ensure that the sucrose isomerase is transported into the cell wall or the apoplast of the transformed plant cells, i.e. the transformed plants express a chimeric sucrose isomerase, which comprises a signal peptide for the transport into the endoplasmic reticulum. Suitable signal sequences which ensure the uptake into the endoplasmic reticulum can be found by the skilled worker in the specialist literature. Especially suitable is for example the sequence which encodes the signal peptide of the potato proteinase inhibitor II gene (Keil et al. (1996) Nucl Acids Res 14:5641-5650; Genbank Accession No. X04118). Other suitable signal sequences ensure for example the uptake of sucrose isomerase into the vacuole. An example which may be mentioned is the signal peptide of the potato patatin gene (Sonnewald U et al. (1991) Plant J 1(1):95-106).

"Pathogen resistance" denotes the reduction or weakening of disease symptoms of a plant following infection by a pathogen. The symptoms can be manifold, but preferably comprise those which directly or indirectly have an adverse effect on the quality of the plant, the quantity of the yield, the suitability for use as feeding stuff or foodstuff, or else which make sowing, planting, harvesting or processing of the crop difficult.

"Conferring", "existing", "generating" or "increasing" a pathogen resistance means that the defense mechanisms of a specific plant species or variety is increasingly resistant to one or more pathogens due to the use of the method according to the invention in comparison with the wild type of the plant ("original plant"), to which the method according to the invention has not been applied, under otherwise identical conditions (such as, for example, climatic conditions, growing conditions, pathogen species and the like). The increased resistance manifests itself preferably in a reduced manifestation of the disease symptoms, disease symptoms comprising—in addition to the abovementioned adverse effects—for example also the penetration efficiency of a pathogen into the plant or plant cells or the proliferation efficiency in or on the same. In this context, the disease symptoms are preferably reduced by at least 10% or at least 20%, especially preferably by at least 40%, or 60%, very especially preferably by at least 70% or 80% and most preferably by at least 90% or 95%.

"Selection" with regard to plants in which—as opposed or as compared to the original plant—resistance to at least one pathogen exists or is increased means all those methods which are suitable for recognizing an existing or increased resistance to pathogens. These may be symptoms of pathogen infection (for example the development of haustoria in the case of fungal infection), but may also comprise the above-described symptoms which relate to the quality of the plant, the quantity of the yield, the suitability for use as feeding stuff or foodstuff and the like.

"Pathogen", within the scope of the invention means by way of example but not by limitation fungi, fungus-like pathogens (such as, for example, Chromista; e.g. *Oomycetes*) and animal pests such as, for example, nematodes. Especially preferred are nematodes and fungi. However, it can be assumed that the expression of a sucrose isomerase protein also brings about resistance to other pathogens.

The following pathogens may be mentioned by way of example but not by limitation:

1. Fungal Pathogens and Fungus-Like Pathogens:

Fungal pathogens and fungus-like pathogens (such as, for example, Chromista) comprise biotrophic, hemibiotrophic and necrotrophic fungi and are preferably from the group comprising Plasmodiophoramycota, oomycota, Ascomycota, Chytridiomycetes, Zygomycetes, Basidiomycota and Deuteromycetes (Fungi imperfecti). The pathogens mentioned in Tables 1 and 2 and the diseases with which they are associated may be mentioned by way of example but not by limitation.

TABLE 1

Fungal plant diseases

| Disease | Pathogen |
|---|---|
| Leaf rust | *Puccinia recondita* |
| Yellow rust | *P. striiformis* |
| Powdery mildew | *Erysiphe graminis* |
| Glume blotch | *Septoria nodorum* |
| Leaf blotch | *Septoria tritici* |
| Ear fusarioses | *Fusarium* spp. |
| Eyespot | *Pseudocercosporella herpotrichoides* |
| Smut | *Ustilago* spp. |
| Bunt | *Tilletia caries* |
| Take-all | *Gaeumannomyces graminis* |
| Anthrocnose leaf blight | *Colletotrichum graminicola* (teleomorph: |
| Anthracnose stalk rot | *Glomerella graminicola* Politis); *Glomerella tucumanensis* (anamorph: *Glomerella falcatum* Went) |
| *Aspergillus* ear and kernel rot | *Aspergillus flavus* |
| Banded leaf and sheath spot | *Rhizoctonia solani* Kuhn = *Rhizoctonia microsclerotia* J. Matz (telomorph: *Thanatephorus cucumeris*) |
| Black bundle disease | *Acremonium strictum* W. Gams = *Cephalosporium acremonium* Auct. non Corda |
| Black kernel rot | *Lasiodiplodia theobromae* = *Botryodiplodia theobromae* |
| Borde blanco | *Marasmiellus* sp. |
| Brown spot (black spot, stalk rot) | *Physoderma maydis* |
| *Cephalosporium* kernel rot | *Acremonium strictum* = *Cephalosporium acremonium* |
| Charcoal rot | *Macrophomina phaseolina* |
| Corticium ear rot | *Thanatephorus cucumeris* = *Corticium sasakii* |
| *Curvularia* leaf spot | *Curvularia clavata, C. eragrostidis,* = *C. maculans* (teleomorph: *Cochliobolus eragrostidis*), *Curvularia inaequalis, C. intermedia* (teleomorph: *Cochliobolus intermedius*), *Curvularia lunata* (teleomorph: *Cochliobolus lunatus*), *Curvularia pallescens* (teleomorph: *Cochliobolus pallescens*), *Curvularia senegalensis, C. tuberculata* (teleomorph: *Cochliobolus tuberculatus*) |
| *Didymella* leaf spot | *Didymella exitalis* |
| *Diplodia* ear rot and stalk rot | *Diplodia frumenti* (teleomorph: *Botryosphaeria festucae*) |
| *Diplodia* ear rot, stalk rot, seed rot and seedling blight | *Diplodia maydis* = *Stenocarpella maydis* |
| *Diplodia* leaf spot or streak | *Stenocarpella macrospora* = *Diplodia* leaf macrospora |

TABLE 2

Downy mildew (Oomycetes)

| Disease | Pathogen |
|---|---|
| Brown stripe downy mildew | *Sclerophthora rayssiae* var. *zeae* |

TABLE 2-continued

Downy mildew (Oomycetes)

| Disease | Pathogen |
| --- | --- |
| Crazy top downy mildew | *Sclerophthora macrospora* = *Sclerospora macrospora* |
| Green ear downy mildew (*graminicola* downy mildew) | *Sclerospora graminicola* |
| Java downy mildew | *Peronosclerospora maydis* = *Sclerospora maydis* |
| Philippine downy mildew | *Peronosclerospora philippinensis* = *Sclerospora philippinensis* |
| *Sorghum* downy mildew | *Peronosclerospora sorghi* = *Sclerospora sorghi* |
| *Spontaneum* downy mildew | *Peronosclerospora spontanea* = *Sclerospora spontanea* |
| *Sugarcane* downy mildew | *Peronosclerospora sacchari* = *Sclerospora sacchari* |
| Dry ear rot (cob, kernel and stalk rot) | *Nigrospora oryzae* (teleomorph: *Khuskia oryzae*) |
| Ear rots, minor | *Alternaria alternata* = *A. tenuis*, *Aspergillus glaucus*, *A. niger*, *Aspergillus* spp., *Botrytis cinerea* (teleomorph: *Botryotinia fuckeliana*), *Cunninghamella* sp., *Curvularia pallescens*, *Doratomyces stemonitis* = *Cephalotrichum stemonitis*, *Fusarium culmorum*, *Gonatobotrys simplex*, *Pithomyces maydicus*, *Rhizopus microsporus Tiegh.*, *R. stolonifer* = *R. nigricans*, *Scopulariopsis brumptii* |
| Ergot (horse's tooth) | *Claviceps gigantea* (anamorph: *Sphacelia* sp.) |
| Eyespot | *Aureobasidium zeae* = *Kabatiella zeae* |
| *Fusarium* ear and stalk rot | *Fusarium subglutinans* = *F. moniliforme* var. *subglutinans* |
| *Fusarium* kernel, root and stalk rot, seed rot and seedling blight | *Fusarium moniliforme* (teleomorph: *Gibberella fujikuroi*) |
| *Fusarium* stalk rot, seedling root rot | *Fusarium avenaceum* (teleomorph: *Gibberella avenacea*) |
| *Gibberella* ear and stalk rot | *Gibberella zeae* (anamorph: *Fusarium graminearum*) |
| Gray ear rot | *Botryosphaeria zeae* = *Physalospora zeae* (anamorph: *Macrophoma zeae*) |
| Gray leaf spot (*Cercospora* leaf spot) | *Cercospora sorghi* = *C. sorghi* var. *maydis*, *C. zeae-maydis* |
| *Helminthosporium* root rot | *Exserohilum pedicellatum* = *Helminthosporium pedicellatum* (teleomorph: *Setosphaeria pedicellata*) |
| *Hormodendrum* ear rot (*Cladosporium* rot) | *Cladosporium cladosporioides* = *Hormodendrum cladosporioides*, *C. herbarum* (teleomorph: *Mycosphaerella tassiana*) |
| *Hyalothyridium* leaf spot | *Hyalothyridium maydis* |
| Late wilt | *Cephalosporium maydis* |
| Leaf spots, minor | *Alternaria alternata*, *Ascochyta maydis*, *A. tritici*, *A. zeicola*, *Bipolaris victoriae* = *Helminthosporium victoriae* (teleomorph: *Cochliobolus victoriae*), *C. sativus* (anamorph: *Bipolaris sorokiniana* = *H. sorokinianum* = *H. sativum*), *Epicoccum nigrum*, *Exserohilum prolatum* = *Drechslera prolata* (teleomorph: *Setosphaeria prolata*) *Graphium penicillioides*, *Leptosphaeria maydis*, *Leptothyrium zeae*, *Ophiosphaerella herpotricha*, (anamorph: *Scolecosporiella* sp.), *Paraphaeosphaeria michotii*, *Phoma* sp., *Septoria zeae*, *S. zeicola*, *S. zeina* |
| Northern corn leaf blight (white blast, crown stalk rot, stripe) | *Setosphaeria turcica* (anarnorph: *Exserohilum turcicum* = *Helminthosporium turcicum*) |
| Northern corn leaf spot *Helminthosporium* ear rot (race 1) | *Cochliobolus carbonum* (anamorph: *Bipolaris zeicola* = *Helminthosporium carbonum*) |

TABLE 2-continued

Downy mildew (Oomycetes)

| Disease | Pathogen |
|---|---|
| *Penicillium* ear rot (blue eye, blue mold) | *Penicillium* spp., *P. chrysogenum*, *P. expansum*, *P. oxalicum* |
| *Phaeocytostroma* stalk rot and root rot | *Phaeocytostroma ambiguum*, = *Phaeocytosporella zeae* |
| *Phaeosphaeria* leaf spot | *Phaeosphaeria maydis* = *Sphaerulina maydis* |
| *Physalospora* ear rot (*Botryosphaeria* ear rot) | *Botryosphaeria festucae* = *Physalospora zeicola* (anamorph: *Diplodia frumenti*) |
| Purple leaf sheath | Hemiparasitic bacteria and fungi |
| *Pyrenochaeta* stalk rot and root rot | *Phoma terrestris* = *Pyrenochaeta terrestris* |
| *Pythium* root rot | *Pythium* spp., *P. arrhenomanes*, *P. graminicola* |
| *Pythium* stalk rot | *Pythium aphanidermatum* = *P. butleri* L. |
| Red kernel disease (ear mold, leaf and seed rot) | *Epicoccum nigrum* |
| *Rhizoctonia* ear rot (*sclerotial* rot) | *Rhizoctonia zeae* (teleomorph: *Waitea circinata*) |
| *Rhizoctonia* root rot and stalk rot, | *Rhizoctonia solani, Rhizoctonia zeae* |
| Root rots, minor | *Alternaria alternata, Cercospora sorghi, Dictochaeta fertilis, Fusarium acuminatum* (teleomorph: *Gibberella acuminata*), *F. equiseti* (teleomorph: *G. intricans*), *F. oxysporum, F. pallidoroseum, F. poae, F. roseum, G. cyanogena*, (anamorph: *F. sulphureum*), *Microdochium bolleyi, Mucor* sp., *Periconia circinata, Phytophthora cactorum*, P. drechsleri, P. nicotianae var. parasitica, *Rhizopus arrhizus* |
| *Rostratum* leaf spot (*Helminthosporium* leaf disease, ear and stalk rot) | *Setosphaeria rostrata*, (anamorph: *Exserohilum rostratum* = *Helminthosporium rostratum*) |
| Rust, common corn | *Puccinia sorghi* |
| Rust, southern corn | *Puccinia polysora* |
| Rust, tropical corn | *Physopella pallescens, P. zeae* = *Angiopsora zeae* |
| *Sclerotium* ear rot (southern blight) | *Sclerotium rolfsii* Sacc. (teleomorph: *Athelia rolfsii*) |
| Seed rot-seedling blight | *Bipolaris sorokiniana, B. zeicola* = *Helminthosporium carbonum, Diplodia maydis, Exserohilum pedicillatum, Exserohilum turcicum* = *Helminthosporium turcicum, Fusarium avenaceum, F. culmorum, F. moniliforme, Gibberella zeae* (anamorph: *F. graminearum*), *Macrophomina phaseolina, Penicillium* spp., *Phomopsis* sp., *Pythium* spp., *Rhizoctonia solani, R. zeae, Sclerotium rolfsii, Spicaria* sp. |
| *Selenophoma* leaf spot | *Selenophoma* sp. |
| Sheath rot | *Gaeumannomyces graminis* |
| Shuck rot | *Myrothecium gramineum* |
| Silage mold | *Monascus purpureus, M ruber* |
| Smut, common | *Ustilago zeae* = *U. maydis* |
| Smut, false | *Ustilaginoidea virens* |
| Smut, head | *Sphacelotheca reiliana* = *Sporisorium holcisorghi* |
| Southern corn leaf blight and stalk rot | *Cochliobolus heterostrophus* (anamorph: *Bipolaris maydis* = *Helminthosporium maydis*) |
| Southern leaf spot | *Stenocarpella macrospora* = *Diplodia macrospora* |
| Stalk rots, minor | *Cercospora sorghi, Fusarium episphaeria, F. merismoides, F. oxysporum* Schlechtend, *F. poae, F. roseum, F. solani* (teleomorph: *Nectria haematococca*), *F. tricinctum, Mariannaea elegans, Mucor* sp., *Rhopographus zeae, Spicaria* sp. |
| Storage rots | *Aspergillus* spp., *Penicillium* spp. and other fungi |
| Tar spot | *Phyllachora maydis* |

TABLE 2-continued

Downy mildew (Oomycetes)

| Disease | Pathogen |
| --- | --- |
| Trichoderma ear rot and root rot | *Trichoderma viride* = *T. lignorum* teleomorph: *Hypocrea* sp. |
| White ear rot, root and stalk rot | *Stenocarpella maydis* = *Diplodia zeae* |
| Yellow leaf blight | *Ascochyta ischaemi*, *Phyllosticta maydis* (teleomorph: *Mycosphaerella zeae maydis*) |
| Zonate leaf spot | *Gloeocercospora sorghi* |

The following are especially preferred

Plasmodiophoromycota such as *Plasmodiophora brassicae* (clubroot of crucifers), *Spongospora subterranea* (powdery scab of potato tubers), *Polymyxa graminis* (root disease of cereals and grasses), Oomycota such as *Bremia lactucae* (downy mildew of lettuce), *Peronospora* (downy mildew) in snapdragon (*P. antirrhini*), onion (*P. destructor*), spinach (*P. effusa*), soybean (*P. manchurica*), tobacco ("blue mold"; *P. tabacina*), alfalfa and clover (*P. trifolium*), *Pseudoperonospora humuli* (downy mildew of hops), *Plasmopara* (downy mildew in grapevines) (*P. viticola*) and sunflower (*P. halstedii*), *Sclerophthora macrospora* (downy mildew in cereals and grasses), *Pythium* (seed rot, seedling damping-off, and root rot and all types of plants, for example damping-off of Beta beet caused by *P. debaryanum*), *Phytophthora infestans* (blight in potato, brown rot in tomato and the like), *Albugo* spec. (white rust on cruciferous plants)

Ascomycota such as *Microdochium nivale* (snow mold of rye and wheat), *Fusarium graminearum, Fusarium culmorum* (partial ear sterility mainly in wheat), *Fusarium oxysporum* (Fusarium wilt of tomato), *Blumeria graminis* (powdery mildew of barley (f.sp. *hordei*) and wheat (f.sp. *tritici*)), *Erysiphe pisi* (powdery mildew of pea), *Nectria galligena* (Nectria canker of fruit trees), *Uncinula necator* (powdery mildew of grapevine), *Pseudopeziza tracheiphila* (red fire disease of grapevine), *Claviceps purpurea* (ergot on, for example, rye and grasses), *Gaeumannomyces graminis* (take-all on wheat, rye and other grasses), *Magnaporthe grisea* (rice blast disease), *Pyrenophora graminea* (leaf stripe of barley), *Pyrenophora teres* (net blotch of barley), *Pyrenophora tritici-repentis* (leaf blight of wheat), *Venturia inaequalis* (apple scab), *Sclerotinia sclerotium* (stalk break, stem rot), *Pseudopeziza medicaginis* (leaf spot of alfalfa, white and red clover).

Basidiomycetes such as *Typhula incarnata* (typhula blight on barley, rye, wheat), *Ustilago maydis* (blister smut on maize), *Ustilago nuda* (loose smut on barley), *Ustilago tritici* (loose smut on wheat, spelt), *Ustilago avenae* (loose smut on oats), *Rhizoctonia solani* (rhizoctonia root rot of potato), *Sphacelotheca* spp. (head smut of sorghum), *Melampsora lini* (rust of flax), *Puccinia graminis* (stem rust of wheat, barley, rye, oats), *Puccinia recondita* (leaf rust on wheat), *Puccinia dispersa* (brown rust on rye), *Puccinia hordei* (leaf rust of barley), *Puccinia coronata* (crown rust of oats), *Puccinia striiformis* (yellow rust of wheat, barley, rye and a large number of grasses), *Uromyces appendiculatus* (brown rust of bean), *Sclerotium rolfsii* (root and stem rots of many plants).

Deuteromycetes (Fungi imperfecti) such as *Septoria nodorum* (glume blotch) of wheat (*Septoria tritici*), *Pseudocercosporella herpotrichoides* (eyespot of wheat, barley, rye), *Rynchosporium secalis* (leaf spot on rye and barley), *Alternaria solani* (early blight of potato, tomato), *Phoma betae* (blackleg on Beta beet), *Cercospora beticola* (leaf spot on Beta beet), *Alternaria brassicae* (black spot on oilseed rape, cabbage and other crucifers), *Verticillium dahliae* (verticillium wilt), *Colletotrichum lindemuthianum* (bean anthracnose), *Phoma lingam* (blackleg of cabbage and oilseed rape), *Botrytis cinerea* (grey mold of grapevine, strawberry, tomato, hops and the like).

Most preferred are *Phytophthora infestans* (potato blight, brown rot in tomato and the like), *Microdochium nivale* (previously *Fusarium nivale*; snow mold of rye and wheat), *Fusarium graminearum, Fusarium culmorum* (partial ear sterility of wheat), *Fusarium oxysporum* (Fusarium wilt of tomato), *Blumeria graminis* (powdery mildew of barley (f. sp. *hordei*) and wheat (f. sp. *tritici*)), *Magnaporthe grisea* (rice blast disease), *Sclerotinia sclerotium* (stalk break, stem rot), *Septoria nodorum* and *Septoria tritici* (glume blotch of wheat), *Alternaria brassicae* (black spot of oilseed rape, cabbage and other crucifers), *Phoma lingam* (blackleg of cabbage and oilseed rape).

2. Animal Pests

Among the plant-injurious nematodes which are preferred for the control within the scope of the present invention, the following groups may be mentioned by way of example, but not by limitation:

a) active, migratory root nematodes (for example *Pratylenchus, Xiphinema* and *Longidorus* species).

Migratory nematodes are not bound to one parasitization site, but can change the latter. They can migrate from one root to another, from one plant to another and in some cases also within the plant tissue. Their importance as pests has long been underrated. Nowadays, they are among the extremely dangerous plant-injurious nematodes. Many types of growth damage (including what is known as "cell sickness") and premature yellowing of the crop plants have been attributed to such root pests. *Pratylenchus* species in particular are also known in the cultivation of ornamentals as the cause of substantial root damage. Diseased roots can be recognized from sections of brown discoloration. Rot organisms subsequently enter the lesions caused, bring about rapid death of the tissue and pronounced rotting at these locations. Host plants are inter alia: various cereal species, potatoes, carrots, tomatoes, cucumbers, celery/celeriac and grapevine.

b) Root-gall-causing nematodes (for example *Meloidogyne* species)

The larvae of these species usually burrow into the roots close to the tip and, by virtue of exudations of their saliva glands, cause nuts (galls) in the surrounding plant tissue to form. They are sedentary in these galls, and return to the soil either actively or after decomposition of the galls. The adverse effect on the plant's metabolism, which is the result of the attack by these pests, can be seen from the more or less stunted growth and general failure of the plant to thrive. Root-knot eelworms are major pests in particular in greenhouses, but have also been identified in the open on carrots, celery/celeriac and parsley.

c) Nematodes which attack the floral primordia: (*Anguina tritici*)

The ear-cockle eelworm is a parasite which specializes in the floral primordia of wheat, which it converts into galls. Attack by this nematode can already be identified during the juvenile stage of the plant from the waviness or curliness of the leaves.

d) Cyst-forming root nematodes: (*Globodera* and *Heterodera* species)

The potato cyst nematode is Potato Enemy Number 1. Regarding its injuriousness, this species surpasses all the other *Heterodera* species; severe infestation can destroy up to 80% of the harvest. After infestation with cyst nematodes, the plant fails to thrive and no cause can be discerned externally. Only an examination of the roots reveals pinhead-sized brownish, yellow or whitish cysts are revealed. The female nematodes burrow into the root, which they burst by means of their abdomens, which is filled with eggs and thereby swelling. While the packed abdomen is still surrounded by the soil, the nematode's mouth spear is still attached to the root. The female dies, and its solidifying skin becomes a protective cover (cyst) for the eggs and larvae. The cysts together with their contents are very resilient and can persist for a long time. Under suitable environmental conditions, the larvae burrow into the open and infest fresh roots. The most important cyst nematodes are the potato cyst nematode, the beet cyst nematode, the cereal cyst nematode, the pea cyst nematode, the clover cyst nematode, the beet cyst eelworm, the hop cyst nematode, and the carrot cyst nematode.

Preferred animal pests are in particular nematodes. Examples which may be mentioned, but not by limitation, are the pathogens mentioned in Table 3 and the diseases associated with them.

TABLE 3

Parasitic nematodes

| Damage | Pathogenic nematode |
| --- | --- |
| Awl | *Dolichodorus* spp., *D. heterocephalus* |
| Bulb and stem nematode disease; Europe | *Ditylenchus dipsaci* |
| Burrowing | *Radopholus similis* |
| Cyst nematode disease | *Heterodera avenae, H. zeae, Punctodera chalcoensis* |
| Dagger | *Xiphinema* spp., *X. americanum, X. mediterraneum* |
| False root-knot | *Nacobbus dorsalis* |
| Lance, Columbia | *Hoplolaimus columbus* |
| Lance | *Hoplolaimus* spp., *H. galeatus* |
| Lesion | *Pratylenchus* spp., *P. brachyurus, P. crenatus, P. hexincisus, P. neglectus, P. penetrans, P. scribneri, P. thornei, P. zeae* |
| Needle | *Longidorus* spp., *L. breviannulatus* |
| Ring | *Criconemella* spp., *C. ornata* |
| Root-knot disease | *Meloidogyne* spp., *M. chitwoodi, M. incognita, M. javanica* |
| Spiral | *Helicotylenchus* spp. |
| Sting | *Belonolaimus* spp., *B. longicaudatus* |
| Stubby-root | *Paratrichodorus* spp., *P. christiei, P. minor, Quinisulcius acutus, Trichodorus* spp. |
| Stunt | *Tylenchorhynchus dubius* |

Very especially preferred are *Globodera rostochiensis* and *G. pallida* (cyst eelworm on potato, tomato and other Solanaceae), *Heterodera schachtii* (beet eelworm on sugar and fodder beet, oilseed rape, cabbage and the like), *Heterodera avenae* (cereal cyst nematode on oat and other cereal species), *Ditylenchus dipsaci* (stem or bulb eelworm, stem eelworm of rye, oats, maize, clover, tobacco, beet), *Anguina tritici* (ear-cockle nematode, cockle disease of wheat (spelt, rye), *Meloidogyne hapla* (root-knot nematode of carrot, cucumber, lettuce, tomato, potato, sugar beet, lucerne).

It is preferred to obtain a resistance to the following examples of fungal pathogens in the individual plant species:

1. Barley: *Puccinia graminis* f.sp. *hordei* (barley stem rust), *Blumeria* (*Erysiphe*) *graminis* f.sp. *hordei* (barley powdery mildew).

2. Soybean: *Phytophthora megasperma* fsp. *glycinea*, *Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotrichum truncatum*), *Corynespora cassiicola, Septoria glycines, Phyllosticta sojicola, Alternaria alternata, Microsphaera diffusa, Fusarium semitectum, Phialophora gregata, Glomerella glycines, Phakopsora pachyrhizi, Pythium aphamidermatum, Pythium ultimum, Pythium debaryanum, Fusarium solani.*

3. Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata.*

4. Alfalfa: *Clavibater michiganese* subsp. *insidiosum, Pythium ultimum, Pythium irregulare, Pythium splendens, Pythium debaryanum, Pythium aphamidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium, Aphanomyces euteiches, Stemphylium herbarum, Stemphylium alfalfae.*

5. Wheat: *Urocystis agropyri, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. tritici, *Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphamidermatum, Pythium arrhenomanes, Pythium ultimum, Bipolaris sorokiniana, Claviceps purpurea, Tilletia tritici, Tilletia laevis, Ustilago tritici, Tilletia indica, Rhizoctonia solani, Pythium arrhenomannes, Pythium gramicola, Pythium aphamidermatum, Puccinia graminis* f.sp. *tritici* (wheat stem rust), *Blumeria* (*Erysiphe*) *graminis* f.sp. *tritici* (wheat powdery mildew).

6. Sunflower: *Plasmophora halstedii, Sclerotinia sclerotiorum, Aster Yellows, Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Cephalosporium acremonium, Phytophthora cryptogea, Albugo tragopogonis.*

7. Maize: *Fusarium moniliforme* var. *subglutinans, Fusarium moniliforme, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphamidermatum, Aspergillus flavus, Bipolaris maydis* 0, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Trichoderma viride, Claviceps sorghi, Cornstunt spiroplasma, Diplodia macrospora, Sclerophthora macrospora, Peronosclerospora sorghi, Peronosclerospora philippinesis, Peronosclerospora maydis, Peronosclerospora sacchari, Spacelotheca reiliana, Physopella zeae, Cephalosporium maydis, Caphalbsporium acremonium.*

8. Sorghum: *Exserohilum turcicum, Colletotrichum graminicola* (*Glomerella graminicola*), *Cercospora sorghi, Gloeocercospora sorghi, Ascochyta sorghina, Puccinia purpurea, Macrophomina phaseolina, Perconia circinata, Fusarium moniliform, Alternaria alternata, Bipolaris sorghicola, Helminthosporium sorghicola, Curvularia lunata, Phoma insidiosa, Ramulispora sorghi, Ramulispora sorghicola, Phyllachara sacchari, Sporisorium reilianum* (*Sphacelotheca reiliana*), *Sphacelotheca cruenta, Sporisorium sorghi, Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola.*

It is preferred to obtain, in the individual plant species, a resistance to the following nematode pathogens which are mentioned by way of example:

| | | |
|---|---|---|
| Sugar beet | Sugar beet cyst nematode | *Heterodera schachtii* |
| Potato | Columbia root-knot nematode | *Meloidogyne chitwoodi* |
| | Golden Nematode | *Globodera rostochiensis* |
| | Northern root knot nematode | *Meloidogyne hapla* |
| | Potato rot nematode | *Ditylenchus destructor* |
| Soybean | Soybean cyst nematode; SCN | *Heterodera glycines* |
| Maize | Corn cyst nematode | *Heterodera zeae* |
| | Root-knot nematodes | *Meloidogyne species:* |
| | | *Meloidogyne arenaria* |
| | | *Meloidogyne graminicola* |
| | | *Meloidogyne chitwoodi* |
| | | *Meloidogyne hapla* |
| | | *Meloidogyne incognita* |
| | | *Meloidogyne javanica* |

"Plant organism or cells derived therefrom" generally refers to any cell, tissue, part or propagation material (such as seeds or fruits) of an organism which is capable of photosynthesis. Included for the purposes of the invention are all genera and species of higher and lower plants of the Plant Kingdom. Preferred plants are annual, perennial, monocotyledonous and dicotyledonous plants. Included are the mature plant, seed, shoots and seedlings, and parts, propagation material (for example tubers, seeds or fruits) and cultures, for example cell or callus cultures, which are derived therefrom. Mature plants refers to plants at any developmental stage beyond the seedling stage. Seedling refers to a young, immature plant in an early developmental stage.

The term "plant" in the context of the invention refers to all genera and species of higher and lower plants of the Plant Kingdom. The term includes the mature plants, seed, shoots and seedlings and parts, propagation material, plant organs, tissue, protoplasts, callus and other cultures, for example cell cultures, which are derived therefrom, and any other type of plant cell grouping to give functional or structural units. Mature plants refers to plants at any developmental stage beyond that of the seedling. Seedling refers to a young immature plant at an early developmental stage.

"Plant" comprises all annual and perennial monocotyledonous and dicotyledonous plants and includes by way of example but not by limitation those of the genera *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium, Helianthus, Lactuca, Bromus, Asparagus, Antirrhinum, Heterocallis, Nemesis, Pelargonium, Panicum, Pennisetum, Ranunculus, Senecio, Salpiglossis, Cucumis, Browallia, Glycine, Pisum, Phaseolus, Lolium, Oryza, Zea, Avena, Hordeum, Secale, Triticum, Sorghum, Picea* and *Populus.*

Preferred plants are those from the following plant families: Amaranthaceae, Asteraceae, Brassicaceae, Carophyllaceae, Chenopodiaceae, Compositae, Cruciferae, Cucurbitaceae, Labiatae, Leguminosae, Papilionoideae, Liliaceae, Linaceae, Malvaceae, Rosaceae, Rubiaceae, Saxifragaceae, Scrophulariaceae, Solanaceae, Sterculiaceae, Tetragoniacea, Theaceae, Umbelliferae.

Preferred monocotyledonous plants are selected in particular from the monocotyledonous crop plants such as, for example, the family; of the Gramineae such as rice, maize, wheat or other cereal species such as barley, sorghum and millet, rye, triticale or oats, and sugar cane, and all grass species.

The invention is very especially preferably applied to dicotyledonous plant organisms. Preferred dicotyledonous plants are in particular selected among the dicotyledonous crop plants such as, for example, Asteraceae, such as sunflower, Tagetes or *Calendula* and others, Compositae, in particular the genus *Lactuca*, especially the species *sativa* (lettuce) and others, Cruciferae, especially the genus *Brassica*, very especially the species *napus* (oilseed rape), *campestris* (beet), *oleracea* cv Tastie (cabbage), *oleracea* cv Snowball Y (cauliflower) and *oleracea* cv Emperor (broccoli) and other cabbage species; and the genus *Arabidopsis*, very especially the species *thaliana*, and cress or canola and others, Cucurbitaceae, such as melon, pumpkin/squash or courgette and others, Leguminosae, especially the genus *Glycine*, very especially the species *max* (soybean) and alfalfa, pea, beans or peanut, and others Rubiaceae, preferably the subclass Lamidae, such as, for example *Coffea arabica* or *Coffea liberica* (coffee bush) and others, Solanaceae, in particular the genus *Lycopersicon*, very especially the species *esculentum* (tomato), the genus *Solanum*, very especially the species *tuberosum* (potato) and *melongena* (aubergine), and the genus *Capsicum*, very especially the species *annuum* (bell pepper) and tobacco and others, Sterculiaceae, preferably the subclass Dilleniidae, such as, for example, *Theobroma cacao* (cacao tree) and others, Theaceae, preferably the subclass Dilleniidae, such as, for example, *Camellia sinensis* or *Thea sinensis* (tee shrub) and others, Umbelliferae, especially the genus *Daucus* (very especially the species *carota* (carrot)) and *Apium* (very especially the species *graveolens dulce* (celery)) and others, and linseed, soybean, cotton, hemp, flax, cucumber, spinach, carrot, sugar beet and the various tree, nut and grapevine species, in particular banana and kiwi.

Also comprised are ornamental plants, useful trees, ornamental trees, flowers, cut flowers, shrubs or lawn. Those which must be mentioned by way of example, but not by limitation, are angiosperms, bryophytes such as, for example, Hepaticae (liverworts) and Musci (mosses); pteridophytes such as ferns, mare's tail, Lycopodiaceae; gymnosperms such as conifers, cycads, ginkgo and Gnetatae, the families of the Rosaceae such as rose, Ericaceae such as rhododendrons and azaleas, Euphorbiaceae such as poinsettias and croton, Caryophyllaceae such as carnations, Solanaceae such as petunias, Gesneriaceae such as African violet, Balsaminaceae such as touch-me-not, Orchidaceae such as orchids, Iridaceae such as gladioli, iris, freesia and crocus, Compositae such as *calendula*, Geraniaceae such as geraniums, Liliaceae such as dracaena, Moraceae such as ficus, Araceae such as philodendron and many others.

Most preferred are agricultural crop plants which naturally have a high sucrose content or whose roots, tubers or storage roots are of economic utility, such as, for example, potato, beet or sugar beet. Likewise preferred are tomato, banana, carrot, sugar cane, strawberry, pineapple, paw paw, soybean and cereal species such as oats, barley, wheat, rye, triticale, sorghum and millet, and maize. Most preferred are potato, beet, sugar beet and sugar cane.

Within the present invention, expression constructs for expressing proteins with sucrose isomerase activity in plants are employed. Such expression cassettes are described for example in wo 01/59136 and WO 01/59135, which are expressly referred to herewith.

In said expression constructs, a nucleic acid molecule encoding a protein with sucrose isomerase activity (for example described by SEQ ID NO: 2 or a functional equivalent thereof or a functional equivalent part of the above) is preferably operably linked to at least one genetic control element (for example a promoter) which ensures recombinant expression in a plant organism or a tissue, organ, part or cell thereof.

Operable linkage is to be understood as meaning, for example, the sequential arrangement of a promoter with the nucleic acid sequence to be expressed (for example the sequence as shown in SEQ ID NO:. 1) and, if appropriate, further regulatory elements such as, for example, a terminator in such a way that each of the regulatory elements can fulfill its function when the nucleic acid sequence is expressed recombinantly. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other.

Operable linkage, and an expression construct, can be generated by means of customary recombination and cloning techniques as are described, for example, in Maniatis T, Fritsch E F and Sambrook J (1989) Molecular Cloning: A Laboratory Manual, Cold Spring Harbor Laboratory, Cold Spring Harbor (NY), in Silhavy T J, Berman M L and Enquist L W (1984) Experiments with Gene Fusions, Cold Spring Harbor Laboratory, Cold Spring Harbor (NY), in Ausubel F M et al. (1987) Current Protocols in Molecular Biology, Greene Publishing Assoc. and Wiley Interscience and in Gelvin et al. (1990) In: Plant Molecular Biology Manual. However, further sequences which, for example, act as a linker with specific cleavage sites for restriction enzymes, as att sequence for recombinases or as a signal peptide, may also be positioned between the two sequences. The insertion of sequences may also lead to the expression of fusion proteins. Preferably, the transgenic expression construct, consisting of a linkage of promoter and nucleic acid sequence to be expressed, can exist in a vector-integrated form and be inserted into a plant genome, for example by transformation.

However, an expression construct also denotes those constructions in which the nucleic acid sequence encoding the protein with sucrose isomerase activity (for example encoded by SEQ ID NO: 2 or a functional equivalent thereof or a functionally equivalent part of the above) is placed behind an endogenous plant promoter—for example by homologous recombination—in such a way that this promoter ensures the recombinant expression of said nucleic acid sequence.

The term plant-specific promoters is understood as meaning, in principle, any promoter which is capable of governing the expression of genes, in particular foreign genes, in plants or plant parts, plant cells, plant tissues, or plant cultures. Here, the promoter may be chosen in such a way that expression is constitutive or only in a specific tissue or organ, at a particular point in time of the plant development- and/or at a point in time which is determined by external factors, biotic or abiotic stimuli (induced gene expression). With regard to the plant to be transformed, the promoter may be homologous or heterologous. The following are preferred:

a) Constitutive Promoters

"Constitutive" promoter is understood as meaning those promoters which ensure expression in a large number of, preferably all, tissues over a substantial period of plant development, preferably at all stages of plant development (Benfey et al.(1989) EMBO J 8:2195-2202). In particular a plant promoter or a promoter derived from a plant virus are preferably used. Particularly preferred is the promoter of the CaMV cauliflower mosaic virus 35S transcript (Franck et al. (1980) Cell 21:285-294; Odell et al. (1985) Nature 313:810-812; Shewmaker et al. (1985) Virology 140:281-288; Gardner et al. (1986) Plant Mol Biol 6:221-228) or the 19S CaMV promoter (U.S. Pat. No. 5,352,605; WO 84/02913; Benfey et al. (1989) EMBO J 8:2195-2202). Another suitable constitutive promoter is the legumin B promoter (GenBank Acc. No. X03677), the *Agrobacterium nopaline* synthase promoter, the TR dual promoter, the *Agrobacterium* OCS (octopine synthase) promoter, the ubiquitin promoter (Holtorf S et al. (1995) Plant Mol Biol 29:637-649), the ubiquitin 1 promoter (Christensen et al. (1992) Plant Mol Biol 18:675-689; Bruce et al. (1989) Proc Natl Acad Sci USA 86:9692-9696), the Smas promoter, the cinnamyl alcohol dehydrogenase promoter (U.S. Pat. No. 5,683,439), the promoters of the vacuolar ATPase subunits or the promoter of a proline-rich protein from wheat (WO 91/13991), and further promoters of genes whose constitutive expression in plants is known to the skilled worker. Especially preferred as constitutive promoter is the promoter of the nitrilase-1 (nit1) gene from *A. thaliana* (GenBank Acc. No.: Y07648.2, Nukleotide 2456-4340, Hillebrand et al. (1996) Gene 170:197-200).

b) Tissue-Specific Promoters

Preferred are furthermore promoters with specificity for the leaves, stems, roots and seeds.

Seed-specific promoters such as, for example, the phaseolin promoter (U.S. Pat. No. 5,504,200; Bustos M M et al. (1989) Plant Cell 1(9):839-53; e.g. the *Phaseolus vulgari*; van der Geest et al. (1996) Plant Mol Biol 32:579-588), the 2S albumin promoter (Joseffson L G et al. (1987) J Biol Chem 262:12196-12201), the legumin promoter (Shirsat A et al. (1989) Mol Gen Genet 215(2): 326-331), the USP (unknown seed protein) promoter (Bäumlein H et al. (1991) Mol Gen Genet 225(3):459-467; Phillips et al. (1997) EMBO J 16:4489-4496; the napin gene promoter (U.S. Pat. No. 5,608,152; Stalberg K et al. (1996) L Planta 199:515-519), the sucrose binding protein promoter (WO 00/26388), the hordein promoter (Brandt et al. (1985) Carlsberg Res. Commun. 50:333-345) or the legumin B4.promoter (LeB4; Bäumlein H et al. (1991) Mol Gen Genet 225: 121-128; Bäumlein H et al. (1992) Plant J 2(2):233-239; Fiedler U et al. (1995) Biotechnology (NY) 13(10):1090f), the *Arabidopsis oleosin* promoter (WO 98/45461), the *Brassica* Bce4 promoter (WO 91/13980).

Further suitable seed-specific promoters are those of the genes encoding the high-molecular-weight glutenin (HMWG), gliadin, branching enzyme, ADP glucose pyrophosphatase (AGPase), the napin promoter, the ACP promoter and the FatB3 and FatB4 promoters, the starch synthase promoter or the promoter of other starch-forming/modifying enzymes such as, for example, promoters of genes which encode branching enzymes (WO 92/14827, WO 92/11375). Furthermore preferred promoters are those which permit seed-specific expression in monocots such as maize, barley, wheat, rye, rice and the like. The following can be employed advantageously: the promoter of the lpt2 or lpt1 gene (WO 95/15389, WO 95/23230) or the promoters described in WO 99/16890 (promoters of the hordein gene, the glutelin gene, the oryzin gene, the prolamin gene, the gliadin gene, the glutelin gene, the zein gene, the kasirin gene, or the secalin gene). Further seed-specific promoters are described in WO 89/03887.

tuber-, storage-root- or root-specific promoters such as, for example, the patatin promoter class I (B33), the potato Cathepsin D inhibitor promoter.

Especially preferred in this context is the B33 promoter of the *Solanum tuberosum* class I patatin gene (Rocha-Sosa et al. (1989) EMBO J 8:23-29). The promoter of the class I patatin gene is approximately 100 to 1000 times more active in tubers than in leaves (Rocha-Sosa et al., vide supra). Other genes with tuber-specific expression, or at least enhanced expression in tubers, are known (for example the promoter of the ADP-glucose pyrophosphorylase genes;, Müller et al. (1990) Mol Gen Genet 224:136-146).

Leaf-specific promoters such as the potato cytosolic FBPase promoter (WO 97/05900), the Rubisco (ribulose-1,5-bisphosphate carboxylase) SSU (small subunit) promoter (U.S. Pat. No. 4,962,028) or the ST-LSI promoter from potato (Stockhaus et al. (1989) EMBO J 8:2445-2451). Very especially preferred are epidermis-specific promoters such as, for example, the OXLP gene (oxalate-oxidase-like protein) promoter (Wei et al. (1998) Plant Mol Biol 36:101-112).

c) Chemically Inducible Promoters

The transgenic expression constructs can also comprise a chemically inducible promoter (review article: Gatz et al. (1997) Annu Rev Plant Physiol Plant Mol Biol 48:89-108), by which the expression of the exogenous gene in the plant at a particular point in time can be controlled. Such promoters such as, for example, the PRP1 promoter (Ward et al. (1993) Plant Mol Biol 22:361-366), a salicylic-acid-inducible promoter (WO 95/19443), a benzenesulfonamide-inducible promoter (EP 0 388 186), a tetracyclin-inducible promoter (Gatz et al. (1992) Plant J 2:397-404)., an abscisic-acid-inducible promoter (EP 0 335 528) or an ethanol- or cyclohexanone-inducible promoter (WO 93/21334) can likewise be used.

d) Development-Dependent Promoters

Further suitable promoters are, for example, fruit-maturation-specific promoters such as, for example, the tomato fruit-maturation-specific promoter (WO 94/21794, EP 409 625). Development-dependent promoters comprise partly the tissue-specific promoters, since individual tissues develop by nature in a development-dependent fashion.

e) Stress- or Pathogen-Inducible Promoters

Further preferred promoters are those which are induced by biotic or abiotic stress such as, for example, the pathogen-inducible promoter of the PRP1 gene (Ward et al. (1993) Plant Mol Biol 22:361-366), the tomato high-temperature-inducible hsp70 or hsp80 promoter (U.S. Pat. No. 5,187,267), the potato low-temperature-inducible alpha-amylase promoter (wo 96/12814) or the light-inducible PPDK promoter.

Pathogen-inducible promoters comprise the promoters of genes which are induced as a consequence of infection by pathogens, such as, for example, genes of PR proteins, SAR proteins, β-1,3-glucanase, chitinase and the like (for example Redolfi et al. (1983) Neth J Plant Pathol 89:245-254;.Uknes et al. (1992) Plant Cell 4:645-656; Van Loon (1985) Plant Mol Viral 4:111-116; Marineau et al. (1987) Plant Mol Biol 9:335-342; Matton et al. (1987) Molecular Plant-Microbe Interactions 2:325-342; Somssich et al. (1986) Proc Natl Acad Sci USA 83:2427-2430; Somssich et al. (1988) Mol Gen Genetics 2:93-98; Chen et al. (1996) Plant J 10:955-966; Zhang and Sing (1994) Proc Natl Acad Sci USA 91:2507-2511; Warner, et al. (1993) Plant J 3:191-201; Siebertz et al. (1989) Plant Cell 1:961-968 (1989).

Also comprised are wounding-inducible promoters such as that of the pinII gene (Ryan (1990) Ann Rev Phytopath 28:425-449; Duan et al. (1996) Nat Biotech 14:494-498), of the wun1 and wun2 gene (U.S. Pat. No. 5,428,148), of the win1 and win2 gene (Stanford et al. (1989) Mol Gen Genet 215:200-208), of the systemin gene (McGurl et al. (1992) Science 225:1570-1573), of the WIP1 gene (Rohmeier et al. (1993) Plant Mol Biol 22:783-792; Eckelkamp et al. (1993) FEBS Letters 323:73-76), of the MPI gene (Corderok et al. (1994) Plant J 6(2):141-150) and the like.

Especially preferred are promoters which are induced specifically in feeder cell systems (syncytia) following infection by nematodes. The following may be mentioned by way of example:

i) the tobacco Δ0.3 TobRB7 promoter (Opperman et al. (1994) Science 263: 221-223), in particular the promoter described by SEQ ID NO: 24, ii) the tomato Lemmi9 promoter (Escobar et al. (1999) Mol Plant Microbe Interact 12: 440-449), in particular the promoter described by SEQ ID NO: 23, and iii) geminivirus V sense promoters (WO 00/01832), in particular the promoters described by SEQ ID NO: 32, 33 or 34.

Further nematode-inducible promoters which are preferred for the purposes of the present invention are described in WO 98/22599. Particularly preferred in this context are the regulatory regions. (i.e. the regions which precede the ATG start codon) of the sequences with the GenBank Acc. No.: A91914 (base pairs 1 to 3480). Furthermore preferred are the promoter sequences described in. U.S. Pat. No. 6,395,963, the promoter sequences described in WO 03/033651, the promoter sequences described in JP 2001508661-A (in particular the sequence with the GenBank Acc. No.: BD056958), and the promoter sequences described in WO 97/46692 (in particular the sequence with the GenBank Acc. No.: A79355;, base pairs 1 to 2127, or 1 to 2160). Further nemotode-inducible promoters can be derived from genes whose induction as the result of nematode infection has been described. Examples which may be mentioned, but not by limitation, are: the pollenin promoter (Karimi M et al. (2002) J Nematol 34(2):75-79) and the promoter of a putative receptor serine/threonine protein kinase (Custers J H H V et al. (2002) Mol Plant Pathol 3(4):239-249).

Especially preferred are pathogen- or stress-inducible promoters and seed-, tuber-, root-, leaf- and/or stem-specific promoters, with pathogen-inducible promoters (in particular the nematode-inducible promoters which have been mentioned individually above) being most preferred.

A further—especially preferred—subject of the invention relates to expression constructs in which a nucleic acid sequence encoding a protein with sucrose isomerase activity is in operable linkage with a stress-, pathogen-, or wounding-inducible promoter. Stress-, pathogen- or wounding-inducible promoters generally refers to all those promoters which are capable of being induced by biotic or abiotic stress. Abiotic stress means, in this context, stimuli such as high and low temperatures, dryness, frost, humidity, salt, UV light and the like. Biotic stress means, in this context, the infection with a pathogen, the term "pathogen" comprising all the abovementioned pathogens. This stimulus is preferably potent enough to lead to a yield reduction of at least 5% in comparison with average yields. Inducible means, in this context, an increase of the transcription activity by at least 50%, preferably at least 100%, especially preferably at least 500%, very especially preferably at least 1000%, most preferably at least 5000% in comparison with the expression activity of a nonstimulated plant. By way of example, but not by limitation, stress- or pathogen-inducible promoters comprise the pathogen-inducible promoter of the PRP1 gene (Ward et al. (1993) Plant Mol Biol 22:361-366), the tomato high-temperature-inducible hsp70 or hsp80 promoter (U.S. Pat. No. 5,187,267), the potato low-temperature-inducible α-amylase promoter (WO 96/12814), the light-inducible PPDK promoter or the wounding-inducible pinII promoter (EP-A 0 375 091). Preferred are, in particular, pathogen-inducible promoters such as, for example, the promoters of the PR proteins, SAR proteins, β-1,3-glucanase, chitinase and the like (for example Redolfi et al. (1983) Neth J Plant Pathol 89:245-254; Uknes, et al. (1992) The Plant Cell 4:645-656; Van Loon (1985) Plant Mol Viral 4:111-116; Marineau et al. (1987) Plant Mol Biol 9:335-342; Matton et al. (1987) Molecular Plant-Microbe Interactions 2:325-342; Somssich et al. (1986) Proc Natl Acad Sci USA 83:2427-2430; Somssich et al. (1988) Mol Gen Genetics 2:93-98; Chen et al. (1996) Plant J 10:955-966; Zhang and Sing (1994) Proc Natl Acad Sci USA 91:2507-2511; Warner, et al. (1993) Plant J 3:191-201; Siebertz et al. (1989) Plant Cell 1:961-968). Also comprised are wounding-inducible promoters such as that of the pinII gene (Ryan (1990) Ann Rev Phytopath 28:425-449; Duan et al. (1996) Nat Biotech 14:494-498), of the wun1 and wun2 gene (U.S. Pat. No. 5,428,148), of the win1 and win2 gene (Stanford et al. (1989) Mol Gen Genet 215:200-208), of the systemin gene (McGurl et al. (1992) Science 225:1570-1573), of the WIP1 gene (Rohmeier et al. (1993) Plant Mol Biol 22:783-792; Eckelkamp et al. (1993) FEBS Letters 323:73-76), of the MPI gene (Corderok et al. (1994) Plant J 6(2):141-150) and the like. Wounding-inducible promoters can be employed advantageously in the case of infection by feeding pathogens.

Moreover, the average skilled worker can additionally readily find more examples of genes with stress-, pathogen- or wounding-induced expression patterns in the literature. Furthermore, the average skilled worker is capable of isolating further suitable promoters by means of routine methods. Thus, the skilled worker can identify suitable regulatory nucleic acid elements with the aid of conventional molecular-biological methods, for example hybridization experiments or DNA-protein-binding studies. In this context, a first step may consist in establishing a differential expression library of, for example, pathogen-infected/infested and "normal" tissue. Thereafter, promoters which have pathogen-inducible regulatory elements are isolated with the aid of the pathogen-induced cDNAS thus identified. In addition, the skilled worker has available further, PCR-based methods for the isolation of suitable stress-, pathogen- or wounding-induced promoters.

Especially preferred are tissue-specific promoters, in particular seed-specific, tuber-specific, fruit-specific and leaf-specific promoters, and pathogen-induced promoters.

Very especially preferred are pathogen-induced promoters, in particular nematode-induced promoters.

Furthermore, further promoters may be linked operably to the nucleic acid sequence to be expressed, which promoters make possible the recombinant expression in further plant tissues or in other organisms, such as, for example, E. coli bacteria. Suitable plant promoters are, in principle, all of the above-described promoters.

The nucleic acid sequences present in the expression constructs or expression vectors can be linked operably to further genetic control sequences in addition to a promoter. The term "genetic control sequences" is to be understood in the broad sense and refers to all those sequences which have an effect on the materialization or the function of an expression construct. For example, genetic control sequences modify the transcription and translation in prokaryotic or eukaryotic organisms. Preferably, the expression constructs comprise a plant-specific promoter 5'-upstream of the nucleic acid sequence in question to be expressed recombinantly, and 3'-downstream a terminator sequence as additional genetic control sequence and, if appropriate, further customary regulatory elements, in each case linked operably to the nucleic acid sequence to be expressed recombinantly.

Genetic control sequences also comprise further promoters, promoter elements or minimal promoters, all of which can modify the expression-governing properties. Thus, for example, the tissue-specific expression may additionally depend on certain stress factors, owing to genetic control sequences. Such elements have been described, for example, for water stress, abscisic acid (Lam E and Chua N H (1991) J Biol Chem 266(26): 17131-17135) and heat stress (Schoffl F et al. (1989). Mol Gen Genetics 217(2-3):246-53).

Genetic control sequences furthermore also comprise the 5'-untranslated regions, introns or noncoding 3'-region of genes, such as, for example, the actin-1 intron, or the Adh1-S introns 1, 2 and 6 (general reference: The Maize Handbook, Chapter 116, Freeling and Walbot, Eds., Springer, New York (1994)). It has been demonstrated that they may play a significant role in the regulation of gene expression. Thus, it has been demonstrated that 5'-untranslated sequences can enhance the transient expression of heterologous genes. Examples of translation enhancers which may be mentioned are the tobacco mosaic virus 5' leader sequence (Gallie et al. (1987) Nucl Acids Res 15:8693-8711) and the like. Furthermore, they may promote tissue specificity (Rouster J et al. (1998) Plant J 15:435-440).

The transgenic expression construct may advantageously comprise one or more of what are known as enhancer sequences, linked operably to the promoter, which make possible an increased recombinant expression of the nucleic acid sequence. Additional advantageous sequences, such as further regulatory elements or terminators, may also be inserted at the 3' end of the nucleic acid sequences to be expressed recombinantly. One or more copies of the nucleic acid sequences to be expressed recombinantly may be present in the gene construct.

Polyadenylation signals which are suitable as control sequences are plant polyadenylation signals, preferably those which essentially correspond to T-DNA polyadenylation signals from *Agrobacterium tumefaciens*. Examples of terminator sequences which are especially suitable are the OCS (octopine synthase) terminator and the NOS (nopaline synthase) terminator.

Control sequences are furthermore to be understood as those which make possible homologous recombination or insertion into the genome of a host organism or which permit removal from the genome. Upon homologous recombination, for example the coding sequence of a particular endogenous gene may be specifically exchanged for the sequence which encodes a sucrose isomerase.

A transgenic expression construct and/or the transgenic expression vectors derived from it may comprise further functional elements. The term functional element is to be understood in the broad sense and refers to all those elements which have an effect on the generation, amplification or function of the transgenic expression constructs, the transgenic expression vectors or the transgenic organisms according to the invention. The following may be mentioned by way of example, but not by limitation:

a) Selection markers which confer a resistance to biocides, e.g. metabolism inhibitors (such as 2-deoxyglucose-6-phosphate (WO 98/45456)), antibiotics (such as, for example, kanamycin, G 418, bleomycin or hygromycin) or herbicides (such as glyphosate or phosphinothricin).

Especially preferred selection markers are those which confer resistance to herbicides. Examples which may be mentioned are: DNA sequences which encode phosphinothricin acetyl transferases (PAT) and which inactivate glutamin synthase inhibitors (bar and pat genes), 5-enolpyruvylshikimate-3-phosphate synthase genes (EPSP synthase genes), which confer resistance to glyphosate (N-(phosphonomethyl)glycine), the gox gene, which encodes glyphosate-degrading enzymes (glyphosate oxidoreductase), the deh gene (encoding a dehalogenase which inactivates dalapon), sulfonylurea- and imidazolinone -inactivating acetolactate synthases, and bxn genes, which encode bromoxynil-degrading nitrilase enzymes, the aasa gene, which confers resistance to the antibiotic-apectinomycin, the streptomycin phosphotransferase (spt) gene, which allows resistance to streptomycin, the neomycin phosphotransferase (nptII) gene, which confers resistance to kanamycin or geneticin (G418), the hygromycin phosphotransferase (hpt) gene, which mediates resistance to hygromycin, the acetolactate synthase gene (als), which confers resistance to sulfonylurea herbicides (for example mutated ALS variants with, for example, the S4 and/or Hra mutation).

b) Reporter genes which encode readily quantifiable proteins and, via their color or enzyme activity, make possible an assessment of the transformation efficacy, the site of expression or the time of expression. Very especially preferred in this context are reporter proteins (Schenborn E, Groskreutz D. Mol Biotechnol. 1999; 13(1):29-44) such as the green fluorescent protein (GFP) (Sheen et al.(1995) Plant Journal 8(5):777-784), chloramphenicol transferase, luciferase (Ow et al. (1986) Science 234:856-859), aequorin (Prasher et al. (1985) Biochem Biophys Res Commun 126(3):1259-1268), β-galactosidase, with β-glucuronidase being very especially preferred (Jefferson et al. (1987) EMBO J 6:3901-3907).

c) Origins of replication, which ensure amplification of the transgenic expression constructs or transgenic expression vectors according to the invention in, for example, *E. coli*. Examples of ORI (origin of DNA replication) which may be mentioned are the pBR322 ori or the P15A ori (Sambrook et al.: Molecular Cloning. A Laboratory Manual, 2nd ed. Cold Spring Harbor Laboratory Press, Cold Spring Harbor, N.Y., 1989).

d) Elements which are necessary for *Agrobacterium*-mediated plant transformation, such as, for example, the right or left border of the T-DNA or the vir region.

To select successfully transformed cells, it is, as a rule, necessary additionally to introduce a selectable marker which confers resistance to a biocide (for example a herbicide), to a metabolism inhibitor such as 2-deoxyglucose-6-phosphate (WO 98/45456) or to an antibiotic to the cells which have successfully undergone recombination. The selection marker permits the selection of the transformed cells from untransformed ones (McCormick et al. (1986) Plant Cell Reports 5:81-84).

The introduction of an expression construct according to the invention into an organism or cells, tissues, organs, parts or seeds thereof (preferably into plants or plant cells, tissue, organs, parts or seeds) can be effected advantageously using vectors which comprise the transgenic expression constructs. Examples of vectors may be plasmids, cosmids, phages, viruses or else agrobacteria. The transgenic expression construct can be introduced into the vector (preferably a plasmid vector) via a suitable restriction cleavage site or a recombinase att sequence. The transgenic expression vector formed is first introduced into *E. coli*. Correctly transformed *E. coli* are selected, grown, and the recombinant vector is obtained by the methods familiar to the skilled worker. Restriction analysis and sequencing may serve to verify the cloning step. Preferred vectors are those which make possible stable integration of the transgenic expression construct into the plant genome.

The generation of a transformed organism (or of a transformed cell or tissue) requires introducing the DNA (for example the expression vector) or RNA in question into the relevant host cell. A multiplicity of methods are available for this procedure, which is termed transformation (or transduction or transfection) (Keown et al. (1990) Methods in Enzymology 185:527-537). For example, the DNA or RNA can be introduced directly by microinjection or by bombardment with DNA-coated microparticles. Also, the cell can be permeabilized chemically, for example using polyethylene glycol, so that the DNA can enter the cell by diffusion. The DNA can also be introduced by protoplast fusion with other DNA-containing units such as minicells, cells, lysosomes or liposomes. Another suitable method of introducing DNA is electroporation, where the cells are permeabilized reversibly by an electrical pulse. Suitable methods have been described (for example by Bilang et al. (1991) Gene 100:247-250; Scheid et al. (1991) Mol Gen Genet 228:104-112; Guerche et al. (1987) Plant Science 52:111-116; Neuhause et al. (1987) Theor Appl Genet 75:30-36; Klein et al. (1987) Nature 327:70-73; Howell et al. (1980) Science 208:1265; Horsch et al.(1985) Science 227:1229-1231; DeBlock et al. (1989) Plant Physiology 91:694-701; Methods for Plant Molecular Biology (Weissbach and Weissbach, eds.) Academic Press Inc. (1988); and Methods in Plant Molecular Biology (Schuler and Zielinski, eds.) Academic Press Inc. (1989)).

In plants, the above-described methods of transforming and regenerating plants from plant tissues or plant cells are exploited for transient or stable transformation. Suitable methods are especially protoplast transformation by polyethylene-glycol-induced DNA uptake, the biolistic method with the gene gun, what is known as the particle bombardment method, electroporation, incubation of dry embryos in DNA-containing solution, and microinjection.

In addition to these "direct" transformation techniques, transformation can also be effected by bacterial infection by means of *Agrobacterium tumefaciens* or *Agrobacterium rhizogenes*. The *Agrobacterium*-mediated transformation is best suited to dicotyledonous plant cells. The methods are described, for example, by Horsch R B et al. (1985) Science 225: 1229f.

When agrobacteria are used, the transgenic expression construct must be integrated into specific plasmids, either into a shuttle or intermediate vector, or into a binary vector. If a Ti or Ri plasmid is to be used for the transformation, at least the right border, but in most cases the right and left border, of the Ti or Ri plasmid T-DNA is linked to the transgenic expression construct to be introduced in the form of a flanking region.

Binary vectors are preferably used. Binary vectors are capable of replication both in *E. coli* and in *Agrobacterium*. As a rule, they comprise a selection marker gene for the selection of transformed plants (for example the nptII gene, which confers resistance to kanamycin) and a linker or polylinker flanked by the right and left T-DNA border sequence. Apart from the T-DNA border sequence, they additionally comprise a selection marker which permits the selection of transformed *E. coli* and/or agrobacteria (e.g. the nptIII gene, which confers resistance to kanamycin). Such vectors can be transformed directly into *Agrobacterium* (Holsters et al. (1978) Mol Gen Genet 163:181-187).

The *Agrobacterium* which acts as host organism in this case should already contain a plasmid with the vir region. The latter is required for transferring the T-DNA to the plant cell. An *Agrobacterium* transformed in this way can be used for transforming plant cells. The use of T-DNA for transforming plant cells has been studied and described intensively (EP 120 516; Hoekema, In: The Binary Plant Vector System, Offsetdrukkerij Kanters B. V., Alblasserdam, Chapter V; An et al. (1985) EMBO J 4:277-287). Various binary vectors are known, some of which are commercially available such as, for example, pBI101.2 or pBIN19 (Clontech Laboratories, Inc. USA).

Direct transformation techniques are suitable for any organism and cell type. The plasmid used need not meet any particular requirements in the case of the injection or electroporation of DNA or RNA into plant cells. Simple plasmids such as those of the pUC series can be used. If complete plants are to be regenerated from the transformed cells, it is advantageous for an additional selectable marker gene to be located on the plasmid.

Stably transformed cells, i.e. those which contain the introduced DNA integrated into the DNA of the host cell, can be selected from untransformed cells when a selectable marker is part of the DNA introduced. Examples of genes which can act as markers are all those which are capable of conferring resistance to antibiotics or herbicides (such as kanamycin, G 418, bleomycin, hygromycin or phosphinothricin etc.) (see above). Transformed cells which express such marker genes are capable of surviving in the presence of concentrations of a corresponding antibiotic or herbicide which kill an untransformed wild type. Examples are mentioned above and preferably comprise the bar gene, which confers resistance to the herbicide phosphinothricin (Rathore K S et al. (1993) Plant Mol Biol 21(5):871-884), the nptII gene, which confers resistance to kanamycin, the hpt gene, which confers resistance to hygromycin, or the EPSP gene, which confers resistance to the herbicide glyphosate. The selection marker permits the selection of transformed cells from untransformed cells (McCormick et al. (1986) Plant Cell Reports 5:81-84). The resulting plants can be bred and hybridized in the customary fashion. Two or more generations should be grown in order to ensure that the genomic integration is stable and hereditary.

The abovementioned methods are described, for example, in Jenes B et al.(1993) Techniques for Gene Transfer, in: Transgenic Plants, Vol. 1, Engineering and Utilization; edited by S D Kung and R Wu, Academic Press, pp. 128-143 and in Potrykus (1991) Annu Rev Plant Physiol Plant Molec Biol 42:205-225. The expression construct is preferably cloned into a vector which is suitable for the transformation of *Agrobacterium tumefaciens*, for example pBin19 (Bevan et al. (1984) Nucl Acids Res 12:8711f).

As soon as a transformed plant cell has been generated, a complete plant can be obtained using methods known to the skilled worker. For example, callus cultures are used as starting material. The development of shoot and root can be induced from this as yet undifferentiated cell biomass in a known fashion. The shoots obtained can be planted out and bred.

The skilled worker is familiar with such methods of regenerating intact plants from plant cells and plant parts. Methods to do so are described, for example, by Fennell et al. (1992.) Plant Cell Rep. 11: 567-570; Stoeger et al (1995) Plant Cell Rep. 14:273-278; Jahne et al. (1994) Theor Appl Genet 89:525-533.

"Transgenic/recombinant" refers to all those constructs and methods in which either a) the nucleic acid sequence encoding a protein with sucrose isomerase activity, or b) a genetic control sequence linked operably to said nucleic acid sequence under a), for example a promoter, or c) (a) and (b)

are not located in their natural genetic environment or have been modified by recombinant methods, an example of a modification being a substitution, addition, deletion, inversion or insertion of one or more nucleotide residues. Natural genetic environment refers to the natural chromosomal locus in the organism of origin, or to the presence in a genomic library.

| Sequences |
|---|
| 1. SEQ ID NO: 1 nucleic acid sequence encoding *Protaminobacter rubrum* sucrose isomerase |
| 2. SEQ ID NO: 2 amino acid sequence encoding *Protaminobacter rubrum* sucrose isomerase |
| 3. SEQ ID NO: 3 nucleic acid sequence encoding sucrose isomerase of *Erwinia rhaponthici* sucrose isomerase (N-terminal fragment) |
| 4. SEQ ID NO: 4 amino acid sequence encoding sucrose isomerase of *Erwinia rhaponthici* sucrose isomerase (N-terminal fragment) |
| 5. SEQ ID NO: 5 nucleic acid sequence encoding *Erwinia rhaponthici* sucrose isomerase |
| 6. SEQ ID NO: 6 amino acid sequence encoding *Erwinia rhaponthici* sucrose isomerase |
| 7. SEQ ID NO: 7 nucleic acid sequence encoding *Protaminobacter rubrum* sucrose isomerase (variant) |
| 8. SEQ ID NO: 8 amino acid sequence encoding *Protaminobacter rubrum* sucrose isomerase (variant) |
| 9. SEQ ID NO: 9 nucleic acid sequence encoding *Enterobacter* species SZ62 sucrose isomerase |
| 10. SEQ ID NO: 10 amino acid sequence encoding *Enterobacter* species SZ62 sucrose isomerase |
| 11. SEQ ID NO: 11 nucleic acid sequence encoding *Serratia plymuthica* sucrose isomerase |
| 12. SEQ ID NO: 12 amino acid sequence encoding *Serratia plymuthica* sucrose isomerase |
| 13. SEQ ID NO: 13 nucleic acid sequence encoding fusion protein of *Erwinia rhaponthici* sucrose isomerase (palI) and signal peptide sequence of the proteinase inhibitor II gene |
| 14. SEQ ID NO: 14 amino acid sequence encoding fusion protein of *Erwinia rhaponthici* (palI) sucrose isomerase and signal peptide sequence of the proteinase inhibitor II gene |
| 15. SEQ ID NO: 15 nucleic acid sequence (complete cDNA with untranslated region) encoding *Klebsiella* sp. LX3 sucrose isomerase (isomaltulose synthase) |
| 16. SEQ ID NO: 16 amino acid sequence encoding *Klebsiella* sp. LX3 sucrose isomerase (isomaltulose synthase) |
| 17. SEQ ID NO: 17 nucleic acid sequence (open reading frame) encoding *Klebsiella* sp. LX3 sucrose isomerase (isomaltulose synthase) |
| 18. SEQ ID NO: 18 amino acid sequence encoding *Klebsiella* sp. LX3 sucrose isomerase (isomaltulose synthase) |
| 19. SEQ ID NO: 19 nucleic acid sequence encoding *Enterobacter* species SZ62 sucrose isomerase (fragment) |
| 20. SEQ ID NO: 20 amino acid sequence encoding *Enterobacter* species SZ62 sucrose isomerase (fragment) |
| 21. SEQ ID NO: 21 nucleic acid sequence encoding *Pseudomonas mesoacidophila* MX45 sucrose isomerase (fragment) |
| 22. SEQ ID NO: 22 amino acid sequence encoding *Pseudomonas mesoacidophila* MX45 sucrose isomerase (fragment) |
| 23. SEQ ID NO: 23 nucleic acid sequence encoding tomato (*Lycopersicum esculentum*) Lemmi9 promoter |
| 24. SEQ ID NO: 24 nucleic acid sequence encoding *Nicotiana tabacum* Δ0.3 TobRB7 promoter sequence (Region: -298 to +76) |
| 25. SEQ ID NO: 25 oligonucleotide primer FB83 5'-GGATCCGGTACCGTTCAGCAATCAAA T-3' |
| 26. SEQ ID NO: 26 oligonucleotide primer FB84 5'-GTCGACGTCTTGCCAAAAACCTT-3' |
| 27. SEQ ID NO: 27 oligonucleotide primer FB 97 5'-GTCGACCTACGTGATTAAGTTTATA-3' |
| 28. SEQ ID NO: 28 oligonucleotide primer Lem1 5'-atcGAATTCATAATTTAACCATCTAGA G-3' |
| 29. SEQ ID NO: 29 oligonucleotide primer Lem2 5'-atcGGTACCTGCTTCTGGAACGAAAGG G-3' |
| 30. SEQ ID NO: 30 oligonucleotide primer Tob1 5'-GGAATTCAGCTTATCTAAACAAAGTTTT AAATTC-3' |
| 31. SEQ ID NO: 31 oligonucleotide primer Tob2 5'-GGGTACCAGTTCTCACTAGAAAAATGCC CC-3 |
| 32. SEQ ID NO: 32 nucleic acid sequence encoding wheat dwarf virus V-sense promoter (Genbank Acc. No.: AX006849; sequence 1 in WO 00/01832) |
| 33. SEQ ID NO: 33 nucleic acid sequence encoding maize streak virus V-sense promoter (GenBank Acc. No.: AX006850; sequence 2 in WO 00/01832) |
| 34. SEQ ID NO: 34 nucleic acid sequence encoding pepper haustco virus V-sense promoter (GenBank Acc. No.: AX006851; sequence 3 in WO 00/01832) |
| 35. SEQ ID NO: 35 nucleic acid sequence encoding *Serratia plymuthica* sucrose isomerase |
| 36. SEQ ID NO: 36 amino acid sequence encoding *Serratia plymuthica* sucrose isomerase |

FIGURES

1. FIG. 1: Schematic representation of the expression cassette in the plasmid p35S-cwIso. The abbreviations denote:
   35S: 35S cauliflower mosaic virus (CaMV) promoter
   SP: signal peptide of the proteinase inhibitor II gene
   palI: *Erwinia rhapontici* sucrose isomerase gene
   OCS: polyadenylation signal of the octopine synthase gene
   EcoRI,Asp718,BamHI,SalI,HindIII: restriction cleavage sites
   Detailed description of the individual elements, see hereinbelow.

Figure 2:
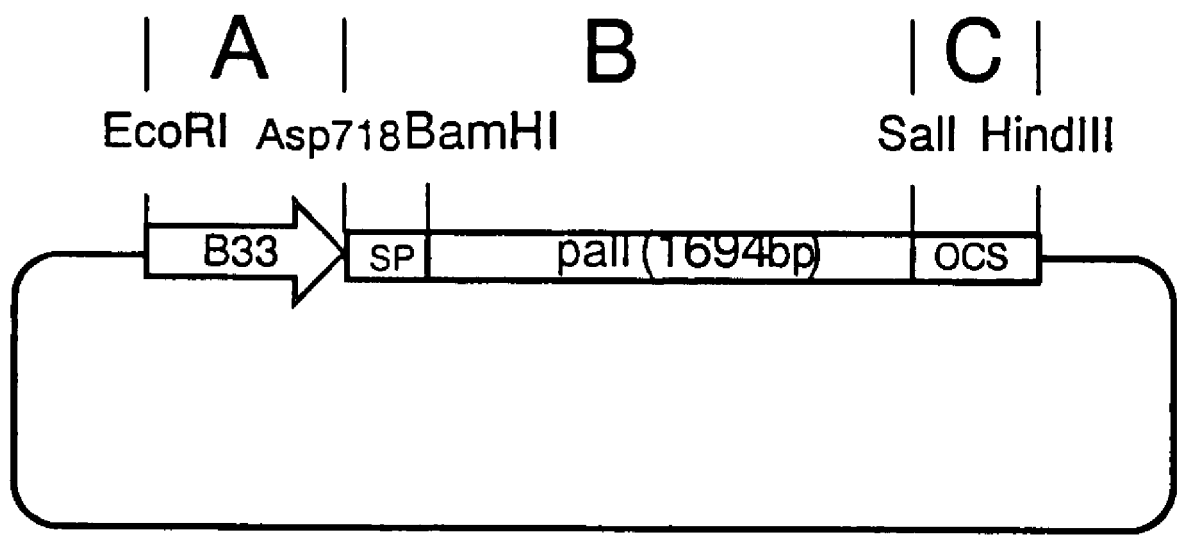
FIG. 2. Schematic representation of the expression cassette in the plasmid pB33-cwIso.

2. FIG. 2: Schematic representation of the expression cassette in the plasmid pB33-cwIso. The abbreviations denote:
   B33: promoter of the class I patatin gene B33
   SP: signal peptide of the proteinase inhibitor II gene
   palI: *Erwinia rhapontici* sucrose isomerase gene
   OCS: polyadenylation signal of the octopine synthase gene
   EcoRI,Asp718,BamHI,SalI,HindIII: restriction cleavage sites
   Detailed description of the individual elements, see hereinbelow.

Figure 3:
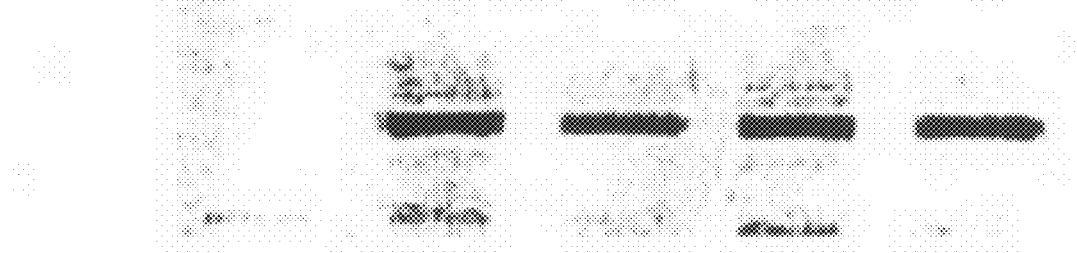
FIG. 3. Western blot analysis of pall-expressing potato tubers of various transgenic lines.

3. FIG. 3: Western blot analysis of palI-expressing potato tubers of various transgenic lines. 20 µg of soluble protein were applied to each lane of an SDS gel, separated and transferred to nitrocellulose. The filters were subsequently hybridized with a polyclonal PalI antibody. The expression in tubers from wild-type potato plants (wt) was compared with the expression in potato lines 5, 12, 26 and 33.

Figure 4:
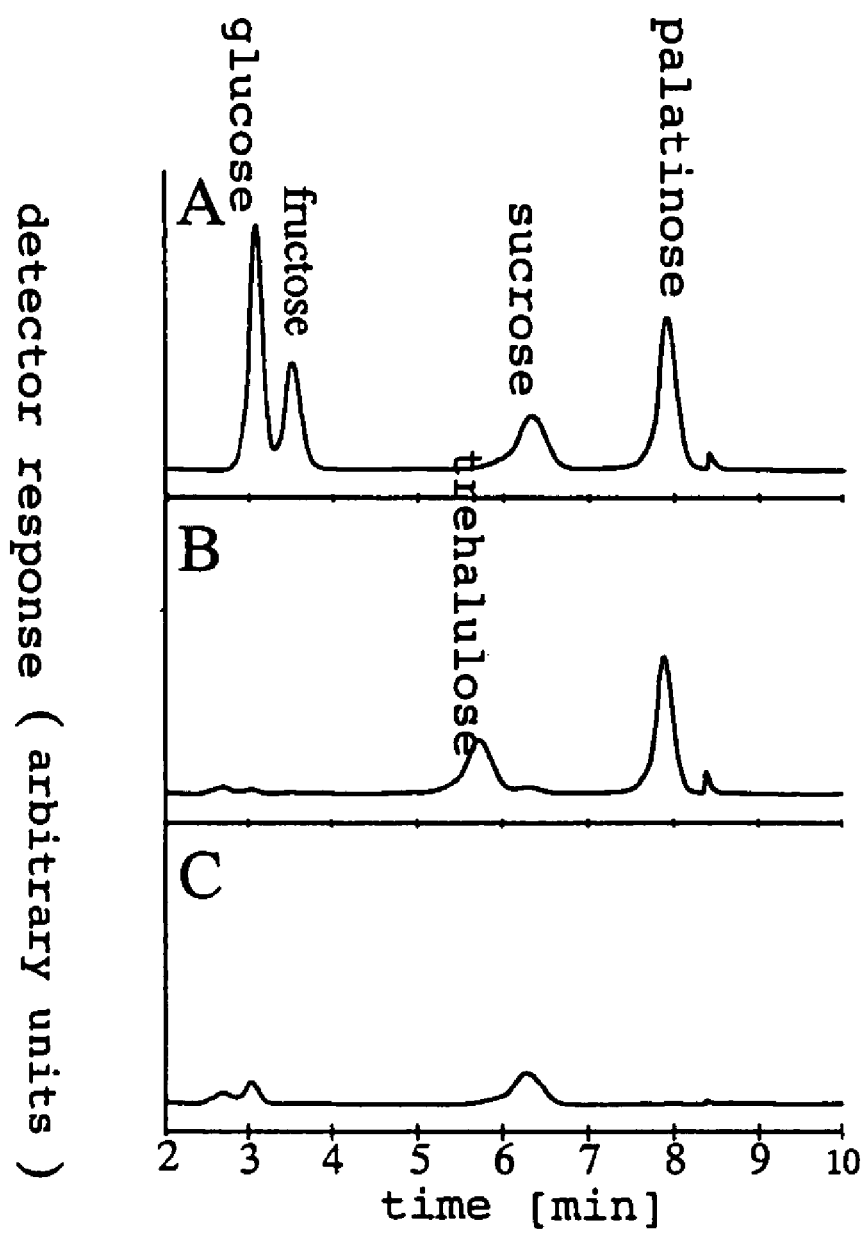
FIG. 4. HPLC analysis of the soluble carbohydrates in sucrose-isomerase -expressing plants.

4. FIG. 4: HPLC analysis of the soluble carbohydrates in sucrose-isomerase-expressing plants.
   A: Sugar standards.
   B: Extract from a transgenic tuber.
   C: Extract from a wild-type tuber.

Figure 5:
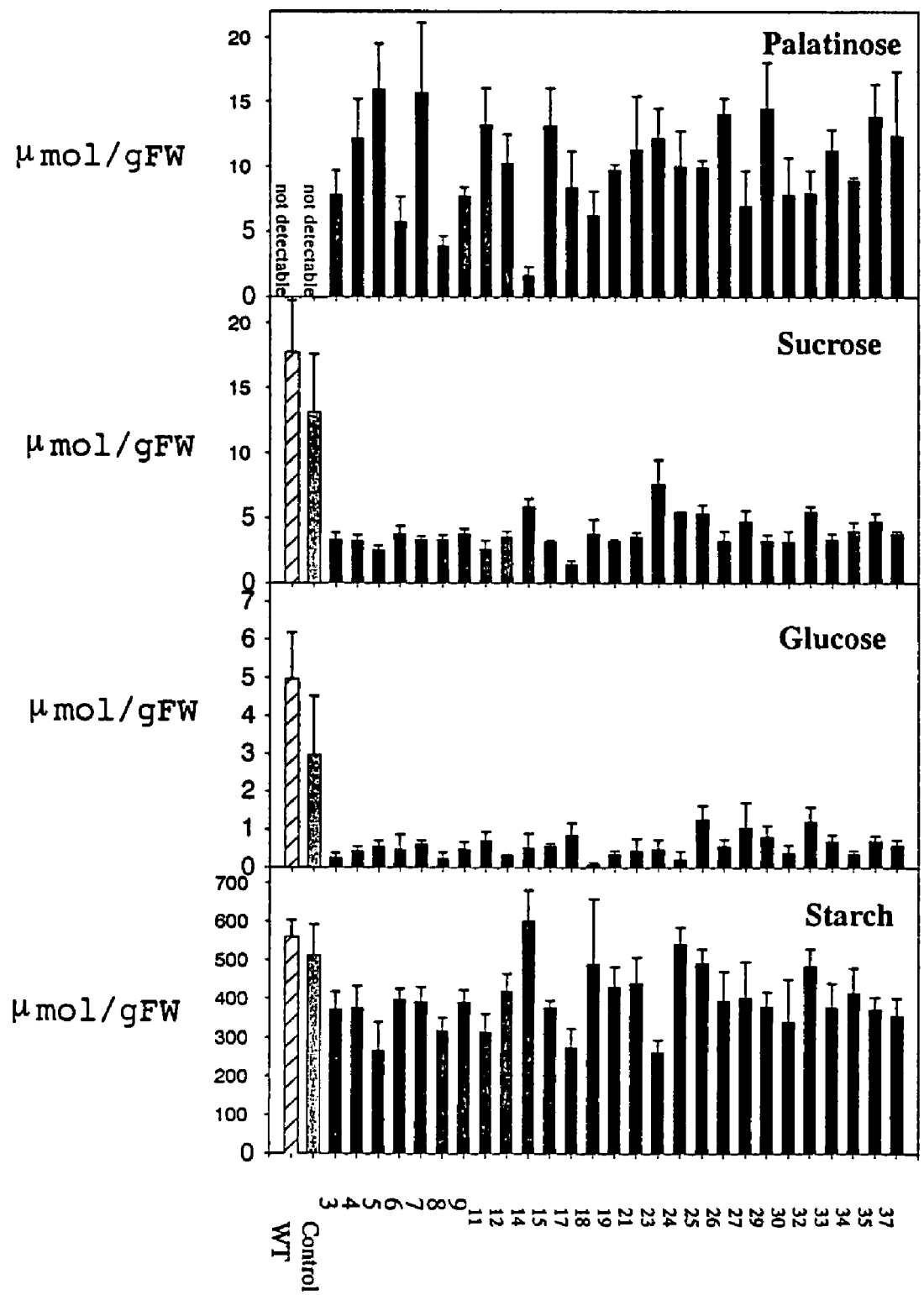
FIG. 5. Palatinose, sucrose, glucose and starch content in wild-type potato tubers (wt) and in potato tubers from various transgenic lines (3 to 37), which express the chimeric pall gene in the cell wall.

5. FIG. 5: Palatinose, sucrose, glucose and starch content in wild-type potato tubers (wt) and in potato tubers from various transgenic lines (3 to 37), which express the chimeric palI gene in the cell wall. The data of the wild type (wt; hatched columns) and the transgenic potato tubers (3 to 37; black columns) correspond to the means of four measurements±standard deviation. A transgenic, but not palI-expressing, line (control) was analyzed as additional control.

Figure 6:
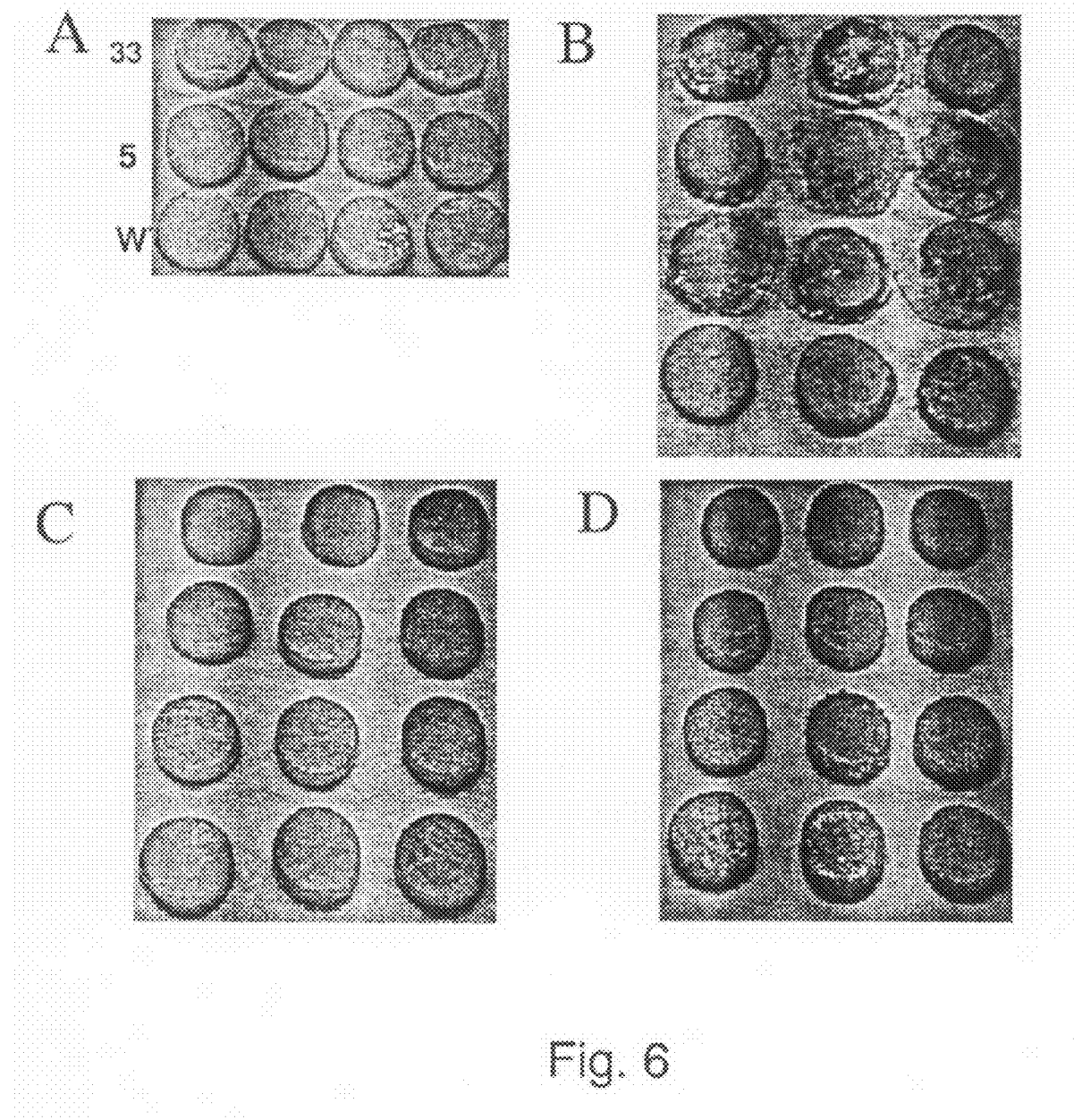
FIG. 6. Infection of potato tubers with Allernaria solani. Potato disks from wild -type tubers and tubers of the pall-expressing transgenic lines 5 and 33 14 days post -infection with Afternaria solani.
Figure 7:
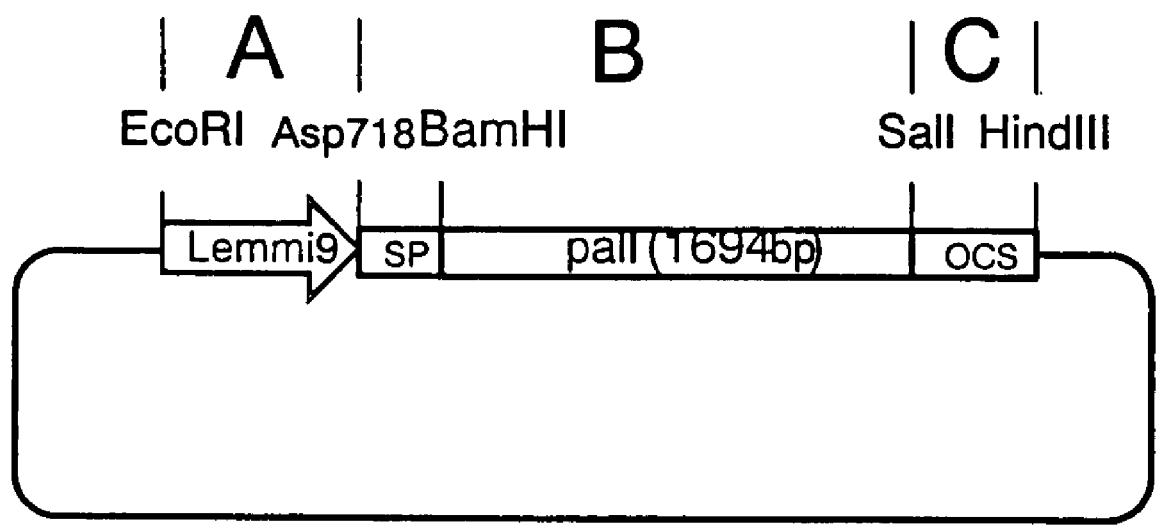
FIG. 7. Schematic representation of the expression cassette in the plasmid pLemmi9-cwIso.

6. FIG. 6: Infection of potato tubers with *Alternaria solani*. Potato disks from wild-type tubers and tubers of the palI-expressing transgenic lines 5 and 33; 14 days post-infection with *Alternaria solani*.
   A: Control with potato disks of wild-type (wt) and transgenic tubers (lines 5 and 33) after incubation for 14 days without previous *Alternaria*-infection.
   B: Wild-type tubers; 14 days after *Alternaria*-infection
   C: Transgenic line 5; 14 days after *Alternaria*-infection
   D: Transgenic line 33; 14 days after *Alternaria*-infection 7. FIG. 7: Schematic representation of the expression cassette in the plasmid pLemmi9-cwIso. The abbreviations denote:
   Lemmi9: tomato (*Lycopersicon esculentum*) Lemmi9 promoter
   SP: signal peptide of the proteinase inhibitor II gene
   palI: *Erwinia rhapontici* sucrose isomerase gene
   OCS: polyadenylation signal of the octopine synthase gene.
   EcoRI,Asp718,BamHI,SalI,HindIII: restriction cleavage sites
   Detailed description of the individual elements, see hereinbelow.

Figure 8:
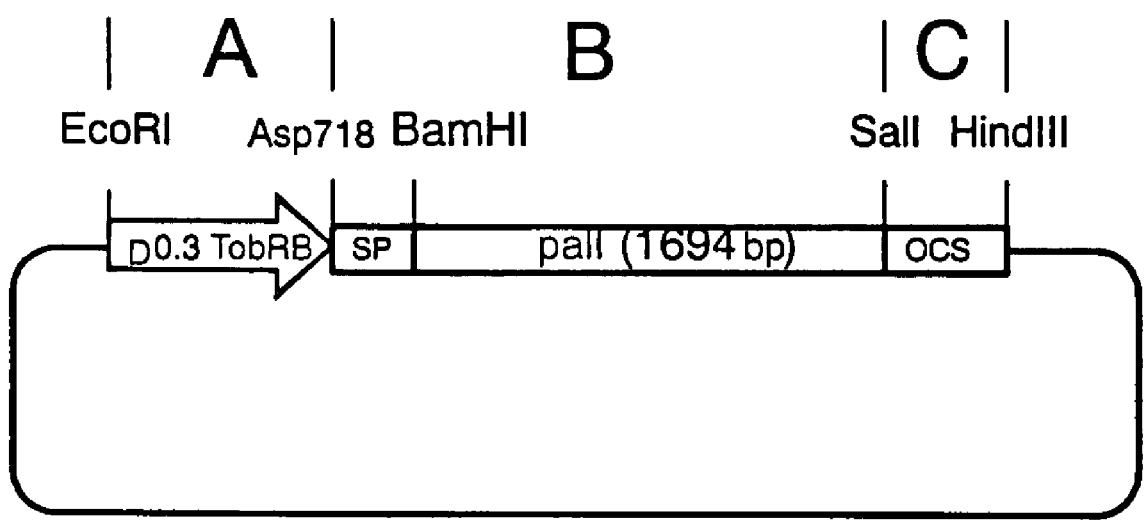
FIG. 8. Schematic representation of the expression cassette in the plasmid p Δ0.3TobRB7-cwIso.

8. FIG. 8: Schematic representation of the expression cassette in the plasmid pΔ0.3TobRB7-cwIso. The abbreviations denote:
   Δ0.3TobRB: *Nicotiana tabacum* Δ0.3TobRB7 promoter
   SP: signal peptide of the proteinase inhibitor II gene
   palI: *Erwinia rhapontici* sucrose isomerase gene
   OCS: polyadenylation signal of the octopine synthase gene
   EcoRI,Asp718,BamHI,SalI,HindIII: restriction cleavage sites
   Detailed description of the individual elements, see hereinbelow.

EXAMPLES

General Methods:

The chemical synthesis of oligonucleotides can be effected, for example, in the known fashion using the phosphoamidite method (Voet, Voet, 2nd Edition, Wiley Press New York, pages 896-897). The cloning steps carried out for the purposes of the present invention—such as, for example, restriction cleavages, agarose gel electrophoresis, purification of DNA fragments, transfer of nucleic acids to nitrocellulose and nylon membranes, linking DNA fragments, transformation of *E. coli* cells, growing bacteria, multiplying phages and sequence analysis of recombinant DNA—are carried out as described by Sambrook et al. (1989) Cold Spring Harbor Laboratory Press; ISBN 0-87969-309-6. The transformation of *Agrobacterium tumefaciens* was carried out in accordance with the method of Hofgen and Willmitzer ((1988) Nucl. Acids Res. 16:9877). The *Agrobacteria* were grown in YEB medium (Vervliet et al. (1975) Gen Virol 26:33). The sequencing of recombinant DNA molecules is carried out with an MWG-Licor laser fluorescence DNA sequencer following the method of Sanger (Sanger et al. (1977) Proc Natl Acad Sci USA 74:5463-5467).

Example 1

PCR Amplification of a Subfragment of the *Erwinia rhapontici* Sucrose Isomerase A subfragment of the sucrose isomerase was cloned by means of polymerase chain reaction (PCR). The template material was genomic DNA from *E. rhapontici* (DSM 4484), which was isolated by a standard protocol. Amplification was carried out using the following specific primers, which were derived from a prior-art sucrose isomerase sequence:

```
FB83
5'-GGATCCGGTACCGTTCAGCAATCAAAT-3'   (SEQ ID NO: 25)

FB84
5'-GTCGACGTCTTGCCAAAAACCTT-3'       (SEQ ID NO: 26)
```

Primer FB83 comprises the bases 109 to 127 and primer FB84 the bases 1289 to 1306 of the coding region of the *E. rhapontici* sucrose isomerase gene.

The PCR reaction mixture (100 µl) comprised:
chromosomal bacterial DNA (1 µg)
primers FB 83 and FB 84 (250 ng each),
Pfu DNA polymerase reaction buffer (10 µl, Stratagene),
200 µM dNTPs (dATP, dCTP, dGTP, dTTP) and
2.5 units Pfu DNA polymerase (Stratagene).

Before starting the amplification cycles, the mixture was heated for 5 minutes at 95° C. The polymerization steps (30 cycles) were carried out in an automatic T3 thermocycler (Biometra) with the following program: denaturation 95° C.

(1 minute), annealing of the primers at 55° C. (40 seconds), polymerase reaction at 72° C. (2 minutes). The resulting fragment was cloned into the vector pCR-Blunt (Invitrogen). The identity of the amplified DNA was verified by means of sequence analysis.

The subfragment which has been amplified can also be employed as hybridization probe for the isolation of further sucrose isomerase DNA sequences from other organisms or as probe in the analysis of transgenic cells and plants.

Example 2

PCR Amplification of an *Erwinia rhapontici* Sucrose Isomerase

Using the fragment amplified in Example 1, a genomic *Erwinia rhapontici* library was screened by standard methods. Subsequent sequence analysis permitted the determination of the open reading frame of sucrose isomerase. The oligonucleotide primers FB83 and FB97 were derived from this sequence.

The complete open reading frame of sucrose isomerase was cloned by means of polymerase chain reaction (PCR). Genomic DNA from *E. rhapontici* (DSM 4484) which had been isolated following a standard protocol acted as template material. The amplification was carried out using the following specific primers:

```
FB83
5'-GGATCCGGTACCGTTCAGCAATCAAAT-3'    (SEQ ID NO: 25)

FB97
5'-GTCGACCTACGTGATTAAGTTTATA-3'      (SEQ ID NO: 27)
```

Primer FB83 comprises the bases 109 to 127 and primer FB97 the bases 1786 to 1803 of the coding region of the sucrose isomerase gene. To clone the amplified DNA into expression vectors, the primers additionally have the following restriction cleavage sites: primer FB 83, BamHI, and primer FB 97, SalI.

The PCR reaction mixture (100 μl) comprised:
chromosomal bacterial DNA (1 μg),
primers FB83 and FB97 (250 ng each),
Pfu DNA polymerase reaction buffer (10 μl, Stratagene),
200 μM dNTPs (dATP, dCTP, dGTP, dTTP) and
2.5 units Pfu DNA polymerase (Stratagene).

Before starting the amplification cycles, the mixture was heated for 5 minutes at 95° C. The polymerization steps (30 cycles) were carried out in an automatic T3 thermocycler (Biometra) with the following program: denaturation 95° C. (1 minute), annealing of the primers at 55° C. (40 seconds), polymerase reaction at 72° C. (2 minutes). The sucrose isomerase fragment which had been amplified was cloned into the vector pCR-Blunt (Invitrogen), giving rise to the plasmid pCR-SucIso2 (without translation origin). The identity of the amplified DNA was verified by means of sequence analysis. The PCR fragment thus comprises the sequence of an *E. rhapontici* sucrose isomerase which extends from nucleotide 109-1803 of the sucrose isomerase gene.

Example 3

Generation of Plasmid p35S-cwIso

A DNA sequence which encodes a sucrose isomerase was isolated from the plasmid, pCR-SucIso2 and provided with the cauliflower mosaic virus 35S promoter, which mediates constitutive expression in transgenic plant cells, and with a plant termination signal. The plant termination signal comprises the 3' end of the polyadenylation site of the octopine synthase gene.

Moreover, a signal peptide of a plant gene (potato proteinase inhibitor II gene (Keil et al. (1986) Nucl Acids Res 14:5641-5650; Genbank Acc. No.: X04118)), which is required for the uptake into the endoplasmic reticulum, was fused upstream of the coding sequence of the sucrose isomerase gene. To this end, the sucrose isomerase fragment was excised from the construct pCR-SucIso2 via the restriction cleavage sites BamHI and SalI and ligated into a BamHI/SalI-linearized pMA vector. The vector pMA is a modified form of the vector pBinAR (Höfgen and Willmitzer (1990) Plant Sci. 66:221-230), which comprises the cauliflower mosaic virus 35S promoter, which mediates constitutive expression in transgenic plants, a signal peptide of the potato proteinase inhibitor II, which mediates targeting of the fusion protein into the cell wall, and a plant termination signal. The plant termination signal comprises the 3' end of the polyadenylation site of the octopine synthase gene. Between the part-sequence of the proteinase inhibitor and the termination signal there are located cleavage sites for the restriction enzymes BamHI, XbaI, SalI, PstI and SphI (in this order), which make possible the insertion of suitable DNA fragments so that a fusion protein between the proteinase inhibitor signal peptide and the inserted protein is formed, which is then transported into the cell wall of transgenic plant cells which express this protein. Thus, the expression cassette in the plasmid p35S-cwIso consists of the fragments A, B and C (FIG. 1):

A) Fragment A comprises the cauliflower mosaic virus 35S promoter (CaMV). It comprises a fragment comprising the nucleotides 6909 to 7437 of the CaMV (Franck (1980) Cell 21:285).

B) Fragment B comprises the nucleotides 923 to 1059 of a potato proteinase inhibitor II gene (Keil et al., supra), which are fused via a linker with the sequence ACC GAA TTG GG to the *Erwinia rhapontici* sucrose isomerase gene, which comprises the nucleotides 109 to 1803. Thus, a signal peptide of a plant protein, which is required for the uptake of proteins. into the endoplasmic reticulum (ER) is fused N-terminally to the sucrose isomerase sequence.

C) Fragment C comprises the polyadenylation signal of the octopine synthase gene (Dhaese et al. (1983) EMBO J. 2:419-426. GenBank Acc. No.: Z37515, nucleotides 1344 to 1533).

In p35S-cwIso (35S=35S promoter, cw=cell wall, Iso=sucrose isomerase), the coding region of the *E. rhapontici* sucrose isomerase is under constitutive control, the gene product is taken up into the ER and subsequently secreted.

Example 4

Generation of Plasmid pB33-cwIso

The plasmid pB33-cwIso was generated using the binary plasmid p35S-cwIso. In doing so, the 35S promoter was exchanged for the promoter of the class I patatin gene (Rocha-Sosa et al (1989) EMBO J 8:23-29). Thus, the expression cassette of this plasmid pB33-cwIso consists of the three fragments A, B and C (see FIG. 2):

A) Fragment A comprises the region −1512 to +14 relative to the transcription initiation site of the class I patatin gene. The promoter region was ligated, in the form of a DraI fragment, into the SstI-cut vector pUC18, whose ends had been filled up using T4 DNA polymerase and thus been made blunt ended. The fragment was subsequently reexcised from the vector pUC18 using the restriction enzymes EcoRI and Asp718 and cloned into the plasmid p35S-cwIso, from which the 35S CaMV promoter had previously been deleted after partial restriction with the enzymes EcoRI and Asp718.

B) Fragment B comprises the nucleotides 923 to 1059 of a potato proteinase inhibitor II gene, which are fused via a linker with the sequence ACC GAA TTG GG to the *E. rhapontici* sucrose isomerase gene, which comprises the nucleotides 109 to 1803. Thus, a signal peptide of a plant protein, which is required for the uptake of proteins into the ER is fused N-terminally to the sucrose isomerase sequence.

C) Fragment C comprises the polyadenylation signal of the octopine synthase gene (Dhaese et al. (1983) EMBO J 2:419-426; GenBank Acc. No.: Z37515, nucleotides 1344 to 1533).

In pB33-cwIso (B33=promoter of the class I patatin gene B33, cw=cell wall, Iso=sucrose isomerase), the coding region of the *E. rhapontici* sucrose isomerase is under tissue-specific control, the gene product is taken up into the ER.

Example 5

Transformation of Potatoes, and Selection of Transgenic Plants 20 small leaves from a sterile potato culture (*Solanum tuberosum* L. cv. Solara), which had been wounded with a surgical blade, were placed into 10 ml of MS medium supplemented with 2% sucrose and comprising 50 µl of an *Agrobacterium tumefaciens* overnight culture grown under selection. After gentle shaking for 5 minutes, the Petri dishes were incubated in the dark at 25° C. After two days, the leaves were plated on MS medium supplemented with 1.6% glucose, 2 mg/l zeatin ribose, 0.02 mg/l giberellic acid, 500 mg/l clafloran, 50 mg/l kanamycin and 0.8% Bacto agar. After incubation for one week at 25° C. and 3000 Lux, the claforan concentration in the medium was halved. Cultivation was continued for one week under known conditions (Rocha-Sosa et al. (1989) EMBO J 8:23-29).

Using the plasmid pB33-cwIso, the *Agrobacterium*-mediated transformation was followed by the regeneration of a total of 36 kanamycin-resistant potato plants. The tubers of these plants were examined for palI expression with the aid of a polyclonal anti-body against the recombinant PaII protein (Börnke et al. (2002) Planta 214:356-364). palI-expression was detected in a Western blot in 25 lines. A Western blot of representative lines is shown in FIG. 3.

Example 6

HPLC Analysis of the Transgenic pB33-cwIso Potatoes

Tuber extracts of the transgenic lines were analyzed via HPLC for their soluble carbohydrate content with the purpose of detecting the in-vivo conversion of sucrose to palatinose. The HPLC analysis was carried out by the method described in Börnke et al. (2002) Planta 214:356-364. The preparation of the tuber extract is described by Sonnewald et al.(1992) Plant J 2:571-581. The results of the HPLC analysis are shown in FIG. 4.

As shown by the chromatograms, the expression of sucrose isomerase in the cell wall results in a substantial accumulation of palatinose in the tubers of the pB33-cwIso lines studied. The wild type comprises no palatinose, as can likewise be seen clearly from the chromatograms. The soluble sugar content in the transgenic potato tubers-comprising the construct pB33-cwIso is shown in FIG. 5. The palatinose content in the potato tubers varies between the individual transgenic lines between 1.7 µmol/g FW (FW: "fresh weight") (line 14) and 16 µmol/g FW (line 5).

Example 7

Infection of Potato Disks with *Alternaria solani*

*Alternaria solani* (provided by Dr. Jürgen Sigrist, Zentrum für Grüne Gentechnik [Center for Green Genetic Engineering], Neustadt an der Weinstraße) were maintained for 14 days at 16° C. on PDA agar (Duchefa, The Netherlands) (PDA=potato dextrose agar). The spores were isolated by scraping in water and the resulting suspension was freed from solid constituents by means of Miracloth. The spore count was determined in a hematocytometer (Thoma) and brought to 10 000 spores/ml. 25 µl (accordingly 250 spores) were applied per potato disk (1.5 cm diameter) and distributed uniformly. The inoculated disks were subsequently incubated at 16° C. Scoring was done visually. The result after incubation for 14 days is shown in FIG. 6. As can be seen from the figure, the growth of the fungus on transgenic potato tubers which express sucrose isomerase is markedly reduced in comparison with the wild type.

Example 8

Generation of the Plasmid pLemmi9-cwIso

To generate the plasmid pLemmi9-cwIso the promoter of the class I patatin gene B33 in plasmid pB33-cwIso was exchanged for the Lemmi9 promoter (Escobar et al. (1999) Mol Plant Microbe Interact 12:440-449), and the fusion protein of proteinase inhibitor II signal peptide and sucrose isomerase was thus placed under the control of the feeding-cell-specific promoter.

The functionality of the feeding-cell-specific. Lemmi9 promoter has already been demonstrated (Escobar C et al. (1999) Mol Plant Microbe Interact 12:440-449). The plasmid pLemmi9-cwIso comprises three fragments A, B and C (see FIG. 7):

A) Fragment A comprises the tomato (*Lycopersicon esculentum*) Lemmi9 promoter. The fragment comprises the 1417 bp sequence upstream of the translation start (ATG) of the Lemmi9 gene and has been characterized as a functional promoter fragment (Escobar et al. (1999) Mol Plant Microbe Interact 12: 440-449, Accession Z69032). It was amplified by means of PCR from genomic tomato (*Lycopersicon esculentum*) DNA. The amplification was carried out using the following specific primers:

Lem1:
5'atcGAATTCATAATTTAACCATCTAGAG 3'    (SEQ ID NO: 28)

Lem2:
5'atcGGTACCTGCTTCTGGAACGAAAGGG 3'    (SEQ ID NO: 29)

In order to clone the DNA into the expression cassette, the primers additionally have the following restriction cleavage sites: Primer Lem1, EcoRI; Primer Lem2, Asp718.

The PCR reaction mixture (100 µl) comprised:
genomic tomato DNA (1 µg),
primers Lem1 and Lem2 (250 ng each), Pfu DNA polymerase reaction buffer (10 μl, Stratagene),
200 μM dNTPs (dATP, dCTP, dGTP, dTTP) and
2.5 units Pfu DNA polymerase (Stratagene).

Before starting the amplification cycles, the mixture was heated for 5 minutes at 95° C. The polymerization steps (30 cycles) were carried out in an automatic T3 thermocycler (Biometra) with the following program: denaturation 95° C. (1 minute), annealing of the primers at 56° C. (40 seconds), polymerase reaction at 72° C. (3 minutes). The amplicon was digested with the restriction enzymes EcoRI and Asp718. and cloned into the corresponding restriction cleavage sites of the pBluescript polylinker (Stratagene). The identity of the DNA which had been amplified was verified by sequence analysis. Thereafter, the fragment was digested with the restriction enzymes EcoRI and Asp718 and cloned into the plasmid pB33-cwIso, from which the B33 promoter had previously been deleted after partial restriction with the enzymes EcoRI and Asp718.

B) Fragment B comprises the nucleotides 923 to 1059 of the potato proteinase inhibitor II gene (Keil et al. (1986) Nucl Acids Res 14:5641-5650; Genbank Acc. No.: x04118), which are fused via a linker with the sequence ACC GAA TTG GG to the *E. rhapontici* sucrose isomerase gene, which comprises the nucleotides 109 to 1803. Thus, a signal peptide of a plant protein, which is required for the uptake of proteins into the ER is fused N-terminally to the sucrose isomerase sequence.

C) Fragment C comprises the polyadenylation signal of the octopine synthase gene (Dhaese et al. (1983). EMBO J 2:4.19-426. Accession Z37515, nucleotides 1344 to 1533).

In pLemmi9-cwIso (Lemmi9=promoter of the tomato (Lycopersicon esculentum) Lemmi9 gene, cw=cell wall, Iso=sucrose isomerase), the coding region of the sucrose isomerase gene is under feeding-cell-specific control, the gene product is taken up into the ER.

A control construct for expressing β-glucuronidase (Jefferson et al. (1987) EMBO J 6:3901-3907) under the control of the Lemmi9 promoter (pLemmi9-GUS) was generated analogously.

Potato cells were transformed with the construct pLemmi9-cwIso or pLemmi9-GUS as described above by means of *Agrobacterium*-mediated gene transfer, and intact potato plants were regenerated.

Example 9

Generation of the Plasmid pΔ0.3TobRB7-cwIso

To generate the plasmid pΔ0.3TobRB7-cwIso, the promoter of the class I patatin gene B33 in plasmid pB33-cwIso was exchanged for the Δ0.3TobRB7 promoter (Opperman et al. (1994) Science 263:221-223) and the fusion protein of proteinase inhibitor signal peptide and sucrose isomerase thus placed under feeding-cell-specific control.

The functionality of the feeding-cell-specific Δ0.3TobRB7 promoter has already been demonstrated (Opperman et al. (1994) Science 263:221-223). The plant termination signal comprises the 3' end of the polyadenylation site of the octopine synthase gene. The plasmid pΔ0.3TobRB7-cwIso comprises three fragments A, B and C (FIG. 8):

A) Fragment A comprises the *Nicotiana tabacum* Δ0.3TobRB7 promoter. The fragment comprises the region from −298 bp to +76 of the TobBR7 gene located and characterized as functional promoter fragment (Opperman et al. (1994) Science. 263: 221-223, Acc. No.: S45406). It was amplified by means of PCR from genomic DNA of *Nicotiana tabacum* var. Samsun NN. The amplification was performed using the following specific primers:

```
Tob1:
5'-GGAATTCAGCTTATCTAAACAAAGTTTTAA    (SEQ ID NO: 30)
ATTC-3'

Tob2:
5'-GGGTACCAGTTCTCACTAGAAAAATGCCC    (SEQ ID NO: 31)
C-3'
```

In order to clone the DNA into the expression cassette, the primers additionally have the following restriction cleavage sites: primer Tob1, EcoRI; primer Tob2, Asp718.

The PCR reaction mixture (100 μl) comprised:
genomic tobacco DNA (1 μg),
primers Tob1 and Tob2 (250 ng each),
Pfu DNA polymerase reaction buffer (10 μl, Stratagene),
200 μM dNTPs (dATP, dCTP, dGTP, dTTP) and
2.5 units Pfu DNA polymerase (Stratagene).

Before starting the amplification cycles, the mixture was heated for 5 minutes at 95° C. The polymerization steps (30 cycles) were carried out in an automatic T3 thermocycler (Biometra) with the following program: denaturation 95° C. (1 minute), annealing of the primers at 56° C. (40 seconds), polymerase reaction at 72° C. (3 minutes). The amplicon was digested with the restriction enzymes EcoRI and Asp718 and cloned into the corresponding restriction cleavage sites of the pBluescript polylinker (Stratagene). The identity of the DNA which had been amplified was verified by sequence analysis. Thereafter, the fragment was digested with the restriction enzymes EcoRI and Asp718 and cloned into the plasmid pB33-cwIso, from which the B33 promoter had previously been deleted after restriction with the enzymes EcoRI and Asp718.

B) Fragment B comprises the nucleotides 923 to 1059 of a potato proteinase inhibitor II gene (Keil et al. (1986) Nucl. Acids Res. 14:5641-5650; Genbank Acc. No.: x04118), which are fused to the *E. rhapontici* sucrose isomerase gene, which comprises the nucleotides 109 to 1803. Thus, a signal peptide of a plant protein, which is required for the uptake of proteins into the ER is fused N-terminally to the sucrose isomerase sequence.

C) Fragment C comprises the polyadenylation signal of the octopine synthase gene (Dhaese et al. (1983) EMBO J 2:419-426. Accession Z37515, nucleotides 1344 to 1533).

In pΔ0.3TobRB7-cwIso (Δ0.3TobRB7=truncated promoter of the tobacco TobRB7 gene, cw=cell wall, Iso=sucrose isomerase), the coding region of the sucrose isomerase gene is under feeding-cell-specific control, the gene product is taken up into the ER.

A control construct for expressing β-glucuronidase (Jefferson et al. (1987) EMBO J 6:3901-390.7) under the control of the Δ0.3TobRB7 promoter was prepared analogously (pΔ0.3TobRB7-GUS).

Potato cells were transformed with the construct pΔ0.3TobRB7-cw I-so or pΔ0.3TobRB7-GUS as described above by means of *Agrobacterium*-mediated gene transfer, and potato plants were regenerated.

Example 10

Infection of the Plants with Nematodes

Transformed plants are verified via PCR with the aid of npt-specific primers. For the infection with nematodes, the cuttings of transgenic lines which express sucrose isomerase under the control of a feeding-cell-specific promoter are first grown on medium supplemented with kanamycin and later transferred to pots containing sterile soil. The plants are grown at 22° C. (16-h-day/8-h-night). The plants are infected as follows: 3 ml of a suspension (approx. 500 J2 larvae) of root-knot nematodes (Meloidogyne species) are inoculated into the soil directly next to the stems of the plants. After 2 to 3 weeks, the plants are removed from the pots and the roots are washed. Thereafter, all of the root of each plant is examined with the aid of a stereomicroscope, and the number of root knots on the root system of transgenic plants and wild-type plants is compared.

Transgenic plants which express sucrose isomerase under the control of a feeding-cell-specific promoter show a pronounced resistance to endoparasitic root nematodes. The number of galls on the root system of these plants following infestation with nematodes is reduced significantly in comparison with untransformed plants.

Example 11

In-Vitro Nematode Resistance Test

Materials:
Plants: Potato (*Solanum tuberosum* L. cv. Solara)
Nematodes: *Meloidogyne incognita*
Medium: Modified Murashige & Skoog medium (MSm; solidified with agar) consisting of micro elements and ½ macro elements, including vitamins, sucrose and Diachin agar (0.7%), pH 5.8.
Plants: Sterile transgenic potato plants (*Solanum tuberosum* L. cv. Solara transformed with pΔ0.3TobRB7-cwIso or pLemmi9-cwIso) and corresponding transgenic control plants (*Solanum tuberosum* L. cv. Solara transformed with pΔ0.3TobRB7-GUS or pLemmi9-GUS) were provided in glass jars comprising several plants each. Starting from each plant, in each case three lines were generated by means of stem segments and subsequent cultivation on modified Murashige & Skoog medium (MSm; solidified with agar). Each line was planted out on a separate 9 cm Petri dish. The plants were grown for 2 to 3 weeks in a light/dark regime of 16 hours light/8 hours dark at 25° C.

Nematode Stock Culture:
Nematodes were obtained from sterile stock cultures. *M. incognita* was grown monoxenically in the dark at 25° C. on *Cucumis sativus* root explants as described by Wyss et al. (Wyss U et al. (1992) Nematologica 38:98-111). Egg sacks were collected from the sterile cultures and placed on a sieve in a glass funnel with sterile water. The funnels were connected to plastic tubing sealed with clamps. Hatched juveniles were obtained by opening the clamp and decanting the suspension into small vessels. The viscosity of the suspension was increased by adding a suspension of sterile "Gel Rite". The nematode density in the suspension was determined and standardized by adding sterile water.

Inoculation with Nematodes
As soon as the plant roots had developed a root system, the roots were inoculated with freshly hatched juvenile second-instar nematodes (J2). Ten drops comprising in each case 10 juveniles were applied to each plant.

Evaluation:
After 2 to 3 weeks, the nematodes had penetrated the roots, and galls had formed in the control plants. Gall development was used to indicate successful penetration and the establishment of feeding sites in the roots. The roots of the various plant lines were examined for galls under the microscope, and the galls were recorded on the Petri dish.

In comparison with the control plants, the potato lines transformed with pΔ0.3TobRB7-cwIso or pLemmi9-cwIso revealed a significantly reduced gall development. This means a significant reduction in the damage caused by the nematodes.

The invention claimed is:

1. A method for generating or increasing resistance of a plant to at least one pathogen comprising:
   a) transforming a collection of plant cells with a nucleic acid encoding a transgenic protein that possesses a sucrose isomerase activity and has the sequence set forth in SEQ ID NO: 14; and
   b) selecting a plant cell from the transformed collection that generates or shows increased resistance, as compared to the untransformed plant cell, to the at least one pathogen.

2. The method of claim 1, wherein the sucrose isomerase protein is expressed under the control of a pathogen-inducible or tissue-specific promoter which is functional in plants.

3. The method of claim 1, wherein the pathogen is selected from the group consisting of Plasmodiophoamycota, Oomycota, Ascomycota, Chytridiomycetes, Zygomycetes, Basidiomycota and Deuteromycetes.

4. The method of claim 1, wherein the plant is selected from the group consisting of potato, beet, sugar beet, tomato, banana, carrot, sugar cane, strawberry, pineapple, paw paw, soybean, oats, barley, wheat, rye, triticale, sorghum, millet, and maize.

5. A transgenic expression cassette comprising a nucleic acid sequence that encodes a sucrose isomerase having the sequence set forth in SEQ ID NO:14, which is in functional linkage with a pathogen-inducible promoter that is functional in plants.

6. The transgenic expression cassette of claim 5, further comprising a pathogen-inducible promoter which contains a sequence selected from the group consisting of the sequences of SEQ ID NO:23, 24, 32, 33 and 34.

7. A transgenic expression vector comprising the transgenic expression cassette of claim 5.

8. A transgenic plant comprising the transgenic expression cassette of claim 5.

9. The transgenic plant of claim 8, wherein the species is selected from the group consisting of potato, beet, sugar beet, tomato, banana, carrot, sugar cane, strawberry, pineapple, paw paw, soybean, oats, barley, wheat, rye, triticale, sorghum, millet, and maize.

10. A transgenic crop product, propagation material, cells, organs, parts, calli, cell cultures, seeds, tubers, sets or transgenic progeny of the transgenic plant of claim 8.

* * * * *